United States Patent
Shiozaki et al.

(10) Patent No.: US 8,580,751 B2
(45) Date of Patent: Nov. 12, 2013

(54) ESTERIFIED α-GALACTOSYLCERAMIDE

(75) Inventors: Masao Shiozaki, Kanagawa (JP); Takuya Tashiro, Kanagawa (JP); Kenji Mori, Kanagawa (JP); Ryusuke Nakagawa, Kanagawa (JP); Hiroshi Watarai, Kanagawa (JP); Masaru Taniguchi, Kanagawa (JP)

(73) Assignee: Riken, Wako (JP)

( * ) Notice: Subject to any disclaimer, the term of this patent is extended or adjusted under 35 U.S.C. 154(b) by 137 days.

(21) Appl. No.: 13/063,647

(22) PCT Filed: Sep. 11, 2009

(86) PCT No.: PCT/JP2009/065963
§ 371 (c)(1),
(2), (4) Date: Jun. 6, 2011

(87) PCT Pub. No.: WO2010/030012
PCT Pub. Date: Mar. 18, 2010

(65) Prior Publication Data
US 2011/0224158 A1    Sep. 15, 2011

(30) Foreign Application Priority Data
Sep. 11, 2008    (JP) .................... 2008-233713

(51) Int. Cl.
*C07H 15/06*    (2006.01)
*A61K 31/70*    (2006.01)

(52) U.S. Cl.
USPC .......................... 514/25; 536/18.2

(58) Field of Classification Search
None
See application file for complete search history.

(56) References Cited

U.S. PATENT DOCUMENTS

| | | | |
|---|---|---|---|
| 5,849,716 A | 12/1998 | Akimoto et al. | |
| 2002/0032158 A1 | 3/2002 | Tomiyama et al. | |
| 2005/0222048 A1 | 10/2005 | Tsuji et al. | |
| 2006/0052316 A1 | 3/2006 | Porcelli | |
| 2007/0238673 A1 | 10/2007 | Porcelli | |
| 2007/0275908 A1 | 11/2007 | Defrees et al. | |
| 2010/0062990 A1 | 3/2010 | Tashiro et al. | |

FOREIGN PATENT DOCUMENTS

| DE | 10128250 A1 | 12/2001 |
|---|---|---|
| JP | 2006-117582 A | 5/2006 |
| JP | 2006-519878 A | 8/2006 |
| JP | 2007-531768 A | 11/2007 |
| JP | 2008-511634 A | 4/2008 |
| WO | 94/09020 A1 | 4/1994 |
| WO | 03/105769 A2 | 12/2003 |
| WO | 2008/102888 A1 | 8/2008 |

OTHER PUBLICATIONS

Graziani et al., Tetrahedron: Asymmetry, 2000, vol. 11 (19), pp. 3921-3937.*
Burdin et al., *The Journal of Immunology*, 161: 3271-3281 (1998).
Chen et al., *Organic Letters*, 6(22): 4077-4080 (2004).
Ciliberti et al., *Eur. J. Org. Chem.*, 9: 1463-1473 (2007).
Fan et al., *Tetrahedron*, 61: 1855-1862 (2005).
Graziani et al., *Tetrahedron: Asymmetry*, 11(19): 3921-3937 (2000).
Iijima et al., *Bioorganic & Medicinal Chemistry*, 6: 1905-1910 (1998).
Karlsson et al., *Biochimica et Biophysica Acta*, 316: 317-335 (1973).
Kawano et al., *Proc. Natl. Acad. Sci. USA*, 95: 5690-5693 (1998).
Kawano et al., *Science*, 278: 1626-1629 (1997).
Lee et al., *Carbohydrate Research*, 101: 39-47 (1982).
Morita et al., *J. Med. Chem.*, 38: 2176-2187 (1995).
Motoki et al., *Biol. Pharm. Bull.*, 18(11): 1487-1491 (1995).
Passacantilli et al., *Eur. J. Org. Chem.*, 2004(24): 5083-5091 (2004).
Passacantilli et al., *Eur. J. Org. Chem.*, 2006(14): 3097-3104 (2006).
Passacantilli et al., *Tetrahedron*, 60(31): 6453-6459 (2004).
Schmieg et al., *J. Exp. Med.*, 198(1): 1631-1641 (Dec. 2003).
Taniguchi et al., *Nature Immunology*, 4(12): 1164-1165 (2003).
Tashiro et al., *Tetrahedron Letters*, 48: 3343-3347 (2007).

(Continued)

*Primary Examiner* — Traviss C McIntosh, III
(74) *Attorney, Agent, or Firm* — Leydig, Voit & Mayer, Ltd.

(57) ABSTRACT

The invention provides esterified α-galactosylceramides effective for cancer treatment and the like, and a medicament containing same. In particular, the invention relates to a compound represented by the formula (I):

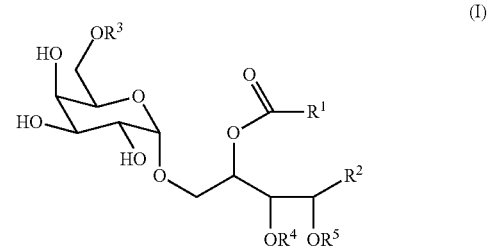

wherein $R^1$ is a hydrocarbon group having a carbon number of 1 to 30, $R^2$ is a hydrocarbon group having a carbon number of 1 to 20, $R^3$ is a hydrogen atom or hydrocarbon group having a carbon number of 1 to 5, $R^4$ and $R^5$ are the same or different and each is a hydrogen atom or a hydrocarbon group having a carbon number of 1 to 5, or $R^4$ and $R^5$ in combination form a divalent hydrocarbon group having a carbon number of 1 to 5, and optionally form a ring structure together with the adjacent ethylenedioxy, or a salt thereof.

15 Claims, 3 Drawing Sheets

(56) References Cited

OTHER PUBLICATIONS

Uchimura et al., *Bioorganic & Medicinal Chemistry*, 5(12): 2245-2249 (1997).
Watanabe et al., *The Journal of Immunology*, 155: 2972-2983 (1995).
Wipf et al., *Organic Letters*, 8(15): 3375-3378 (2006).
Yang et al., *Angew. Chem. Int. Ed. Engl.*, 43: 3818-3822 (2004).
Japanese Patent Office, International Search Report in International Application No. PCT/JP2009/065963 (Nov. 10, 2009).

* cited by examiner

ESTERIFIED α-GALACTOSYLCERAMIDE

TECHNICAL FIELD

The present invention relates to novel esterified α-galactosylceramides and use thereof.

BACKGROUND ART

The immune system has an elaborated surveillance function to distinguish normal cells from abnormal cells in the body, and remove only the abnormal cells. Once the surveillance function collapses, however, abnormal cells produced by mutation and the like cannot be removed but are allowed to proliferate in the body. A mass of these proliferated abnormal cells is a tumor, i.e., cancer.

Cancer is mainly treated by a method of surgically removing cancer or a method including use of anti-cancer agents. However, these treatment methods place a physical burden caused by removal surgery or side effects of anti-cancer agents, as well as a mental burden due to operative scars.

In such background, a treatment method using an immunotherapy in combination is drawing attention. In the immunotherapy, the number of immunocytes of patients is increased, and let the activated immunocytes attack cancer cells. If the immunity therapy succeeds in reducing the size of the cancer, the physical burden caused by the removal surgery thereafter becomes small. In addition, since the operative scar is small, the mental burden is drastically reduced.

Natural killer (NK) T cells are immunocytes belonging to a novel lymphocyte lineage showing characteristics different from those of other lymphocyte lineage cells (T, B, NK cells) which has been known ever. Since cytotoxic perforin granules are present in NKT cells, they are analogous to NK cells (non-patent document 1). However, since NKT cells express not only NK cell marker but also T cell receptor (TCR), they form a definitively different from the other lymphocyte lineage cells, new cell (non-patent document 2). NKT cells can produce both Th-1 type cytokine (mainly interferon (IFN)-γ) produced by helper T (Th)-1 cell that promotes immunostimulatory action and Th-2 type cytokine (mainly interleukin (IL)-4) produced by Th-2 cell that promotes immunosuppressive action (non-patent document 3), which suggests a possibility of controlling the balance of immune system (non-patent document 4). Therefore, by an immunotherapy of controlling the function of NKT cells, disrupted balance of the immune system is controlled and the surveillance function is enhanced, whereby cancer can be treated.

The most noticeable characteristic of NKT cells is that the α chain of TCR expressed by NKT cells is common to all members of one species. In other words, this means that all NKT cells of the living organisms belonging to the same species are activated by the same substance. This α chain is Vα24 in human and Vα14 in mouse, and they show extremely high homology between the two species. In addition, only very limited kinds of β chain are known to form a pair with the α chain. For this reason, this TCR is also called a "non-variable TCR".

There are various kinds of glycosphingolipids which are known to be present in the body. In glycosphingolipids in the body, various sugars generally form a β-bond with ceramide. While the existent amount thereof varies depending on the organ, they are present in the cellular membrane of various organs (non-patent document 5).

In the meantime, a report is known that glycosphingolipids wherein sugar forms an α-bond with ceramide has a strong immunostimulatory action and an antitumor activity. α-Galactosylceramide represented by Agelasphins is a glycolipid isolated from an extract of Agelas mauritianus, one kind of sponge, and has been reported to strongly activate NKT cells (non-patent document 6). α-Galactosylceramide is a sphingoglycolipid wherein galactose is bound by α-configuration to a ceramide formed by acylation of a sphingosine base by a long chain fatty acid.

After intake by antigen presenting cell (APC), which is represented by dendritic cell (DC) and the like, α-galactosylceramide is presented on the cellular membrane by a CD1d protein similar to major histocompatible complex (MHC) class I molecule. NKT cells are activated by recognition using TCR of the thus-presented complex of CD1d protein and α-galactosylceramide, which triggers various immune reactions.

Various analogs of α-galactosylceramide have been synthesized heretofore, and the correlation between the structures and activities thereof has been investigated. It has been clarified that, in a series of synthetic analogs, KRN7000 developed by Kirin Brewery Company, Limited, which is represented by the formula:

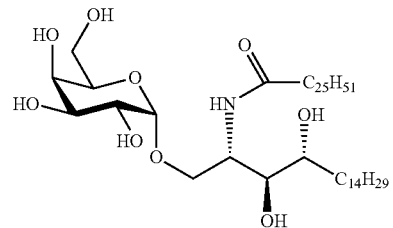

(hereinafter to be referred to as "α-GalCer") induces the strongest activity, and further, that the corresponding β-configuration (β-GalCer) does not show an immunostimulatory activity (non-patent document 7).

Taking note of such function of NKT cells, therapeutic drugs containing α-GalCer as an active ingredient have been proposed or developed in recent years. However, NKT cells activated by the administration of α-GalCer simultaneously produce, along with the production of IFN-γ, which is a cytokine that induces an immunostimulatory activity and is useful for cancer treatment, IL-4, which is a cytokine that induces an immunosuppressive action. Consequently, problems occur in that the both activities are offset, and the effect for a cancer treatment is not sufficient.

As mentioned above, a glycolipid represented by the formula:

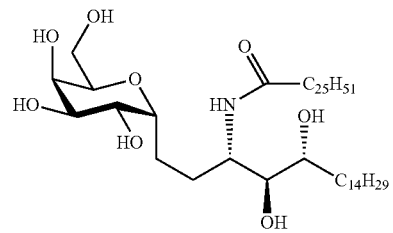

(hereinafter to be referred to as α-C-GalCer) that allows preferential production of IFN-γ, which is a cytokine that induces immunostimulatory activity against NKT cells, has been developed (non-patent documents 8-10, patent documents 1-3). α-C-GalCer is an analog wherein the oxygen atom at the binding site between the sugar and ceramide in α-GalCer is substituted by a methylene group. It has been found that the in vivo stability is enhanced and the efficacy is maintained for a long time since, in α-C-GalCer, the bond between sugar and ceramide is converted from a glycosyl bond to a carbon-carbon bond (non-patent document 11). However, α-C-GalCer is difficult for clinical application, since it leads only a very weak activity on human NKT cells in vitro.

On the other hand, of the present inventors, TASHIRO et al. independently found that a glycolipid having a carbasugar represented by the formula:

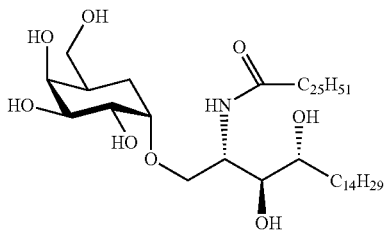

strongly induces IFN-γ production by NKT cells (non-patent document 12, patent document 6). In addition, since the glycolipid also induces a strong activity in the human system (in vitro), its clinical application is expected. However, since synthesis of the glycolipid requires many steps, the development of a novel analog has been still desired.

Glycolipids having an amide bond in the ceramide moiety have also been disclosed in patent documents 4 and 5, and non-patent documents 13-16.

DOCUMENT LIST

Patent Documents patent document 1: US 2005/0222048 A
patent document 2: WO 2003/105769
patent document 3: DE 10128250 A
patent document 4: WO 94/09020
patent document 5: US 2007/0238673 A
patent document 6: WO 2008/102888

Non-Patent Documents non-patent document 1: Proc. Natl. Acad. Sci. USA 1998, 95, 5690-5693
non-patent document 2: J. Immunol. 1995, 155, 2972-2983
non-patent document 3: J. Immunol. 1998, 161, 3271-3281
non-patent document 4: Nat. Immunol. 2003, 4, 1164-1165
non-patent document 5: Biochim. Biophys. Acta 1973, 315-335
non-patent document 6: Science, 1997, 278, 1626-1629
non-patent document 7: J. Med. Chem. 1995, 38, 2176-2187
non-patent document 8: Angew. Chem. Int. Ed. Engl. 2004, 43, 3818-3822
non-patent document 9: Org. Lett. 2006, 8, 3375-3378
non-patent document 10: Org. Lett. 2004, 6, 4077-4080
non-patent document 11: J. Exp. Med. 2003, 198, 1631-1641
non-patent document 12: Tetrahedron Lett. 2007, 48, 3343-3347
non-patent document 13: Biol. Pharm. Bull. 1995, 18, 1487-1491
non-patent document 14: Bioorg. Med. Chem. 1997, 5, 2245-2249
non-patent document 15: Bioorg. Med. Chem. 1998, 6, 1905-1910
non-patent document 16: Tetrahedron 2005, 61, 1855-1862

SUMMARY OF THE INVENTION

Problems to be Solved by the Invention

The present invention has been made in view of such situation, and is provision of a novel glycolipid effective for cancer treatment. The present invention also aims to provide a medicament such as an anti-cancer agent containing the novel glycolipid and the like.

Means of Solving the Problems

The present inventors have conducted studies in an attempt to solve the above-mentioned problems, and found that a compound wherein an amide bond in the ceramide moiety at the galactose α-anomeric position, which is a part of the general skeleton of galactosylceramide (one kind of glycolipid), is converted to an ester bond selectively induces production of IFN-γ. The present inventors have further studied in detail, and found that a specific immunostimulatory activity is expressed by the selective production of the IFN-γ, which is extremely effective for cancer treatment. The present inventors have made further studies and completed the present invention.

The present invention provides the following.

[1] A compound represented by the formula (I):

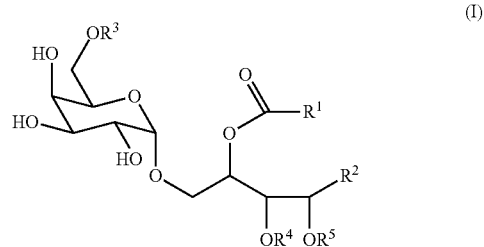

wherein $R^1$ is a hydrocarbon group having a carbon number of 1 to 30, $R^2$ is a hydrocarbon group having a carbon number of 1 to 20, $R^3$ is a hydrogen atom or hydrocarbon group having a carbon number of 1 to 5, $R^4$ and $R^5$ are the same or different and each is a hydrogen atom or a hydrocarbon group having a carbon number of 1 to 5, or $R^4$ and $R^5$ in combination form a divalent hydrocarbon group having a carbon number of 1 to 5, and optionally form a ring structure together with the adjacent ethylenedioxy, (hereinafter to be referred to as compound (I)) or a salt thereof.

[2] The compound of the above-mentioned [1], wherein $R^1$ is an alkyl group having a carbon number of 1 to 30, an alkenyl group having a carbon number of 2 to 30, or an alkynyl group having a carbon number of 2 to 30, or a salt thereof.

[3] The compound of the above-mentioned [1], wherein $R^2$ is an alkyl group having a carbon number of 1 to 20, an alkenyl group having a carbon number of 2 to 20, or an alkynyl group having a carbon number of 2 to 20, or a salt thereof.

[4] The compound of the above-mentioned [1].

[5] A medicament comprising the compound of the above-mentioned [1], or a salt thereof.

[5'] A medicament comprising the compound of the above-mentioned [1], wherein $R^4$ and $R^5$ are each a hydrogen atom, or a salt thereof.
[6] An immunostimulator comprising the compound of the above-mentioned [1] or a salt thereof.
[6'] An immunostimulator comprising the compound of the above-mentioned [1], wherein $R^4$ and $R^5$ are each a hydrogen atom, or a salt thereof.
[7] A selective IFN-γ production inducer comprising the compound of the above-mentioned [1] or a salt thereof.
[7'] A selective IFN-γ production inducer comprising the compound of the above-mentioned [1], wherein $R^4$ and $R^5$ are each a hydrogen atom, or a salt thereof.
[8] An anti-cancer agent comprising the compound of the above-mentioned [1] or a salt thereof.
[8'] An anti-cancer agent comprising the compound of the above-mentioned [1], wherein $R^4$ and $R^5$ are each a hydrogen atom, or a salt thereof.
[9] A compound represented by the formula (II):

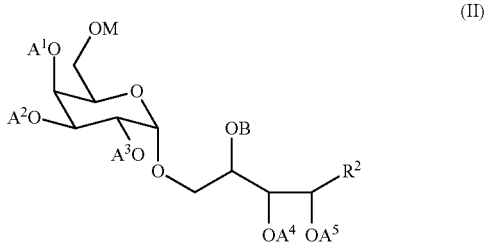

(II)

wherein $R^2$ is a hydrocarbon group having a carbon number of 1 to 20, M is a hydrocarbon group having a carbon number of 1 to 5 or A, A and $A^1$ are each a hydroxyl-protecting group, A and $A^1$ in combination optionally form a protecting group, $A^2$ and $A^3$ are the same or different and each is a hydrogen atom or a hydroxyl-protecting group, $A^2$ and $A^3$ in combination optionally form a protecting group, $A^4$ is a hydroxyl-protecting group or $R^4$, $A^5$ is a hydroxyl-protecting group or $R^5$, $A^4$ and $A^5$ in combination optionally form a protecting group, $R^4$ and $R^5$ are the same or different and each is a hydrogen atom or a hydrocarbon group having a carbon number of 1 to 5, or $R^4$ and $R^5$ in combination optionally form a divalent hydrocarbon group having a carbon number of 1 to 5, and optionally form a ring structure together with the adjacent ethylenedioxy, B is a hydrogen atom, —CO—$R^1$ wherein $R^1$ is a hydrocarbon group having a carbon number of 1 to 30, or a hydroxyl-protecting group,
(hereinafter to be referred to as compound (II)), or a salt thereof.
[10] The compound of the above-mentioned [9], wherein B is a hydrogen atom or —CO—$R^1$ wherein $R^1$ is a hydrocarbon group having a carbon number of 1 to 30, or a salt thereof.
[11] A method of immunostimulation in a subject, comprising administering an effective amount of the compound of the above-mentioned [1] or a salt thereof to the subject.
[11'] A method of immunostimulation in a subject, comprising administering an effective amount of the compound of the above-mentioned [1], wherein $R^4$ and $R^5$ are each a hydrogen atom, or a salt thereof to the subject.
[12] A method of inducing a selective IFN-γ production in a subject, comprising administering an effective amount of the compound of the above-mentioned [1] or a salt thereof
to the subject.
[12'] A method of inducing a selective IFN-γ production in a subject, comprising administering an effective amount of the compound of the above-mentioned [1], wherein $R^4$ and $R^5$ are each a hydrogen atom, or a salt thereof to the subject.
[13] A method of treating cancer in a subject, comprising administering an effective amount of the compound of the above-mentioned [1] or a salt thereof to the subject.
[13'] A method of treating cancer in a subject, comprising administering an effective amount of the compound of the above-mentioned [1], wherein $R^4$ and $R^5$ are each a hydrogen atom, or a salt thereof to the subject.
[14] Use of the compound of the above-mentioned [1] or a salt thereof for the production of an immunostimulator.
[14'] Use of the compound of the above-mentioned [1], wherein $R^4$ and $R^5$ are each a hydrogen atom, or a salt thereof for the production of an immunostimulator.
[15] Use of the compound of the above-mentioned [1] or a salt thereof for the production of a selective IFN-γ production inducer.
[15'] Use of the compound of the above-mentioned [1], wherein $R^4$ and $R^5$ are each a hydrogen atom, or a salt thereof for the production of a selective IFN-γ production inducer.
[16] Use of the compound of the above-mentioned [1] or a salt thereof for the production of an anti-cancer agent.
[16'] Use of the compound of the above-mentioned [1], wherein $R^4$ and $R^5$ are each a hydrogen atom, or a salt thereof for the production of an anti-cancer agent.
[17] A commercial package comprising a composition comprising the compound of the above-mentioned [1] or a salt thereof, and a written matter describing that the composition can or should be used for immunostimulation, induction of selective IFN-γ production or cancer treatment.
[17'] A commercial package comprising a composition comprising the compound of the above-mentioned [1], wherein $R^4$ and $R^5$ are each a hydrogen atom, or a salt thereof, and a written matter describing that the composition can or should be used for immunostimulation, induction of selective IFN-γ production or cancer treatment.

Effect of the Invention

Compound (I) of the present invention or a salt thereof induced IFN-γ production equivalent to or not less than that by α-GalCer, and on the other hand, reduced IL-4 production. Therefore, it is considered that compound (I) of the present invention or a salt thereof forms a complex with Cd1d protein of an antigen presenting cell (APC), the complex is presented to NKT cells, and NKT cells recognize the complex via a T cell receptor (TCR) and preferentially produce IFN-γ from among the immunoregulating functions they have.

Thus, compound (I) of the present invention or a salt thereof can selectively produce IFN-γ, which is one kind of cytokine that activates the function of immunocytes, in a large amount.

Therefore, compound (I) or a salt thereof of the present invention is extremely useful for cancer treatment and effective since it does not cause any particularly noticeable side effects. Consequently, it can reduce physical and mental burdens on patients caused by conventional removal surgery of cancer and the like. In addition, it can also be used as a reagent for biological test and study.

Compound (II) or a salt thereof of the present invention is useful as a synthetic intermediate for compound (I) or a salt thereof. Of compounds (I) of the present invention or a salt thereof, a compound wherein $R^4$ and $R^5$ in combination form a divalent hydrocarbon group having a carbon number of 1 to 5, and form a ring structure together with the adjacent ethylenedioxy (e.g., compounds 32 and 22' described in Examples etc.) is also useful as a synthetic intermediate for compound (I) wherein $R^4$ and $R^5$ are each a hydrogen atom or a salt thereof.

DESCRIPTION OF EMBODIMENTS

Figure 1:
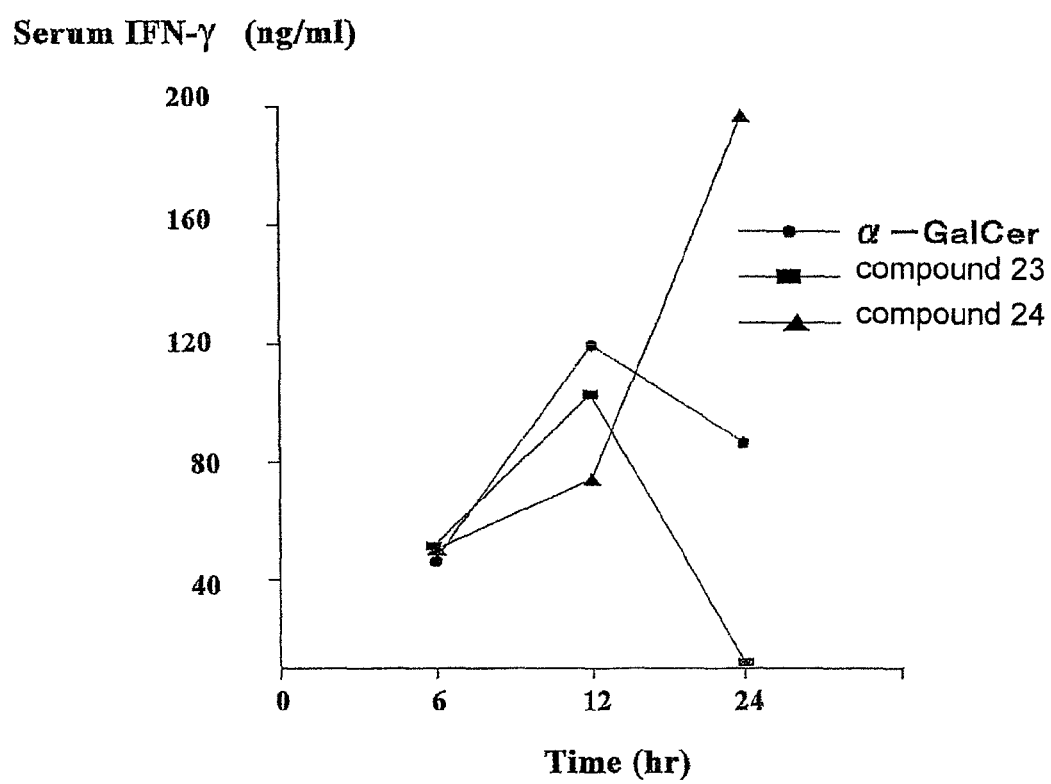
FIG. 1 shows the concentration of IFN-γ in the serum after lapse of indicated time from the administration of synthetic glycolipid (compounds 23 and 24) to mouse in vivo.

The present invention is explained in detail in the following by referring to a preferable embodiment thereof.

First, the definitions of the symbols used in the formulas in the present specification are explained.

$R^1$ is a hydrocarbon group having a carbon number of 1 to 30. The "hydrocarbon group having a carbon number of 1 to 30" is a concept also encompassing an alkyl group having a carbon number of 1 to 30, an alkenyl group having a carbon number of 2 to 30, an alkynyl group having a carbon number of 2 to 30, a cycloalkyl group having a carbon number of 3 to 30, a cycloalkenyl group having a carbon number of 3 to 30, and an aryl group having a carbon number of 6 to 30, which may be in any of linear, branched and cyclic forms, may be a saturated hydrocarbon group or an unsaturated hydrocarbon group, and may have an unsaturated bond in a molecule or at a terminal. Of these, as $R^1$, an alkyl group having a carbon number of 10 to 30 is preferable, and an alkyl group having a carbon number of 20 to 25 is more preferable. Specific examples of $R^1$ include —$C_{25}H_{51}$, —$C_{24}H_{49}$, —$C_{23}H_{47}$ and the like.

$R^2$ is a hydrocarbon group having a carbon number of 1 to 20. The "hydrocarbon group having a carbon number of 1 to 20" is a concept also encompassing an alkyl group having a carbon number of 1 to 20, an alkenyl group having a carbon number of 2 to 20, an alkynyl group having a carbon number of 2 to 20, a cycloalkyl group having a carbon number of 3 to 20, a cycloalkenyl group having a carbon number of 3 to 20 and an aryl group having a carbon number of 6 to 20, may be in any of linear, branched and cyclic forms, may be a saturated hydrocarbon group or an unsaturated hydrocarbon group, and may have an unsaturated bond in a molecule or at a terminal. Of these, as $R^2$, an alkyl group having a carbon number of 10 to 15, an alkenyl group having a carbon number of 10 to 15, or an alkynyl group having a carbon number of 10 to 15 is preferable, and an alkyl group having a carbon number of 12 to 14, an alkenyl group having a carbon number of 12 to 14, or an alkynyl group having a carbon number of 12 to 14 is more preferable. Specific examples of $R^2$ include —$C_6H_{12}$—C≡C—$C_6H_{13}$, —$C_{14}H_{29}$, —$C_6H_{12}$—CH=CH—$C_6H_{13}$, —$C_{13}H_{27}$, —$C_{12}H_{25}$, —CH=CH—$C_{12}H_{25}$ and the like.

The hydrocarbon group for $R^1$ or $R^2$ may have a substituent. That is, a compound wherein the hydrocarbon group for $R^1$ or $R^2$ is substituted or unsubstituted is also encompassed in compounds (I) and (II) of the present invention. When the hydrocarbon group for $R^1$ or $R^2$ has a substituent, examples of the substituent include a halogen atom (preferably chlorine atom, fluorine atom); an alkoxy group (preferably $C_{1-24}$, more preferably $C_{1-16}$, still more preferably $C_{1-10}$, particularly preferably $C_{1-4}$) such as a methoxy group, an ethoxy group, a propoxy group, an isopropoxy group, a butoxy group, a tert-butoxy group and the like; an aryloxy group (preferably $C_{6-14}$) such as a phenoxy group and the like; a hydroxyl group; an amino group; an alkylamino group such as a methylamino group, a dimethylamino group, an ethylamino group, a diethylamino group and the like; a cycloalkylamino group; an alkylcarbonylamino group such as an acetamide group and the like; a cycloalkylcarbonylamino group; an electron-donating group [arylcarbonylamino group such as benzoylamino group and the like (preferably, an arylcarbonylamino group wherein the aryl moiety is an aryl group having a carbon number of 6-14) and the like], further, a carboxyl group; an alkoxycarbonyl group; an acyl group (acyl group is as mentioned below, preferably an alkyl-carbonyl group wherein the alkyl moiety is a straight chain or branched alkyl group having a carbon number of 1 to 24); a carbamoyl group; an electron-withdrawing group such as a trifluoromethyl group and the like. The position and number of the substituent are not particularly limited, and 1 to substitutable maximum number of substituents may be present at substitutable position(s).

The "acyl group" in the present specification is, for example, a formyl group; an alkyl-carbonyl group (e.g., an alkyl-carbonyl group wherein the alkyl moiety is a straight chain or branched alkyl group having a carbon number of 1 to 24 (preferably 1 to 12) (e.g., acetyl group, propionyl group, butyryl group, isobutyryl group, valeryl group, pivaloyl group, hexanoyl group)); a cycloalkyl-carbonyl group (e.g., a cycloalkyl-carbonyl group wherein the cycloalkyl moiety is a cycloalkyl group having a carbon number of 3 to 10); an alkenyl-carbonyl group (e.g., an alkenyl-carbonyl group wherein the alkenyl moiety is a straight chain or branched alkenyl group having a carbon number of 2 to 12 (e.g., acryloyl group, methacryloyl group)); an aryl-carbonyl group (e.g., an aryl-carbonyl group wherein the aryl moiety is an aryl group having a carbon number of 6 to 14 (e.g., benzoyl group, naphthoyl group)) and the like. The aryl group of the aryl-carbonyl group is, for example, a monocyclic-tricyclic aromatic hydrocarbon group, and specific examples include a phenyl group, a naphthyl group, an anthryl group and a phenanthryl group. Of these, as the acyl group, a formyl group, an acetyl group, a propionyl group, a butyryl group, an isobutyryl group, a benzoyl group, a naphthoyl group and the like are preferable, and an acetyl group and a benzoyl group are more preferable.

Examples of the alkyl moiety of the above-mentioned alkylamino group and alkylcarbonylamino group include a straight chain or branched alkyl group (preferable carbon number 1-24, more preferable carbon number 1-16, still more preferable carbon number 1-10, particularly preferable carbon number 1-4) such as a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group and the like.

Examples of the cycloalkyl moiety of the above-mentioned cycloalkylamino group and cycloalkylcarbonylamino group include a cycloalkyl group (preferable carbon number 3-24, more preferable carbon number 3-16, still more preferable carbon number 3-10, particularly preferable carbon number 3-6) such as a cyclopentyl group, a cyclohexyl group and the like.

Examples of the alkoxy moiety of the above-mentioned alkoxycarbonyl group include those similar to the above-mentioned alkoxy group.

The above-mentioned substituents may be further substituted at substitutable position(s) by at least one kind from halogen, an alkyl group, a cycloalkyl group, an alkenyl group, an alkynyl group, a phenyl group, an alkoxy group, a hydroxyl group, an amino group, an alkylamino group and a cycloalkylamino group.

Examples of the halogen, alkoxy group, alkylamino group and cycloalkylamino group include those similar to the above.

Examples of the alkyl group include an alkyl group (preferable carbon number 1-24, more preferable carbon number 1-16, still more preferable carbon number 1-10, particularly preferable carbon number 1-4) such as a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group and the like.

Examples of the cycloalkyl group include a cycloalkyl group (preferable carbon number 3-24, more preferable carbon number 3-16, still more preferable carbon number 3-10, particularly preferable carbon number 3-6) such as a cyclopentyl group, a cyclohexyl group and the like.

Examples of the alkenyl group include an alkenyl group (preferable carbon number 2-24, more preferable carbon number 2-16, still more preferable carbon number 2-10, particularly preferable carbon number 2-4) such as a vinyl group, a propenyl group, a butenyl group and the like.

Examples of the alkynyl group include an alkynyl group (preferable carbon number 2-24, more preferable carbon number 2-16, still more preferable carbon number 2-10, particularly preferable carbon number 2-4) such as an ethynyl group, a propargyl group, a butynyl group, a pentynyl group and the like.

$R^3$ is a hydrogen atom or a hydrocarbon group having a carbon number of 1 to 5. The "hydrocarbon group having a carbon number of 1 to 5" is a concept also encompassing an alkyl group having a carbon number of 1 to 5, an alkenyl group having a carbon number of 2 to 5, an alkynyl group having a carbon number of 2 to 5, a cycloalkyl group having a carbon number of 3 to 5, and a cycloalkenyl group having a carbon number of 3 to 5, may be in any of linear, branched and cyclic forms, may be a saturated hydrocarbon group or an unsaturated hydrocarbon group, and may have an unsaturated bond in a molecule or at a terminal. Of these, as $R^3$, an alkyl group having a carbon number of 1 to 5 is preferable. Specific examples of $R^3$ include a methyl group, an ethyl group, a propyl group, a cyclopropyl group, a butyl group, a pentyl group and the like, and a methyl group and an ethyl group are specifically preferable. The hydrocarbon group for $R^3$ may have a substituent. That is, a compound wherein the hydrocarbon group for $R^3$ is substituted or unsubstituted is also encompassed in compound (I) of the present invention. When the hydrocarbon group for $R^3$ has a substituent, examples of the substituent include those similar to the substituents exemplified as the hydrocarbon group for the aforementioned $R^1$ and $R^2$. The substituent may be further substituted, and examples of the substituent include those similar to the substituents exemplified as the hydrocarbon group for the aforementioned $R^1$ and $R^2$.

M is a hydrocarbon group having a carbon number of 1 to 5 or A. The "hydrocarbon group having a carbon number of 1 to 5" is exemplified by those similar to the hydrocarbon group exemplified as the hydrocarbon group for the aforementioned $R^3$, and similar ones are preferable. A compound wherein the hydrocarbon group for M is substituted or unsubstituted is also encompassed in compound (II) of the present invention.

A and $A^1$ are hydroxyl-protecting groups, and A and $A^1$ in combination may form a protecting group. $A^2$ and $A^3$ are the same or different and each is a hydrogen atom or a hydroxyl-protecting group, and $A^2$ and $A^3$ in combination may form a protecting group. $A^4$ is a hydroxyl-protecting group or $R^4$, and $A^5$ is a hydroxyl-protecting group or $R^5$. $R^4$ and $R^5$ are as described above. When $A^4$ and $A^5$ are hydroxyl-protecting groups, $A^4$ and $A^5$ in combination may form a protecting group. Examples of the hydroxyl-protecting group for A, $A^1$, $A^2$, $A^3$, $A^4$ or $A^5$ include benzyl, 4-methoxybenzyl (i.e., p-methoxybenzyl (PMB)), methoxyethoxymethyl, tetrahydropyranyl, trimethylsilyl (TMS), t-butyldimethylsilyl (TBDMS), t-butyldiphenylsilyl (TBDPS), t-butoxycarbonyl, trichloroethoxycarbonyl, acetyl, pivaloyl and the like. Examples of the protecting group formed by each combination of A and $A^1$, $A^2$ and $A^3$, and $A^4$ and $A^5$ include benzylidene, p-methoxybenzylidene, isopropylidene and the like.

B is a hydrogen atom, —CO—$R^1$ wherein $R^1$ is a hydrocarbon group having a carbon number of 1 to 30, or a hydroxyl-protecting group.

Examples of the "hydrocarbon group having a carbon number of 1 to 30" include those similar to the groups exemplified as the hydrocarbon group having a carbon number of 1 to 30 for the aforementioned $R^1$, and similar ones are preferable.

Examples of the "hydroxyl-protecting group" include those similar to the groups exemplified as the hydroxyl-protecting group for the aforementioned A, $A^1$, $A^2$, $A^3$, $A^4$ or $A^5$, and similar ones are preferable.

In the present invention, the α configuration is employed from among the stereoisomers derived from the cyclic structure of sugar (galactopyranose).

When compound (I) and compound (II) has a stereoisomer derived from a structure other than the cyclic structure of sugar (e.g., asymmetric carbon of a part other than the cyclic structure of sugar etc.), any isomer is also encompassed in the present invention, which may be a mixture (including racemate) of two or more kinds of isomers at any ratio.

Particularly, compound (I) contains an optical isomer derived from a part other than the cyclic structure of sugar. In the present invention, it may be a single optically active form, or a mixture (including racemate) of two or more kinds of optically active forms at any ratio. An asymmetric carbon to which —O—$COR^1$ is bonded is preferably S configuration. The asymmetric carbon having —$COR^4$ which is adjacent to the asymmetric carbon to which —O—$COR^1$ is bonded is preferably R configuration. The asymmetric carbon to which $R^2$ is bonded is preferably R configuration.

Compound (II) contains an optical isomer derived from the asymmetric carbon of a part other than the cyclic structure of sugar. In the present invention, it may be a single optically active form, or a mixture (including racemate) of two or more kinds of optically active forms at any ratio. The asymmetric carbon to which —OB is bonded is preferably S configuration. The asymmetric carbon having —$OA^4$ which is adjacent to the asymmetric carbon to which —OB is bonded is preferably R configuration. The asymmetric carbon to which $R^2$ is bonded is preferably R configuration.

As compound (I),

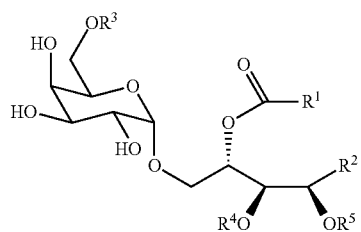

wherein each symbol is as defined above, and the like can be mentioned.

As compound (II),

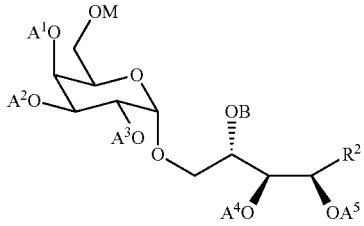

wherein each symbol is as defined above, and the like can be mentioned.

The salts of compound (I) and compound (II) are preferably pharmacologically acceptable salts. Examples thereof include inorganic acid salts such as hydrochloride, hydrobromide, hydroiodide, sulfate, nitrate, phosphate and the like; organic acid salts such as succinate, fumarate, acetate, methanesulfonate, toluenesulfonate and the like; alkali metal salts such as sodium salt, potassium salt and the like; alkaline earth metal salts such as magnesium salt, calcium salt and the like; ammonium salts such as ammonium salt, alkylammonium salt and the like.

Examples of compound (I) or a salt thereof include, but are not limited to, the compounds described in Examples 23, 24, 32, 33 and 22'.

Examples of compound (II) or a salt thereof include, but are not limited to, the compounds described in Examples 20, 21, 22, 30, 31, 38, 39, 40, 45, 46 and 47.

Now, preferable embodiments of the production methods of compounds (I) and (II) of the present invention are explained.

The compounds of the present invention can be produced by various methods known per se and, for example, compounds (I) and (II) can be produced according to the method described in the following Scheme 1 or a method analogous thereto. Compounds (xx), (xxi) and the below-mentioned compounds (xxii) and (xx''') are encompassed in compound (II) of the present invention.

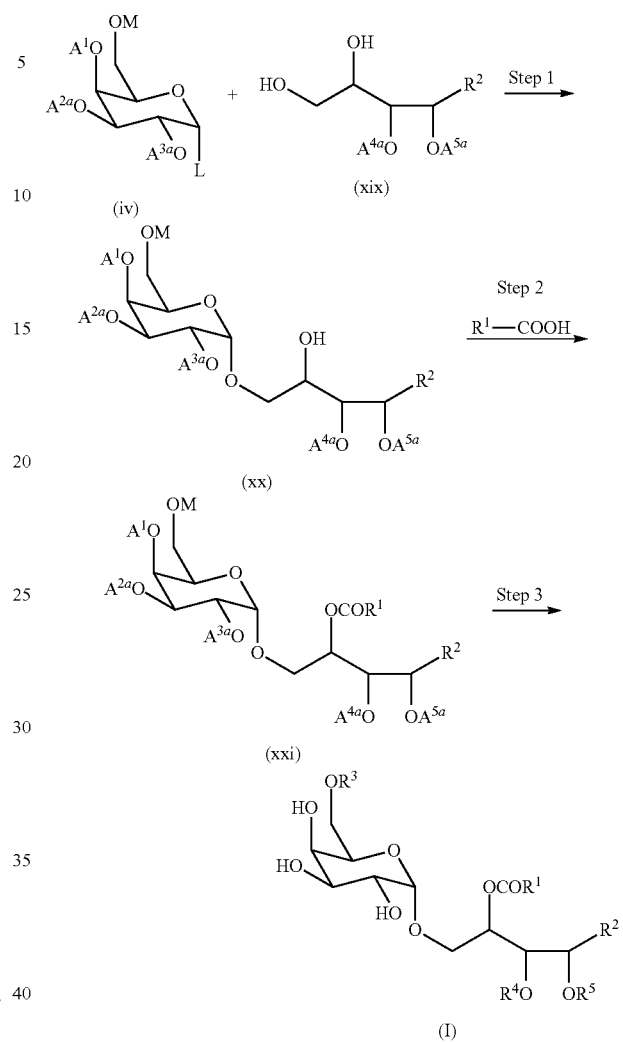

wherein L is a leaving group, $A^{2a}$ and $A^{3a}$ are hydroxyl-protecting groups, $A^{2a}$ and $A^{3a}$ in combination may form a protecting group, $A^{4a}$ is a hydroxyl-protecting group or $R^{4a}$, $A^{5a}$ is a hydroxyl-protecting group or $R^{5a}$, when $A^{4a}$ and $A^{5a}$ are hydroxyl-protecting groups, then $A^{4a}$ and $A^{5a}$ in combination may form a protecting group, $R^{4a}$ and $R^{5a}$ are each a hydrocarbon group having a carbon number of 1-5, or $R^{4a}$ and $R^{5a}$ in combination form a divalent hydrocarbon group having a carbon number of 1-5 and optionally form a ring structure with the adjacent ethylenedioxy, and each of other symbols is as defined above.

Examples of the leaving group for L include trichloroacetoimidoyloxy, phosphoric acid ester [—OP(O)(OPh)$_2$ and the like], halogen (Br, F and the like) and the like.

Examples of the hydroxyl-protecting group for $A^{2a}$ or $A^{3a}$, and hydroxyl-protecting group formed by $A^{2a}$ and $A^{3a}$ in combination include those similar to the aforementioned groups for $A^2$ and $A^3$. Examples of the hydroxyl-protecting group for $A^{4a}$ or $A^{5a}$, and hydroxyl-protecting group formed by $A^{4a}$ and $A^{5a}$ in combination include those similar to the aforementioned groups for $A^4$ and $A^5$. Examples of the abovementioned hydrocarbon group for $R^{4a}$ or $R^{5a}$, and the abovementioned divalent hydrocarbon group formed by $R^{4a}$ and $R^{5a}$ in combination include those similar to the aforementioned groups for $R^4$ and $R^5$.

In step 1, compound (iv) and compound (xix) are reacted in the presence of silver trifluoromethanesulfonate and molecular sieve to give compound (xx).

The amount of compound (iv) to be used is generally 0.1-10 equivalents relative to compound (xix). The amount of silver trifluoromethanesulfonate to be used is generally 0.1-3 equivalents relative to compound (iv). The amount of the molecular sieve to be used is generally 1-2 g per 1 mmol of compound (iv). Examples of the solvent include dichloromethane, trichloromethane, THF, dioxane, ethyl acetate and the like. The amount of the solvent to be used is generally 1-100 ml per 1 mmol of compound (iv). The reaction temperature is generally −40° C.-room temperature, and the reaction time is generally 0.1-24 hr.

Compound (xx) can be isolated by a conventional method. For example, compound (xx) can be isolated by diluting the reaction mixture with a solvent, washing the mixture with saturated aqueous sodium hydrogen carbonate and saturated brine, and drying same over magnesium sulfate, which is followed by filtration and concentration. Where necessary, the compound may be further purified.

The β-form present in the resultant product can be separated from compound (xx) by eluting with, for example, hexane-ethyl acetate (3:1, then 2:1).

Step 1 can also be performed using compound (iii) in the following scheme 2 instead of compound (iv). That is,
(1) compound (iii) in the following scheme 2 and $Cl_3CCN$ are imidated in a solvent in the presence of a base, and
(2) the imidate compound and compound (xix) are reacted in a solvent in the presence of silver trifluoromethanesulfonate and molecular sieve to give compound (xx).

In the above-mentioned (1), the amount of $Cl_3CCN$ to be used is generally 5-10 equivalents relative to compound (iii). Examples of the solvent include dichloromethane, diethyl ether, THF and the like. The amount of the solvent to be used is generally 5-10 ml per 1 mmol of compound (iii). Examples of the base include cesium carbonate, diazabicycloundecene (DBU), diazabicyclononene (DBN) and the like. The amount of the base to be used is generally 0.1-2 equivalents relative to compound (iii). The reaction temperature is generally 0-30° C., and the reaction time is generally 15 min-24 hr.

In the above-mentioned (2), the amount of compound (xix) to be used is generally 0.8-1.5 equivalents relative to the imidate compound. The amount of silver trifluoromethanesulfonate to be used is generally 0.1-2 equivalents relative to the imidate compound. The amount of the molecular sieve to be used is generally 1-2 g per 1 mmol of the imidate compound. Examples of the solvent include dichloromethane, trichloromethane, THF, dioxane, ethyl acetate and the like. The amount of the solvent to be used is generally 5-50 ml per 1 mmol of the imidate compound. The reaction temperature is generally 0-30° C. and the reaction time is generally 0.5-20 hr.

In step 2, compound (xx) and $R^1$—COOH are reacted in the presence of a condensing agent and a base to give compound (xxi).

The amount of $R^1$—COOH to be used is generally 0.9-10 equivalents relative to the compound (xx). Examples of the condensing agent include 1-[3-(dimethylamino)propyl]-3-ethylcarbodiimide (WSC) hydrochloride, dicyclohexylcarbodiimide and the like. The amount of the condensing agent to be used is generally 1-5 equivalents relative to $R^1$—COOH. Examples of the base include 4-(dimethylamino)pyridine (DMAP), diisopropylethylamine, DABCO and the like. The amount of the base to be used is generally 1.2-10 equivalents relative to 1-[3-(dimethylamino)propyl]-3-ethylcarbodiimide (WSC) hydrochloride. Examples of the solvent include tetrahydrofuran (THF), dichloromethane, trichloromethane, benzene, hexane, ethyl acetate, a mixed solvent thereof (e.g., tetrahydrofuran-dichloromethane (1:1)) and the like. The amount of the solvent to be used is generally 10-1000 ml per 1 g of $R^1$—COOH. The reaction temperature is generally 0-60° C. and the reaction time is generally 5 min-5 days.

Compound (xxi) can be isolated by a conventional method. For example, compound (xxi) can be isolated by diluting the reaction mixture with a solvent, washing the mixture with water and saturated brine, and drying same over magnesium sulfate, which is followed by filtration and concentration. Where necessary, the compound may be further purified.

In step 3, hydroxyl-protecting group is removed from compound (xxi) to give compound (I).

As the removal method, a method known per se can be selected according to the kind of the protecting group.

For example, when $A^1$, $A^{2a}$ and $A^{3a}$ are benzyl groups, or $A^1$ and A for M in combination form benzylidene and $A^{2a}$ and $A^{3a}$ are benzyl groups, compound (I) can be obtained by removing A for M, $A^1$, $A^{2a}$ or $A^{3a}$ by hydrogenolysis in a solvent in the presence of a catalyst. Examples of the solvent include dichloromethane, trichloromethane, tetrahydrofuran, ethyl acetate, ethanol, methanol, a mixed solvent thereof and the like. The amount of the solvent to be used is generally 10-100 ml per 1 g of compound (xxi). As the catalyst, $Pd(OH)_2$ carbon, Pd carbon, Pd black and the like can be mentioned. The amount of the catalyst to be used is generally 50 mg-2 g per 1 g of the compound (xxi). The reaction temperature is generally 10-100° C. and the reaction time is generally 30 min-24 hr.

When $R^2$ of compound (xxi) is an unsaturated hydrocarbon group, the reaction may accompany an addition reaction, and compound (I) wherein $R^2$ is a saturated hydrocarbon group can also be obtained.

For example, when $A^{2a}$ and $A^{3a}$ are 4-methoxybenzyl, the following compound (xxii) can be obtained by removing $A^{2a}$ and $A^{3a}$ from compound (xxi) in a solvent in the presence of water by using 2,3-dichloro-5,6-dicyano-p-benzoquinone (DDQ). The amount of 2,3-dichloro-5,6-dicyano-p-benzoquinone (DDQ) to be used is generally 1-3 equivalents relative to the number of 4-methoxybenzyl group present in compound (xxi). Examples of the solvent include dichloromethane, trichloromethane, dioxane, THF, benzene, hexane, diethyl ether, water, a mixed solvent thereof (e.g., dichloromethane-water (10:1)) and the like. The amount of the solvent to be used is generally 10-100 ml per 1 g of the compound (xxi). The reaction temperature is generally 0.0-50° C. and the reaction time is generally 5 min-24 hr.

A compound obtained by removing $A^{2a}$ and $A^{3a}$ from compound (xxi) [i.e., a compound wherein —$OA^{2a}$ and —$OA^{3a}$ have been converted to —OH, which is represented by the following formula:

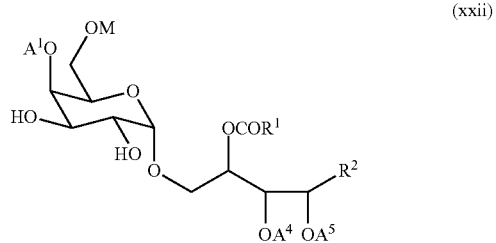

(xxii)

wherein each symbol is as defined above, hereinafter to be referred to as compound (xxii), can be isolated by a conventional method. For example, the compound can be isolated by diluting the reaction mixture with a solvent, washing the mixture with saturated aqueous sodium hydrogen carbonate and saturated brine, and drying same over magnesium sulfate, which is followed by filtration and concentration. Where necessary, the compound may be further purified.

The obtained compound (xxii) can be converted to compound (I) by further removing a hydroxyl-protecting group by a method known per se.

For example, in (xxii), $A^1$ and A for M, and $A^{4a}$ and $A^{5a}$ each form isopropylidene, compound (I) can be obtained by removing A for M, $A^1$, $A^{4a}$ and $A^{5a}$ from compound (xxii) in a solvent by using an acid. Examples of the acid include hydrofluoric acid, acetic acid, trifluoroacetic acid and the like. The amount of the acid to be used is generally 1-100 equivalents relative to compound (xxii). Examples of the solvent include water, acetonitrile (MeCN), dichloromethane, trichloromethane, a mixed solvent thereof and the like. The amount of the solvent to be used is generally 10-1000 ml per 1 g of the compound (xxii). The reaction temperature is generally −20-60° C. and the reaction time is generally 5 min-24 hr.

For example, in compound (xxii), when $A^1$ and A for M in combination form benzylidene, compound (I) can be obtained by removing A for M, and $A^1$ by hydrogenolysis in a solvent in the presence of a catalyst. Examples of the solvent include dichloromethane, trichloromethane, tetrahydrofuran, ethyl acetate, methanol, ethanol, a mixed solvent thereof and the like. The amount of the solvent to be used is generally 10-1000 ml per 1 g of the compound (xxii). As the catalyst, $Pd(OH)_2$ carbon, Pd carbon, Pd black and the like can be mentioned. The amount of the catalyst to be used is generally 5 mg-1 g per 1 g of the compound (xxii). The reaction temperature is generally −20-60° C. and the reaction time is generally 5 min-24 hr.

For example, in compound (xxii), when $A^1$ and A for M in combination form benzylidene, and $A^{4a}$ and $A^{5a}$ in combination form isopropylidene, compound (I) can be obtained by removing A for M, $A^1$, $A^{4a}$ and $A^{5a}$ from compound (xxii) by using an acid in a solvent. Examples of the acid include hydrofluoric acid, hydrochloric acid water, sulfuric acid water, acetic acid, trifluoroacetic acid and the like, with preference given to hydrofluoric acid, acetic acid, trifluoroacetic acid and the like. The amount of the acid to be used is generally 1-100 equivalents relative to the compound (xxii). Examples of the solvent include water, acetonitrile (MeCN), dichloromethane, trichloromethane, a mixed solvent thereof and the like. The amount of the solvent to be used is generally 10-1000 ml per 1 g of the compound (xxii). The reaction temperature is generally −20-60° C. and the reaction time is generally 5 min-24 hr.

Compound (I) can be isolated by a conventional method. For example, the compound can be isolated by diluting the reaction mixture with a solvent, washing the mixture with saturated aqueous sodium hydrogen carbonate and saturated brine, and drying same over magnesium sulfate, and subjecting the resulting product to filtration and concentration. Where necessary, the compound may be further purified.

When compound (I) wherein $R^2$ is an unsaturated hydrocarbon group such as alkynyl and the like is obtained by the above-mentioned method, compound (I) wherein $R^2$ is a saturated hydrocarbon group such as alkyl and the like can be obtained by reducing the unsaturated bond by a conventional method. For example, reduction can be performed using a catalyst in a solvent under a hydrogen atmosphere. As the catalyst, $Pd(OH)_2$ carbon, Pd carbon, Pd black and the like can be mentioned. The amount of the catalyst to be used is generally 5 mg-1 g per 1 g of the unsaturated hydrocarbon compound (I). Examples of the solvent include trichloromethane, methanol, ethanol, ethyl acetate, hexane, tetrahydrofuran, a mixed solvent thereof and the like. The amount of the solvent to be used is generally 1-1000 ml per 1 g of the unsaturated hydrocarbon compound (I). The reaction temperature is generally 0-80° C., preferably 10-80° C. and the reaction time is generally 5 min-3 days, preferably 5 min-24 hr.

Compound (I) wherein $R^2$ is a saturated hydrocarbon group can be isolated by a conventional method. For example, the reaction mixture is filtered to remove the catalyst, concentrated and, where necessary, purified, whereby compound (I) wherein $R^2$ is a saturated hydrocarbon group can be isolated.

When compound (I) wherein $R^4$ and $R^5$ in combination form a divalent hydrocarbon group having a carbon number of 1-5 (e.g., isopropylidene), and form, together with the adjacent ethylenedioxy, a ring structure (e.g., 2,2-dimethyl-1,3-dioxolane) is obtained by the above-mentioned method, deprotection can be performed by removing the divalent hydrocarbon group by using an acid in a solvent. Examples of the acid include hydrofluoric acid, acetic acid, trifluoroacetic acid and the like. The amount of the acid to be used is generally 1-100 equivalents relative to compound (I) with protected $R^4$ and $R^5$. Examples of the solvent include water, dichloromethane, acetonitrile, a mixed solvent thereof (e.g., dichloromethane-acetonitrile (1:1)) and the like. The amount of the solvent to be used is generally 10-1000 ml per 1 g of compound (I) with protected $R^4$ and $R^5$. The reaction temperature is generally 0-30° C. and the reaction time is generally 5 min-30 min.

Compound (I) with deprotected $R^4$ and $R^5$ can be isolated by a conventional method. For example, the reaction mixture is neutralized with aqueous sodium hydrogen carbonate, extracted with dichloromethane, and concentrated, whereby compound (I) with deprotected $R^4$ and $R^5$ can be obtained. Where necessary, compound (I) with deprotected $R^4$ and $R^5$ can also be isolated by purification by silica gel chromatography.

Compound (I) and compound (II) obtained as mentioned above can be converted to the object salts by a method known per se or a method analogous thereto.

Compound (iv) described in scheme 1 can be produced, for example, by a method shown in the following scheme 2.

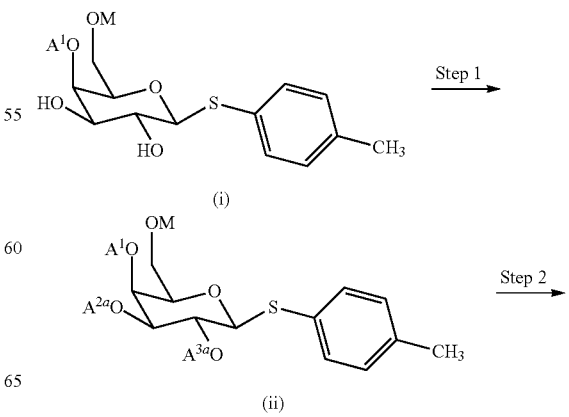

scheme 2

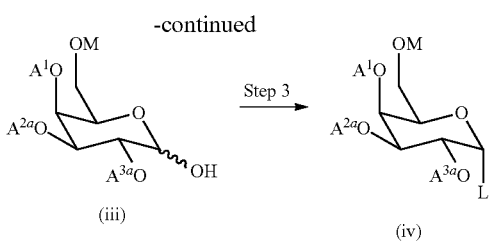

wherein each symbol is as defined above.

The starting compound (i) can be produced from penta-O-acetyl-β-D-galactopyranose as a starting material and by the method described in O. Plettenburg, V. Bodmer-Narkevitch and C-H. Wong, J. Org. Chem. 2002, 67, 4559-4564, and S. Roy, A. Chakraborty and R. Ghosh, Carbohydr. Res., 2008, 343, 2523-2529 or a method analogous thereto.

In step 1, the hydroxyl group of compound (i) is protected to give compound (ii). For example, when $A^{2a}$ and $A^{3a}$ are 4-methoxybenzyl, compound (ii) can be obtained by reacting compound (i) with 2-3 equivalents of 4-methoxybenzyl halide (e.g., 4-methoxybenzyl chloride) in the presence of a catalyst and a base.

As the base, sodium hydride, potassium hydride and n-BuLi can be mentioned. The amount of the base to be used is generally 2-3 equivalents relative to compound (i). In some cases, a catalyst may be added. Examples of the catalyst include quaternary ammonium salt (e.g., tetrabutylammonium iodide, tetrabutylammonium bromide etc.) and the like. The amount of the catalyst to be used is generally 0.001-0.1 equivalents relative to compound (i). Examples of the solvent include N,N-dimethylformamide (DMF), THF, HMPA, or a mixed solvent thereof and the like. The amount of the solvent to be used is generally 0.5-50 ml per 1 mmol of the compound (i). The reaction temperature is generally −20-100° C., and the reaction time is generally 10 min -24 hr.

Compound (ii) can be isolated by a conventional method. For example, ice is added to the reaction mixture, and the mixture is extracted with an organic solvent such as ethyl acetate and the like, washed with water and saturated brine, dried over magnesium sulfate, filtered and concentrated, whereby compound (ii) can be obtained. Where necessary, the compound may be further purified.

In step 2,4-methylphenylthio group is dissociated from compound (ii), and OH group is introduced to give compound (iii). For example, compound (ii) and a halogenating agent (e.g., N-bromosuccinimide (NBS)) are reacted in a solvent, and saturated aqueous sodium hydrogen carbonate and the like are added, whereby compound (iii) introduced with OH group can be obtained.

Examples of the halogenating agent include N-bromosuccinimide, iodine, bromine and the like. The amount of the halogenating agent to be used is generally 1-2 equivalents relative to compound (ii). Examples of the solvent include acetone, or a mixed solvent of acetone and THF, ethyl acetate or dichloromethane and the like. The amount of the solvent to be used is generally 0.5-100 ml, preferably 5-100 ml, per 1 mmol of compound (ii). The reaction temperature is generally −50° C. to 50° C., and the reaction time is generally 5 min-24 hr. While the amount of saturated aqueous sodium hydrogen carbonate to be used is not particularly limited, it is an amount capable of neutralizing an acidic substance generally produced.

When A for M and $A^1$ of compound (ii) in combination form a protecting group, the above-mentioned reaction may accompany a conversion reaction of the protecting group. For example, when A for M and $A^1$ of compound (ii) in combination form 4-methoxybenzylidene (protecting group), conversion of the protecting group to isopropylidene is performed along with the above-mentioned reaction, whereby compound (iii) wherein A for M and $A^1$ in combination form a protecting group isopropylidene can also be obtained.

Compound (iii) can be isolated by a conventional method. For example, the mixture is extracted with an organic solvent such as ethyl acetate and the like, washed with saturated aqueous sodium hydrogen carbonate and saturated brine, dried over magnesium sulfate, filtered and concentrated, whereby compound (iii) can be obtained. Where necessary, the compound may be further purified.

In step 3, the 1-position hydroxyl group of compound (iii) is converted to a leaving group L to give compound (iv). Examples of the leaving group L include trichloroacetoimidoyloxy, halogen (bromine, fluorine) and the like. For example, when the leaving group is trichloroacetoimidoyloxy, compound (iv) can be obtained by reacting compound (iii) with $Cl_3CCN$ in the presence of a base.

The amount of $Cl_3CCN$ to be used is generally 1-10 equivalents relative to compound (iii). Examples of the base include cesium carbonate, diazabicycloundecene (DBU), diazabicyclononene (DBN) and the like. The amount of the base to be used is generally 0.01-2 equivalents relative to compound (iii). Examples of the solvent include dichloromethane, diethyl ether, THF and the like. The amount of the solvent to be used is generally 0.5-100 ml per 1 mmol of compound (iii). The reaction temperature is generally 0-50° C., and the reaction time is generally 30 min-24 hr.

Compound (iv) can be isolated by a conventional method. For example, the mixture is diluted with a solvent, washed with water, saturated aqueous sodium hydrogen carbonate and saturated brine, dried over magnesium sulfate, filtered and concentrated, whereby compound (iv) can be obtained. Where necessary, the compound may be further purified.

When, in the reaction of the above-mentioned step 3, $OA^1$ and OM in compound (iii) in combination form a protecting group (e.g., benzylidene or isopropylidene) to take a cyclic structure, steric repulsion by the cyclic structure occurs at the 1-position anomeric position, and compound (iv) in an α-form can be preferentially obtained.

In the above-mentioned reaction, even when compound (iv) is obtained as an α,β-form (iv')

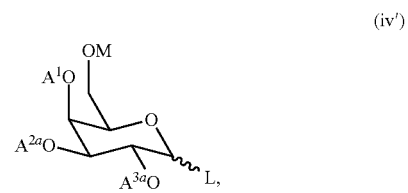

it can also be directly used for the reaction of scheme 1.

Of compound (iii), a compound wherein M is a hydrocarbon group having a carbon number of 1-5 (hereinafter to be referred to as compound (iii')) can also be produced by the method shown in scheme 3. The starting material compound (iii'a) can be produced by the method described in T. J. Lucas et al., Carbohydr. Res., 1975, 39, 39-45 or a method analogous thereto.

scheme 3

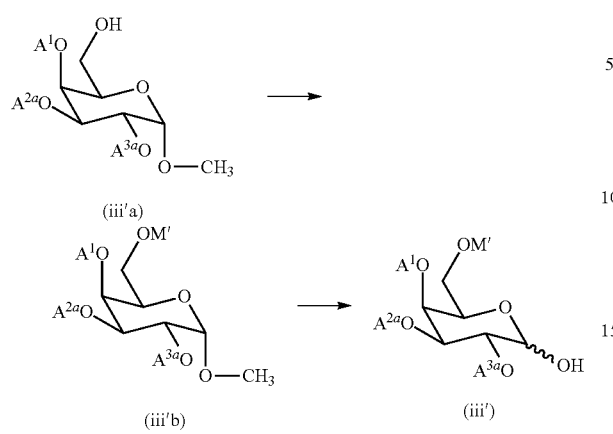

wherein M' is a hydrocarbon group having a carbon number of 1-5 (e.g., methyl), and each of other symbols is as defined above.

Compound (iii'b) can be obtained by reacting compound (iii'a) with alkyl halide in the presence of a base. Examples of the base include sodium hydride, n-butyllithium and the like. The amount of the base to be used is generally 1-3 equivalents relative to compound (iii'a). Examples of the alkyl halide include methyl iodide, ethyl iodide, propyl bromide and the like. The amount of the alkyl halide to be used is generally 1-3 equivalents relative to compound (iii'a).

Examples of the solvent include aprotic solvents such as N,N-dimethylformamide, ethers (e.g., diethyl ether, tetrahydrofuran) and the like, and a mixed solvent thereof. The amount of the solvent to be used is generally 10- to 20-fold volume relative to compound (iii'a).

The reaction temperature is generally 0 to 80° C., and the reaction time is generally 1-24 hr.

Compound (iii'b) can be isolated by a conventional method. For example, compound (iii'b) can be isolated by adding water to the reaction mixture, extracting the mixture with ethyl acetate, washing the organic layer with water and saturated brine, drying the layer over anhydrous magnesium sulfate, and filtering and concentrating the layer.

Compound (iii') can be obtained by directly reacting compound (iii'b) with an acid. Alternatively, compound (iii') can be obtained by leading compound (iii'b) to the corresponding O-acetyl form and performing alcoholysis of the form.

When O-acetyl form is used, for example, O-acetyl form is prepared by a treatment with a catalytic amount of an acid in acetic anhydride, and alcoholysis of the form is performed. Examples of the acid include concentrated sulfuric acid, concentrated hydrochloric acid, p-toluenesulfonic acid and the like. The amount of the acetic anhydride to be used is generally 5- to 20-fold volume relative to compound (iii'b). The reaction temperature is generally 0° C. to room temperature, and the reaction time is generally 5 min-1 hr. After neutralization, O-acetyl form can be obtained by concentration under reduced pressure.

The obtained O-acetyl form can be converted to an alcohol by a treatment with a base such as sodium methoxide, sodium hydroxide and the like in a solvent such as alcohol solvent (e.g., methanol, ethanol and the like).

Compound (iii') can be isolated by a conventional method and, for example, may be acidified with a cation exchange resin, and purified by filtration and concentration.

Compound (xix) described in scheme 1 can be produced, for example, by the method shown in the following scheme 4. Compound (xix') is encompassed in compound (xix).

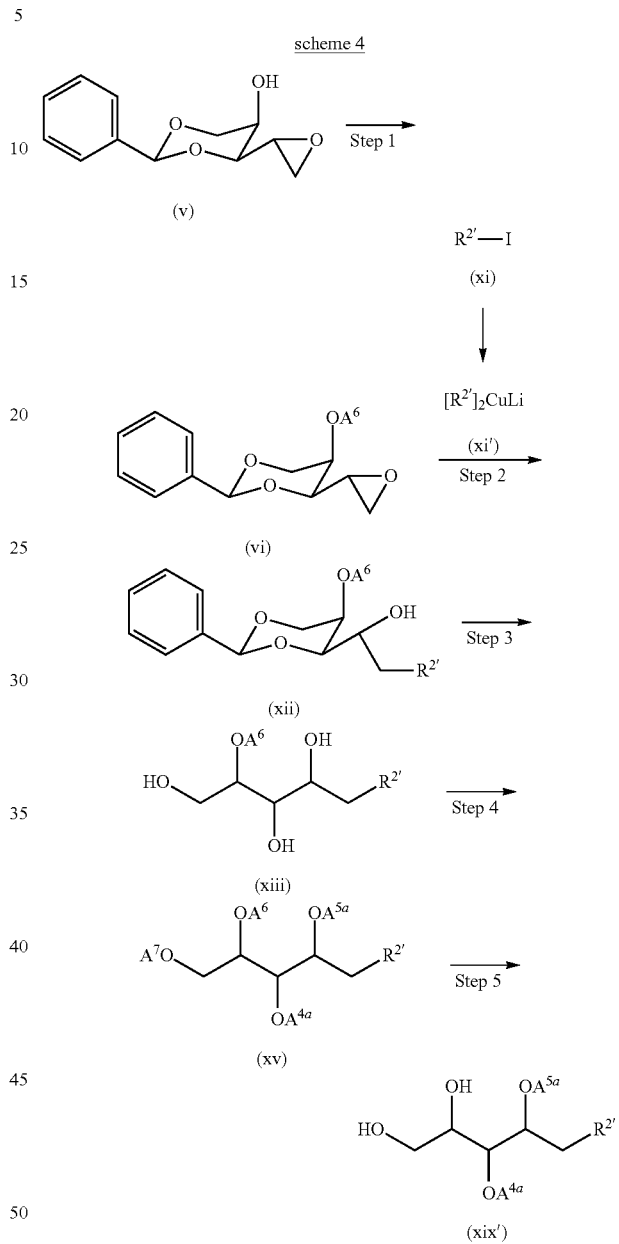

wherein $A^6$ and $A^7$ are hydroxyl-protecting groups, $R^{2'}$ is a hydrocarbon group having a carbon number of 1-19, and other symbols are as defined above.

The starting material compound (v) can be produced by the method described in K. Murata, T. Toba, K. Nakanishi, B. Takahashi, T. Yamamura, S. Miyake, and H. Annoura, J. Org. Chem. 2005, 70, 2398-2401 or a method analogous thereto.

Examples of the hydroxyl-protecting group for $A^6$ include 4-methoxybenzyl, benzyl, acetyl, benzyloxycarbonyl and the like. Examples of the hydroxyl-protecting group for $A^7$ include t-butyldimethylsilyl, TMS, t-butyldiphenylsilyl and the like. Examples of the "hydrocarbon group having a carbon number of 1-19" for $R^{2'}$ include those similar to the hydrocarbon groups exemplified as $R^2$ except hydrocarbon group having a carbon number of 20. In each formula in scheme 4, a group represented by —$CH_2$—$R^{2'}$ is encompassed in $R^2$.

In step 1, the hydroxyl group of compound (v) is protected to give compound (vi). For example, when $A^6$ is 4-methoxybenzyl, compound (v) is reacted with 4-methoxybenzyl halide (e.g., 4-methoxybenzyl chloride) in the presence of a base to give compound (vi).

The amount of 4-methoxybenzyl halide to be used is generally 1-2 equivalents relative to compound (v). Examples of the base include sodium hydride, potassium hydride, n-BuLi, DBU and the like. The amount of the base to be used is generally 1-2 equivalents relative to compound (v). Examples of the solvent include DMF, THF, HMPA and the like. The amount of the solvent to be used is generally 0.2-100 ml per 1 mmol of the compound (v). The reaction temperature is generally −20-100° C., and the reaction time is generally 30 min-24 hr.

Compound (vi) can be isolated by a conventional method. For example, ice is added to the reaction mixture, and the mixture is extracted with an organic solvent such as ethyl acetate and the like, washed with water and saturated brine, dried over magnesium sulfate, filtered and concentrated, whereby compound (vi) can be obtained. Where necessary, the compound may be further purified.

In step 2, $R^{2'}$ is introduced simultaneously with ring opening of the oxirane ring of compound (vi) to give compound (xii). For example, t-BuLi and CuI are added to compound (xi) to allow reaction and the obtained compound (xi') and compound (vi) are reacted, whereby compound (xii) can be obtained.

First, the reaction to give compound (xi') is explained. The amount of t-BuLi to be used is generally 2-3 equivalents relative to compound (xi). The amount of CuI to be used is generally 0.5-0.6 equivalents relative to compound (xi). Examples of the solvent include diethyl ether-pentane, THF, hexane and the like. The amount of the solvent to be used is generally 0.2-50 ml per 1 mmol of compound (xi). The reaction temperature is generally −78-60° C., and the reaction time is generally 5 min-24 hr.

Compound (xii) can be obtained by adding compound (vi) to a reaction mixture containing compound (xi') which is obtained as mentioned above. The amount of compound (vi) to be used is generally 0.4-2 equivalents relative to compound (xi'). As the solvent, those similar to the solvent used for the above-mentioned reaction to give compound (xi') can be mentioned. The amount of the solvent to be used is generally 0.2-50 ml per 1 mmol of compound (vi). The reaction temperature is generally −78° C.-40° C., and the reaction time is generally 30 min-24 hr.

Compound (xii) can be isolated by a conventional method. For example, the reaction mixture is diluted with ethyl acetate, washed with water and saturated brine, dried over magnesium sulfate, filtered and concentrated, whereby compound (xii) can be obtained. Where necessary, the compound may be further purified.

In step 3, the 1,3-dioxane ring of compound (xii) is subjected to ring opening using an acid to give compound (xiii).

Examples of the acid include p-toluenesulfonic acid monohydrate (p-TsOH.$H_2O$), water-containing acetic acid, diluted hydrochloric acid and the like. The amount of the acid to be used is generally 0.1-1 equivalents relative to compound (xii). Examples of the solvent include methanol, ethanol, THF, acetone and the like. The amount of the solvent to be used is generally 0.2-100 ml per 1 mmol of compound (xii). The reaction temperature is generally 0-80° C., and the reaction time is generally 30 min-24 hr.

Compound (xiii) can be isolated by a conventional method. For example, the mixture is treated with saturated aqueous sodium hydrogen carbonate, concentrated, extracted with ethyl acetate, and the extract is washed with water and saturated brine, dried over magnesium sulfate, filtered and concentrated, whereby compound (xiii) can be obtained. Where necessary, the compound may be further purified.

In step 4, the hydroxyl group of compound (xiii) is protected to give compound (xv). First, the primary hydroxyl group of compound (xiii) is protected (i.e., converted to —$OA^7$), then the secondary hydroxyl group is protected (i.e., converted to —$OA^{4a}$ and —$OA^{5a}$). A compound wherein the primary hydroxyl group of compound (xiii) is protected (i.e., converted to —$OA^7$) is hereinafter to be referred to as compound (xiv).

First, protection primary hydroxyl group of compound (xiii) is explained. For example, when the protecting group for $A^7$ is t-butyldimethylsilyl, compound (xiii) is reacted with t-butyldimethylsilyl halide (e.g., t-butyldimethylsilyl chloride) in the presence of a base to give compound (xiv).

The amount of t-butyldimethylsilyl halide to be used is generally 1-1.5 equivalents relative to compound (xiii). Examples of the base include N,N-dimethyl-4-aminopyridine, pyridine, triethylamine and the like. The amount of the base to be used is generally 1-2 equivalents relative to compound (xiii). Examples of the solvent include dichloromethane, THF, benzene and the like. The amount of the solvent to be used is generally 0.2-100 ml per 1 mmol of compound (xiii). The reaction temperature is generally 0-80° C., and the reaction time is generally 30 min-24 hr. Compound (xiv) obtained by the above-mentioned reaction can be isolated by a conventional method. For example, the mixture was diluted with a solvent, washed with water and saturated brine, dried over magnesium sulfate, filtered, and concentrated. Where necessary, the compound may be further purified.

The hydroxyl group of the obtained compound (xiv) is protected to give compound (xv). For example, when the protecting group is isopropylidene, compound (xiv) and 2,2-dimethoxypropane are reacted in the presence of an acid to give compound (xv).

The amount of 2,2-dimethoxypropane to be used is generally 0.1 ml-large excess per 1 mmol of compound (xiv). Examples of the acid include p-toluenesulfonic acid monohydrate (p-TsOH.$H_2O$), camphorsulfonic acid (CSA) and the like. The amount of the acid to be used is generally 0.01-0.1 equivalents relative to compound (xiv). The reaction can be performed without using a solvent. When a solvent is used, for example, acetone, dichloromethane, THF and the like can be used. The reaction temperature is generally 0-60° C., and the reaction time is generally 10 min-24 hr.

Compound (xv) can be isolated by a conventional method. For example, the mixture was diluted with ethyl acetate, washed with saturated aqueous sodium hydrogen carbonate and saturated brine, dried over magnesium sulfate, filtered and concentrated to give the compound. Where necessary, the compound may be further purified.

In step 5, the protecting groups $A^6$ and $A^7$ are removed from compound (xv) to give compound (xix'). When the steric configuration of the asymmetric carbon to be bonded with —$OA^6$ does not require inversion, $A^6$ and $A^7$ may be removed by a method known per se. When the inversion reaction described in the below-mentioned scheme 7 is performed, $A^6$, inversion is performed and thereafter $A^7$ may be removed. A compound wherein the protecting group $A^6$ alone of compound (xv) has been removed (i.e., compound wherein —OA$^6$ in compound (xv) is converted to —OH) is hereinafter referred to as compound (xvi).

First, the deprotection of A$^6$ is explained. For example, compound (xv) is reacted with H$_2$O using an oxidant such as 2,3-dichloro-5,6-dicyano-p-benzoquinone (DDQ) and the like to give compound (xvi).

The amount of H$_2$O to be used is generally 0.1-10 ml per 1 mmol of compound (xv). Examples of the oxidant include 2,3-dichloro-5,6-dicyano-p-benzoquinone (DDQ). The amount of the oxidant to be used is generally 1-3 equivalents relative to compound (xv). Examples of the solvent include dichloromethane, dioxane, THF and the like. The amount of the solvent to be used is generally 0.2-100 ml per 1 mmol of compound (xv). The reaction temperature is generally 0-50° C., and the reaction time is generally 15 min-24 hr.

Compound (xvi) can be isolated by a conventional method. For example, the mixture was diluted with a solvent, washed with saturated aqueous sodium hydrogen carbonate and saturated brine, dried over magnesium sulfate, filtered and concentrated to give the compound. Where necessary, the compound may be further purified.

Then, A$^7$ is removed from compound (xvi) to give compound (xix'). For example, when A$^7$ is a t-butyldimethylsilyl group, compound (xvi) is reacted with a silyl group elimination agent to remove the silyl group to give compound (xix'). Examples of the silyl group elimination agent include quaternary ammonium fluoride (e.g., tetrabutylammonium fluoride (n-Bu$_4$NF)), HF-pyridine, HF-triethylamine, acetic acid, diluted hydrochloric acid and the like. When the above-mentioned fluoride is used as a silyl group elimination agent, the amount of the fluoride to be used is generally 1-2 equivalents relative to compound (xvi). Examples of the solvent for removal of the silyl group include THF, dioxane, ethyl acetate, pyridine and the like. The amount of the solvent to be used is generally 0.2-100 ml per 1 mmol of compound (xvi). The reaction temperature is generally 0-50° C., and the reaction time is generally 5 min-24 hr.

Compound (xix') can be isolated by a conventional method. For example, the mixture was diluted with ethyl acetate, washed with saturated aqueous sodium hydrogen carbonate and saturated brine, dried over magnesium sulfate, filtered and concentrated to give the compound. Where necessary, the compound may be further purified.

Compound (xix) in scheme 1 can also be produced by the following method of scheme 5. Compound (xxix) is encompassed in compound (xix).

scheme 5

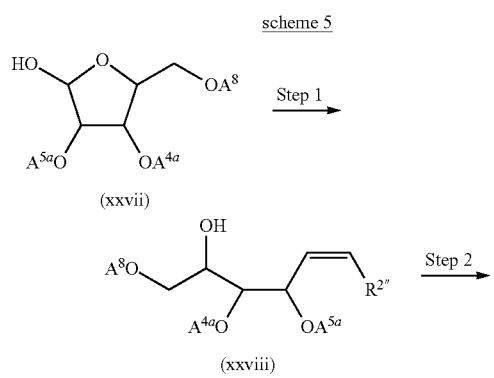

(xxvii)

(xxviii)

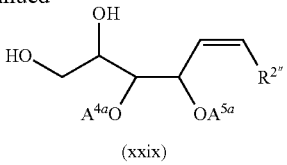

(xxix)

wherein A$^8$ is a hydroxyl-protecting group, R$^{2''}$ is a hydrocarbon group having a carbon number of 1-18, and other symbols are as defined above.

Examples of the hydroxyl-protecting group for A$^8$ include t-butyldimethylsilyl, t-butyldiphenylsilyl and the like. Examples of the "hydrocarbon group having a carbon number of 1-18" for R$^{2''}$ include those similar to the hydrocarbon groups exemplified as R$^2$ except hydrocarbon group having a carbon number of 20 and 19. In each formula in scheme 5, a group represented by —CH═CH—R$^{2''}$ is encompassed in R$^2$.

The starting compound (xxvii) can be produced by the method described in J. C. Tadav, S. Pamu, D. C. Bhunia, S. Pabberaja, Synlett. 2007, 992-994, or a method analogous thereto.

In step 1, a ═CH—R$^{2''}$ group is introduced simultaneously with ring opening of the oxolane ring of compound (xxvii) to give compound (xxviii). For example, compound (xxvii) and alkyltriphenylphosphonium halide (e.g., tridecyltriphenyl phosphonium bromide) are reacted in the presence of a base, whereby compound (xxviii) can be obtained.

The amount of alkyltriphenylphosphonium halide to be used is generally 1-10 equivalents relative to compound (xxvii). Examples of the base include n-BuLi, t-BuLi and the like. The amount of the base to be used is generally 1-10 equivalents relative to compound (xxvii). Examples of the solvent include THF, diethyl ether, toluene, hexane and the like. The amount of the solvent to be used is generally 0.2-50 ml per 1 mmol of compound (xxvii). The reaction temperature is generally −20° C.-30° C., and the reaction time is generally 30 min-24 hr.

Compound (xxviii) can be isolated by a conventional method. For example, the mixture was diluted with hexane-ethyl acetate, washed with water and saturated brine, dried over magnesium sulfate, filtered and concentrated to give the compound. Where necessary, the compound may be further purified.

In step 2, A$^8$ is removed from compound (xxviii) to give compound (xxix). For example, when the protecting group for A$^8$ is a silyl group, compound (xxviii) is reacted with a silyl group elimination agent to remove the silyl group, whereby compound (xxix) can be obtained. Examples of the silyl group elimination agent include halogenated quaternary ammonium salt (e.g., tetrabutylammonium fluoride (n-Bu$_4$NF)), HF-pyridine, HF-triethylamine, BF$_3$—OEt$_2$ and the like. The amount of the silyl group elimination agent to be used is generally 1-2 equivalents relative to compound (xxviii). Examples of the solvent for removing the silyl group include THF, dioxane, diethyl ether and the like. The amount of the solvent to be used is generally 0.2-100 ml per 1 mmol of compound (xxviii). The reaction temperature is generally 0-50° C., and the reaction time is generally 5 min-24 hr.

Compound (xxix) can be isolated by a conventional method. For example, the mixture was diluted with ethyl acetate, washed with saturated aqueous sodium hydrogen carbonate and saturated brine, dried over magnesium sulfate, filtered and concentrated to give the compound. Where necessary, the compound may be further purified.

Compound (xi) in scheme 4 can be produced, for example, by the method of the following scheme 6 or a method analogous thereto. Compound (xi') is encompassed in compound (xi).

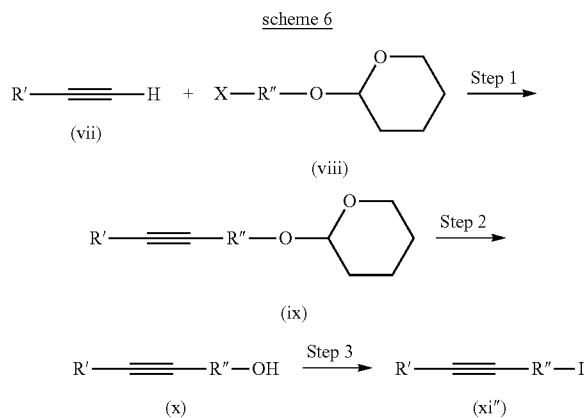

scheme 6 wherein X is a halogen atom, R' is an alkyl group having a carbon number of 1-9, and R" is an alkyl group having a carbon number of 2-10.

As the halogen atom for X, bromine, chlorine, iodine etc. (X in compound (viii)) can be mentioned.

The starting compound (vii) may be a commercially available product (e.g., manufactured by TOKYO CHEMICAL INDUSTRY CO., LTD.). The starting compound (viii) can be produced by the method described in J. Muller, M. Brunnbauer, M. Schmidt, A. Zimmermann, A. Terfort, Synthesis. 2005, 998-1004, or a method analogous thereto.

In step 1, compound (vii) and compound (viii) are reacted in the presence of a base to give compound (ix).

The amount of compound (viii) to be used is generally 0.5-2 equivalents relative to compound (vii). Examples of the base include n-BuLi, sodium hydride, potassium hydride, DBU and the like. The amount of the base to be used is generally 1-2 equivalents relative to compound (vii). Examples of the solvent include a mixed solution of hexamethylphosphoric triamide (HMPA) and tetrahydrofuran (THF), THF, diethyl ether, hexane and the like. The amount of the solvent to be used is generally 0.2-50 ml per 1 mmol of compound (vii). The reaction temperature is generally −78° C.-30° C., and the reaction time is generally 10 min-24 hr.

Compound (ix) can be isolated by a conventional method. For example, excess base is neutralized with aqueous saturated ammonium chloride, and the mixture is extracted with ether, washed with water and saturated brine, dried over magnesium sulfate, filtered and concentrated to give the compound. Where necessary, the compound may be further purified.

In step 2, the tetrahydropyranyloxy group of compound (ix) is converted a hydroxyl group in the presence of an acid to give compound (x).

Examples of the acid include p-toluenesulfonic acid monohydrate, pyridinium p-toluenesulfonate, acetic acid, dilute hydrochloric acid and the like. The amount of the acid to be used is generally 0.001-1 equivalents relative to compound (ix). Examples of the solvent include methanol, ethanol, and THF. The amount of the solvent to be used is generally 0.2-100 ml per 1 mmol of compound (ix). The reaction temperature is generally 0-80° C., and the reaction time is generally 10 min-24 hr.

Compound (x) can be isolated by a conventional method. For example, saturated aqueous sodium hydrogen carbonate is added to a mixture, and the mixture is concentrated, extracted with hexane, and the extract is washed with water and saturated brine, dried over magnesium sulfate, filtered and concentrated to give the compound. Where necessary, the compound may be further purified.

In step 3, the hydroxyl group of compound (x) is converted to iodine to give compound (xi"). For example, compound (x) is reacted with an activator (e.g., methanesulfonyl chloride (MsCl)) in the presence of a base to activate the hydroxyl group, and the obtained resultant product is reacted with NaI, whereby compound (xi') can be obtained.

First, activation of hydroxyl group is explained. Examples of the base include triethylamine, N-ethyldiisopropylamine, pyridine, DMAP and the like. The amount of the base to be used is generally 1-3 equivalents relative to compound (x). The amount of an activator such as methanesulfonyl chloride and the like to be used is generally 1-1.5 equivalents relative to compound (x). Examples of the solvent include dichloromethane, THF, diethyl ether and the like. The amount of the solvent to be used is generally 0.5-50 ml per 1 mmol of compound (x). The reaction temperature is generally 0-40° C., and the reaction time is generally 10 min-24 hr. The obtained resultant product can be isolated by a conventional method, for example, diluted with a solvent, concentrated, extracted with hexane, and the extract is washed with water and saturated brine, dried over magnesium sulfate, filtered and concentrated to give the compound.

Then, the obtained resultant product is reacted with NaI to give compound (xi'). The amount of NaI to be used is generally 1-5 equivalents relative to compound (x). Examples of the solvent include acetone, THF, diethyl ether and the like. The amount of the solvent to be used is generally 0.5-100 ml per 1 mmol of compound (x). The reaction temperature is generally 0-180° C. (generally 0-80° C. when solvent is acetone), and the reaction time is generally 15 min-24 hr.

Compound (xi') can be isolated by a conventional method. For example, the mixture was diluted with hexane, washed with saturated aqueous sodium hydrogen carbonate and saturated brine, dried over magnesium sulfate, filtered and concentrated to give the compound. Where necessary, the compound may be further purified.

Compound (I) having a steric structure of

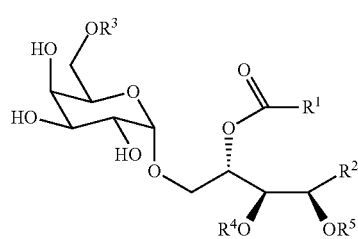

and compound (II) having a steric structure of

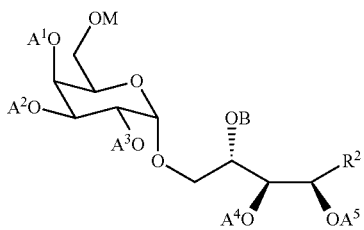

can be produced by using compound (xix″) obtained according to the following scheme 7 as compound (xix) in the reaction of the aforementioned scheme 1. Compound (I) and compound (II) having such a steric structure can also be produced by using by using compound (xxix′) obtained according to the following scheme 8 as compound (xix) in the reaction of the aforementioned scheme 1.

Schemes 7 and 8 show the case where $A^{4a}$ and $A^{5a}$ of compound (xix) in scheme 1 are isopropylidene. Even when $A^{4a}$ and $A^{5a}$ are hydroxyl-protecting groups formed by a combination of $A^{4a}$ and $A^{5a}$ other than isopropylidene, or divalent hydrocarbon groups having a carbon number of 1-5, which is other than isopropylidene, compound (I) and compound (II) having the above-mentioned steric structures can also be produced according to schemes 7 and 8.

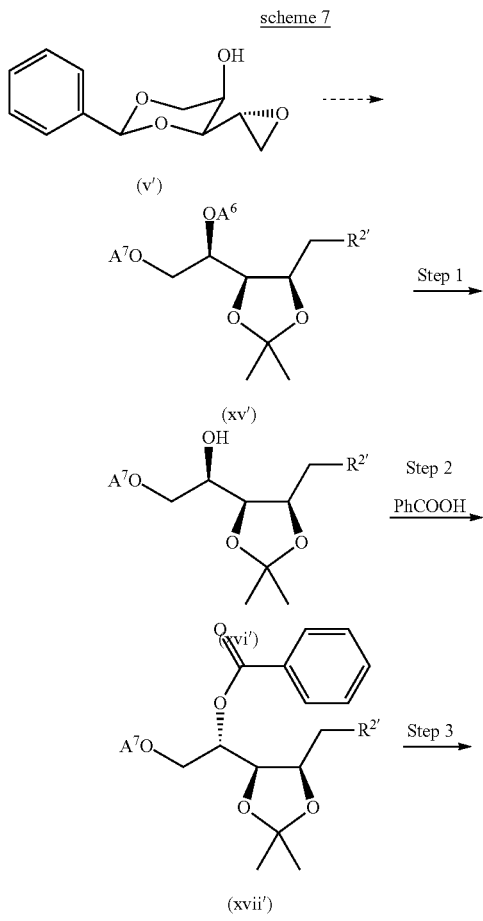

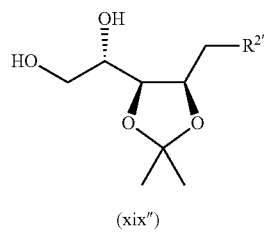

wherein each symbol is as defined above.

The starting compound (v′) can be obtained according to K. Murata, T. Toba, K. Nakanishi, B. Takahashi, T. Yamamura, S. Miyake, and H. Annoura, J. Org. Chem. 2005, 70, 2398-2401.

In step 1, compound (xvi′) can be obtained by subjecting compound (xv′), which is obtained by subjecting compound (v′) to reactions similar to the aforementioned scheme 4, steps 1-4, to a reaction similar to the deprotection of $A^6$ of step 5 of scheme 4.

In step 2, the hydroxyl group of compound (xvi′) is reacted with benzoic acid in the presence of azocarboxylic acid ester (e.g., diethyl azodicarboxylate) and triphenylphosphine to give compound (xvii′) wherein the steric configuration of hydrocarbon to which the hydroxyl group of compound (xvi′) is bonded is inverted.

The amount of benzoic acid to be used is generally 1-5 equivalents relative to compound (xvi′). The amount of azocarboxylic acid ester to be used is generally 2-5 equivalents relative to compound (xvi′). The amount of triphenylphosphine to be used is generally 2-6 equivalents relative to compound (xvi′). Examples of the solvent include THF, diethyl ether, benzene, toluene, hexane and the like. The amount of the solvent to be used is generally 1-100 ml per 1 mmol of compound (xvi′). The reaction temperature is generally −78° C.-50° C., and the reaction time is generally 30 min-24 hr. Compound (xvii′) may be purified as necessary.

In step 3, A7 and benzoyl group are removed. The step can be performed according to the aforementioned scheme 4, step 5.

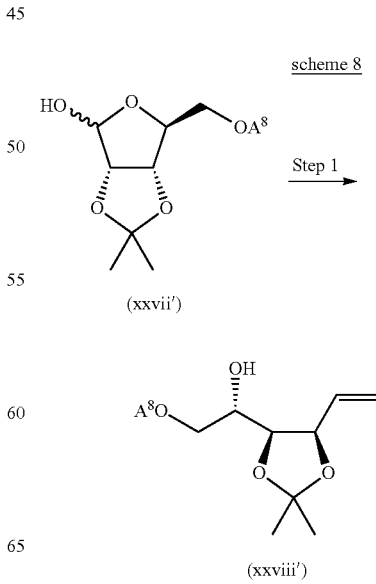

-continued

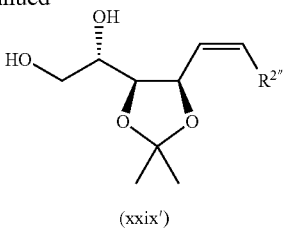

(xxix')

wherein each symbol is as defined above.

The starting compound (xxvii') can be obtained according to J. C. Tadav, S. Pamu, D. C. Bhunia, S. Pabberaja, Synlett. 2007, 992-994.

Step 1 and 2 can be performed according to the aforementioned scheme 5.

Compound (xx) of scheme 1 can also be produced, for example, by the method of the following scheme 9 or a method analogous thereto.

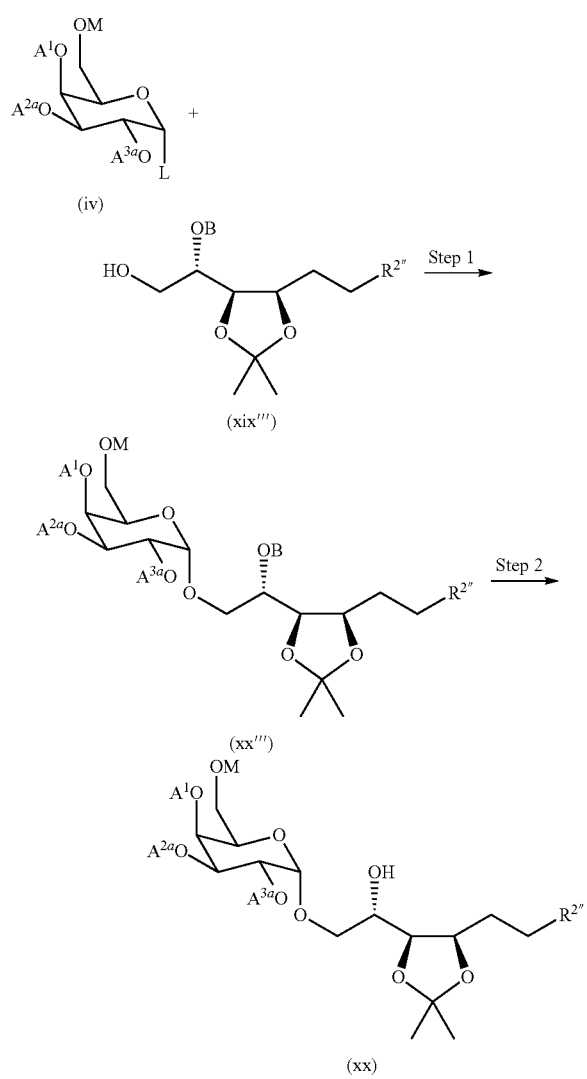

wherein each symbol is as defined above.

In step 1, compound (iv) obtained in the above-mentioned scheme 2 and compound (xix''') obtained in the following scheme 10 are reacted in a solvent in the presence of silver trifluoromethanesulfonate and molecular sieves to give compound (xx'''). The step can be performed according to the aforementioned scheme 1, step 1.

In step 2, the hydroxyl-protecting group B of compound (xx''') is removed to give compound (xx'''). The step can be performed according to the aforementioned scheme 4, step 5.

Compound (xix''') of scheme 9 can be produced, for example, by the method of the following scheme 10, or a method analogous thereto.

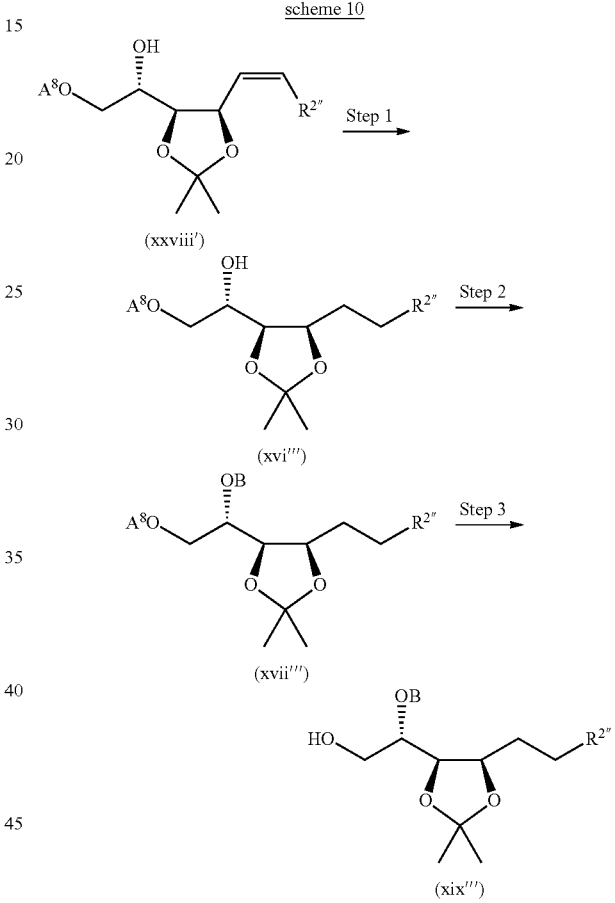

wherein each symbol is as defined above.

In step 1, the unsaturated bond of compound (xxviii') obtained in scheme 8, step 1, is reduced with a catalyst in a solvent under a hydrogen atmosphere to give compound (xvi'''). As the catalyst, Pd(OH)$_2$ carbon, Pd carbon, Pd black and the like can be mentioned. The amount of the catalyst to be used is generally 50 mg-500 mg per 1 mmol of the compound (xxviii'). Examples of the solvent include trichloromethane, methanol, ethanol, ethyl acetate, hexane, dichloromethane, THF, a mixed solvent thereof and the like. The amount of the solvent to be used is generally 1-100 ml per 1 g of the compound (xxviii'). The reaction temperature is generally 10-80° C. and the reaction time is generally 15 min-1 day.

In step 2, the hydroxyl group of compound (xvi''') is protected to give compound (xvii''').

Compound (xvii''') can be obtained by reacting compound (xvi''') with B-L (B is as defined above, and L is a leaving group) in a solvent in the presence of a base. Examples of the solvent include dichloromethane, THF, benzene, diethyl ether, a mixed solvent thereof and the like. The amount of the solvent to be used is generally 5-50 ml per 1 mmol of compound (xvi'''). Examples of the base include 2,6-lutidine, 4-dimethylaminopyridine, pyridine, triethylamine and the like. The amount of the base to be used is generally 1-5 equivalents relative to compound (xvi'''). Examples of B-L include t-butyldimethylsilyl trifluoromethanesulfonate, t-butyldimethylsilyl chloride and the like. The amount of B-L to be used is generally 1-5 equivalents relative to compound (xvi''').

In step 3, hydroxyl-protecting group $A^8$ of compound (xvii''') is removed to give compound (xix'''). The step can be performed according to the aforementioned scheme 4, step 5. For example, when HF-pyridine (70% HF) is used as an elimination agent of silyl group, the amount of fluoride to be used is generally 1-2 ml per 1 mmol of compound (xvii'''), and the solvent for removal of silyl group is preferably pyridine.

Next, the pharmaceutical use of the present invention is explained.

By administration of compound (I) or a salt thereof of the present invention, a complex with the CD1d protein possessed by APC is formed, and the complex is presented to NKT cells. The NKT cells recognizes the complex via TCR, and can selectively produce IFN-γ, which is one kind of cytokine that activates the function of immunocytes, in a large amount, from among the immunoregulatory functions it has, while inhibiting the production of IL-4. To be specific, the IFN-γ/IL-4 ratio is not less than 10, and extremely high selective IFN-γ production is confirmed as compared to conventionally known glycolipids (see FIGS. 1-4). Therefore, compound (I) or a salt thereof of the present invention is useful as an anti-cancer agent or an immunostimulator for inhibiting tumor growth, and further for the treatment of a cell proliferation disorder or for correction of Th1/Th2 immunity balance.

Examples of the cancer treatment subject include, but are not limited to, carcinomas of esophagus, stomach, liver, pancreas, breast, colon, kidney, lung (including small cell lung cancer, non-small cell lung cancer), gall bladder, ovary, testis, bladder, cervical division, thyroid gland, prostate and skin (including squamous cell cancer); hematopoietic neoplasm of the lymphoid system (including leukemia, acute lymphatic leukemia, acute lymphoblastic leukemia, B cell lymphoma, T cell lymphoma, Hodgkin lymphoma, non-Hodgkin lymphoma, hairy cell leukemia, Burkitt's lymphoma); hematopoietic neoplasm of the myeloid system (including acute and chronic myeloid leukemia, myelodysplastic syndrome and acute promyeloid leukemia); tumors of mesenchymal origin (including fibrosarcoma and rhabdomyosarcoma); tumor in the central nervous system and the peripheral nervous system (including astrocytoma, neuroblastoma, glioma and schwannoma); other tumors (including melanoma, seminoma, teratocarcinoma, osteosarcoma, xeroderma pigmentosum, keratoacanthoma, follicular cancer of the thyroid, Kaposi's sarcoma).

The cell proliferation disorder is a concept including familial adenomatous polyposis, psoriasis, benign prostatic hyperplasia, neurofibromatosis, vascular smooth muscle cell proliferation relating to atherosclerosis, pulmonary fibrosis, arthritis, glomerulonephritis, postoperative stenosis and restenosis.

As the subject of administration of compound (I) or a salt thereof of the present invention, mammals such as human and the like can be mentioned.

When compound (I) or a salt thereof of the present invention is administered to human, it can be safely administered orally or parenterally as it is or in the form of a pharmaceutical composition such as an agent for oral administration (e.g., powder, granule, tablet, capsule), an agent for parenteral administration (e.g., injection, suppository (e.g., rectal suppository, vaginal suppository)) and the like, which is obtained by mixing compound (I) or a salt thereof with a pharmacologically acceptable carrier (e.g., excipient, diluent) and the like. These preparations can be produced by a conventionally known method.

Examples of the injection include subcutaneous injection, intravenous injection, intramuscular injection, intraperitoneal injection, drip infusion and the like. Injections can also be prepared into an aqueous injection using the compound or a salt thereof together with a solubilizer (e.g., β-cyclodextrins), dispersing agent (e.g., carboxymethylcellulose, sodium alginate), preservative (e.g., methylparaben, propylparaben, benzyl alcohol, chlorobutanol), isotonicity agent (e.g., sodium chloride, glycerol, sorbitol, glucose) and the like according to a conventional method. It is also possible to prepare an oily injection by dissolving, suspending or emulsifying in vegetable oil (e.g., olive oil, sesame oil, peanut oil, cottonseed oil, corn oil), propylene glycol and the like.

An agent for oral administration can also be produced by appropriately adding, for example, excipient (e.g., lactose, sucrose, starch), disintegrant (e.g., starch, calcium carbonate), binder (e.g., starch, gum arabic, carboxymethylcellulose, polyvinylpyrrolidone, hydroxypropylcellulose), lubricant (e.g., talc, magnesium stearate, polyethylene glycol) and the like to the compound or a salt thereof, compression molding the mixture, and coating the resulting product with hydroxypropylmethylcellulose and the like as necessary. Suppository can be produced by mixing the compound or a salt thereof and nonirritating excipient (e.g., polyethylene glycol, glyceride of higher fatty acid).

While the daily dose of compound (I) or a salt thereof varies depending on the age, body weight, symptom, dosage form, administration method, dosing period and the like, it is, for example, generally 0.01-100 mg/kg body weight, preferably 0.01-50 mg/kg body weight, more preferably 0.01-20 mg/kg body weight, per patient (adult, body weight about 60 kg), which can be orally or parenterally administered in one to several portions a day.

EXAMPLES

The present invention is explained in more detail in the following by referring to Production Examples, Examples, Reference Examples and Experimental Examples which are not to be construed as limitative.

The abbreviations in the present specification mean as follows.

mp: melting point
IR: infrared spectroscopy spectrum
EIMS: electron impact mass spectrometry spectrum
ESIMS: electrospray ionization mass spectrometry spectrum
HREIMS: high resolution electron impact mass spectrometry spectrum
Calcd.: calculated
Found.: found
NMR: nuclear magnetic resonance spectrum
Hz: hertz
J: coupling constant
m: multiplet
q: quartet t: triplet td: triple doublet d: doublet dd: double doublet dt: double triplet s: singlet br: broad CDCl$_3$: deuterated chloroform Bn: benzyl group Bu: butyl group Me: methyl group Ph: phenyl group Ts: tosyl group AgOTf: silver trifluoromethanesulfonate TBDMS: t-butyldimethylsilyl group TMS: trimethylsilyl group PMB: p-methoxybenzyl group HMPA: hexamethylphosphoric triamide DDQ: 2,3-dichloro-5,6-dicyano-p-benzoquinone DBN: diazabicyclononene DBU: diazabicycloundecene PMP: 4-methoxyphenyl(p-methoxyphenyl)

PMB: 4-methoxybenzyl(p-methoxybenzyl)

DMAP: N,N-dimethyl-4-aminopyridine

HF: hydrofluoric acid

NBS: N-bromosuccinimide

WSC: 1-[3-(dimethylamino)propyl]-3-ethylcarbodiimide

THF: tetrahydrofuran

CSA: camphorsulfonic acid

DMF: N,N-dimethylformamide room temperature: 20-30° C.

Production Example 1

Synthesis of 4-methylphenyl 4,6-O-benzylidene-2,3-di-O-(4-methoxybenzyl)-1-thio-β-D-galactopyranoside (Compound 2)

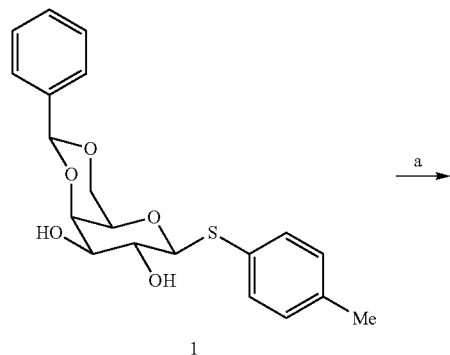

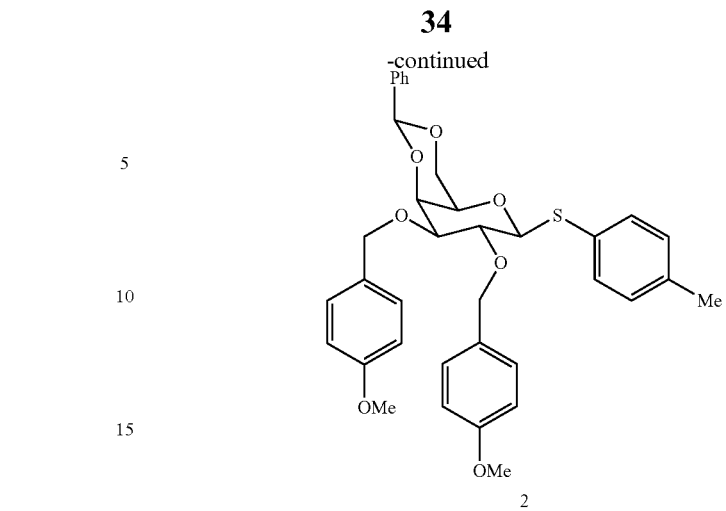

(Step a)

To a solution of 4-methylphenyl 4,6-O-benzylidene-1-thio-β-D-galactopyranoside (compound 1) (13.28 g, 35.47 mmol) which is a compound known in a literature (O. Plettenburg, V. Bodmer-Narkevitch and C-H. Wong, J. Org. Chem. 2002, 67, 4559-4564.), which is obtained from penta-O-acetyl-β-D-galactopyranose as starting materials, 4-methoxybenzyl chloride (11.65 g, 73.39 mmol), and tetrabutylammonium iodide (0.6 g, 1.62 mmol) in N,N-dimethylformamide (DMF) (100 ml) was added sodium hydride (60% oil dispersion, 3.12 g, 78.00 mmol). The mixture was heated to 65° C. and stirred for 45 min, and further at 70° C. for 15 min. At room temperature, ice (100 g) was added and the mixture was extracted with ethyl acetate. The organic layer was washed with water and saturated brine, dried over magnesium sulfate, filtered and concentrated under reduced pressure to give crude crystals. The crude crystals were dissolved in ethyl acetate (30 ml) under heating, hexane was added to allow recrystallization, and the crystals were collected by filtration to give the title compound 2 (17.6 g, 81%).

mp 143-145° C. IRvmax(KBr) 3000-2850, 1614, 1586 (w), 1515 cm$^{-1}$. 270 MHz $^1$H NMR (CDCl$_3$) δ 2.30 (3H, s), 3.39 (1H, bs), 3.58 (1H, dd, J=3.2, 9.2 Hz), 3.78-3.85 (7H, m, containing two 3H singlets at 3.79 and 3.81 ppm), 4.10 (1H, d, J=2.5 Hz), 4.36 (1H, d, J=12.2 Hz), 4.54 (1H, d, J=9.2 Hz), 4.62-4.65 (4H, m), 5.47 (1H, s), 6.80-6.90 (4H, m), 7.00 (2H, d, J=7.8 Hz), 7.25-7.55 (9H, m), 7.60 (2H, d, J=7.8 Hz). EIMS; m/z 614 [M]$^+$. HREIMS, Calcd. for C$_{36}$H$_{38}$O$_7$S: 614.2338. Found: 614.2339.

Production Example 2

Synthesis of 4,6-O-benzylidene-2,3-di-O-4-methoxybenzyl-α,β-D-galactopyranose (Compound 3)

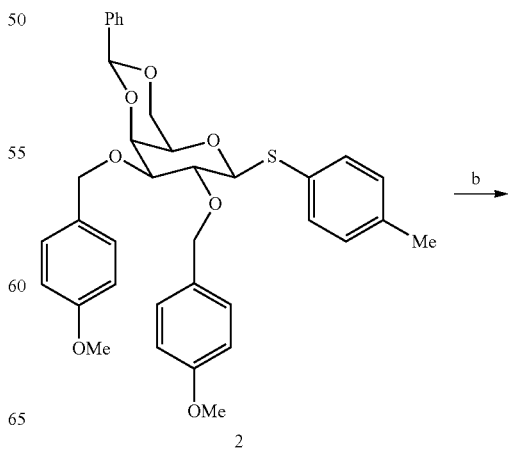

-continued

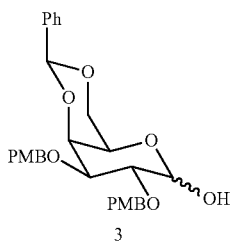

3

(Step b)

To a solution of compound 2 (24.00 g, 39.04 mmol) in acetone (800 ml) was added N-bromosuccinimide (NBS) (8.40 g, 47.20 mmol) at −20° C. and the mixture was stirred for 45 min. Saturated aqueous sodium hydrogen carbonate (100 ml) was added and the mixture was concentrated under reduced pressure, and extracted with ethyl acetate. The organic layer was washed with saturated aqueous sodium hydrogen carbonate and saturated brine, dried over magnesium sulfate, filtered and concentrated under reduced pressure to give crude crystals. The crude crystals were recrystallized from ethyl acetate-hexane (1:1) to give the title compound 3 (19.20 g, 96%).

mp 130-134° C. IRvmax (KBr) 3419 (br), 3000-2835, 1710, 1613, 1586 (w), 1514 cm$^{-1}$. 400 MHz $^1$H NMR (CDCl$_3$) δ 2.94 (1H, bs, OH), 3.80 (6H, s), 3.83-4.23 (6H, m), 4.60-4.82 (4H, m), 5.31 (1H, bs, anomeric H), 5.48 (1H, s), 6.85-6.87 (4H, m), 7.26-7.38 (7H, m), 7.51-7.54 (2H, m). EIMS; m/z 508 [M]$^+$. HREIMS, Calcd. for C$_{29}$H$_{32}$O$_8$: 508.2097. Found: 508.2094.

Production Example 3

Synthesis of trichloroacetoimidoyl 4,6-O-benzylidene-2,3-di-O-(4-methoxybenzyl)-α-D-galactopyranoside (Compound 4)

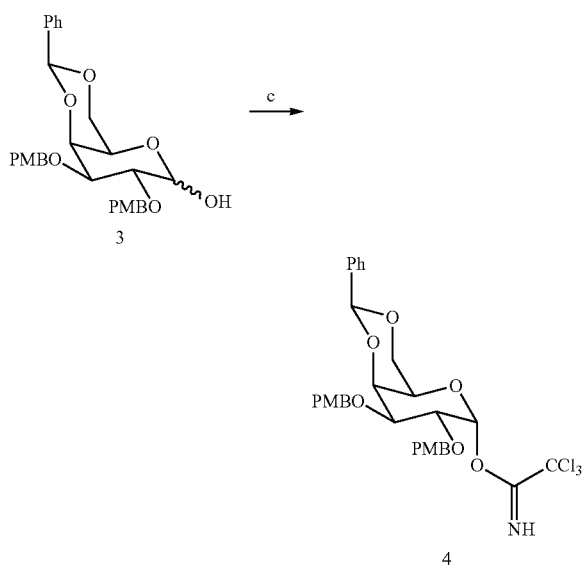

(Step c)

To a solution of compound 3 (2.54 g, 5.00 mmol) in dichloromethane (70 ml) were added Cl$_3$CCN (7.22 g, 50 mmol) and cesium carbonate (810 mg, 2.50 mmol), and the mixture was stirred for 24 hr at room temperature and diluted with dichloromethane. The organic layer was washed with water, saturated aqueous sodium hydrogen carbonate and saturated brine, dried over magnesium sulfate, filtered and concentrated under reduced pressure to give the title compound 4 (3.13 g, 96%). This was used for the next reaction without purification.

IR vmax(KCl) 3337 (w), 3000-2840 (w), 1732, 1672, 1613, 1586, 1514 cm$^{-1}$. 270 MHz $^1$H NMR (CDCl$_3$) δ 3.80 (6H, s), 3.88-4.24 (6H, m), 4.68-4.74 (4H, m), 5.50 (1H, s), 6.59 (1H, d, J=3.2 Hz, anomeric H), 6.81-6.85 (4H, m), 7.23-7.32 (7H, m), 7.50-7.53 (2H, m), 8.55 (1H, s).

Production Example 4

Synthesis of 4,5-anhydro-1,3-O-benzylidene-2-O-(4-methoxybenzyl)-D-arabitol (Compound 6)

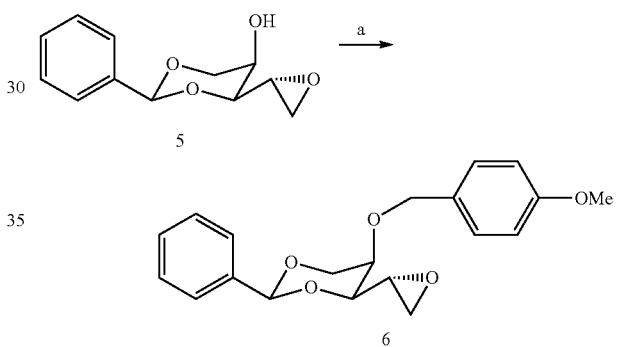

(Step a)

To a solution of 4,5-anhydro-1,3-O-benzylidene-D-arabitol (compound 5) (2.23 g, 10.03 mmol) which is a compound known in a literature (K. Murata, T. Toba, K. Nakanishi, B. Takahashi, T. Yamamura, S. Miyake, and H. Annoura, J. Org. Chem. 2005, 70, 2398-2401.), which is obtained from D-arabitol as starting materials, and 4-methoxybenzyl chloride (2.04 g, 13.03 mmol) in DMF (10 ml) was added sodium hydride (60% oil dispersion, 560 mg, 14.00 mmol) under ice-cooling. The mixture was stirred at room temperature for 3 hr. Ice was added, and the mixture was extracted with ethyl acetate. The organic layer was washed with water and saturated brine, dried over magnesium sulfate, filtered and concentrated under reduced pressure. The residue was purified by silica gel column chromatography. The residue was eluted with hexane-ethyl acetate (9:1, 3:1, finally 3:2) to give the title compound 6 (3.18 g, 93%).

mp 108-109° C. IR vmax(KCl) 1613, 1584, 1514 cm$^{-1}$. 270 MHz $^1$H NMR (CDCl$_3$) δ 2.83 (1H, dd, J=2.4, 5.1 Hz), 2.91 (1H, dd, J=4.1, 4.9 Hz), 3.34 (1H, m), 3.50 (1H, d, J=1.6 Hz), 3.64 (1H, dd, J=1.6, 5.9 Hz), 3.81 (1H, s), 3.91 (1H, d, J=12.1 Hz), 4.40 (1H, d, J=12.1 Hz), 4.60 (1H, d, J=11.9 Hz), 4.78 (1H, d, J=11.9 Hz), 6.82 (2H, d, J=8.6 Hz), 7.32-7.35 (5H, m), 7.49-7.53 (2H, m). FABMS; m/z 342 [M]$^+$.

HRFABMS, Calcd. for $C_{20}H_{22}O_5$: 342.1467. Observed: 342.1468. Anal. Found, C, 69.58; H, 6.66. Calcd. for $C_{20}H_{22}O_5$: C, 70.16; H, 6.48.

Production Example 5

Synthesis of 1-(tetrahydro-2H-pyran-2-yloxy)-6-tridecyne (Compound 9)

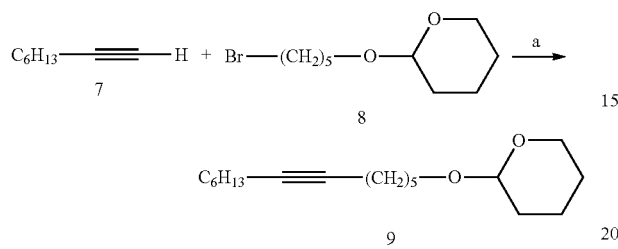

(Step a)

To a solution of 1-octyne (compound 7) (7.40 g, 113.43 mmol) in hexamethylphosphoric triamide (HMPA) (150 ml) and tetrahydrofuran (THF) (300 ml) was added dropwise n-butyllithium (n-BuLi) (1.6M hexane solution, 85.0 ml, 136 mmol) at −40° C. After stirring at this temperature for 1 hr, to this solution was slowly added dropwise a solution of 1-bromo-5-(tetrahydro-2H-pyran-2-yloxy)pentane (compound 8) (28.3 g, 136 mmol) which is a compound known in a literature (J. Muller, M. Brunnbauer, M. Schmidt, A. Terfort, Synthesis. 2005, 998-1004.) in THF (50 ml). The mixture was stirred at room temperature overnight (16 hr). Excess base was neutralized with saturated aqueous ammonium chloride and the mixture was extracted with ether. The organic layer was washed with water and saturated brine, dried over magnesium sulfate, filtered and concentrated under reduced pressure. The residue was purified by silica gel column chromatography and eluted with hexane-ethyl acetate (19:1) to give the title compound 9 (20.6 g, 65%).

IR vmax (KCl) 2934, 2859 cm$^{-1}$. 270 MHz $^1$H NMR (CDCl$_3$) δ 0.89 (3H, t, J=6.8 Hz), 1.21-1.90 (20H, m), 2.10-2.16 (4H, m), 3.38 (1H, m), 3.48 (1H, m), 3.75 (1H, m), 3.87 (1H, m), 4.58 (1H, dd, J=3.0, 3.8 Hz). EIMS; m/z 195, 280 [M]$^+$. HREIMS, Calcd. for $C_{18}H_{32}O_2$: 280.2402. Observed: 280.2384.

Production Example 6

Synthesis of 1-hydroxy-6-tridecyne (Compound 10)

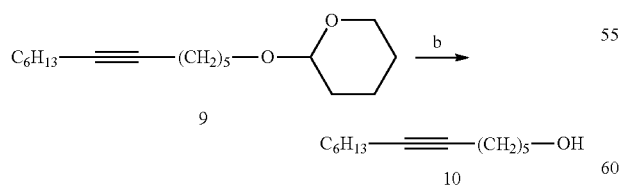

(Step b)

A solution of compound 9 (7.40 g, 26.39 mmol) and p-toluenesulfonic acid monohydrate (350 mg, 1.84 mmol) in methanol (200 ml) was stirred for 6 hr at room temperature, saturated aqueous sodium hydrogen carbonate (40 ml) was added, and the mixture was concentrated under reduced pressure and extracted with hexane. The organic layer was washed with water and saturated brine, dried over magnesium sulfate, filtered and concentrated under reduced pressure. The residue was purified by silica gel column chromatography and eluted with hexane-ethyl acetate (19:1) to give the title compound 10 (5.04 g, 97%) as an oil compound.

IR vmax (KCl) 3338, 2931, 2859 cm$^{-1}$. 270 MHz $^1$H NMR (CDCl$_3$) δ 0.89 (3H, t, J=6.8 Hz), 1.20-1.63 (14H, m), 2.10-2.20 (4H, m), 3.60-3.70 (2H, m).

Production Example 7

Synthesis of 1-iodo-6-tridecyne (Compound 11)

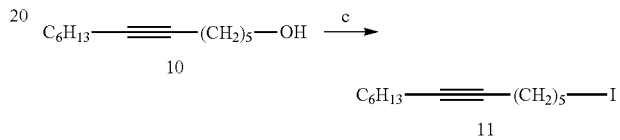

(Step c)

To a solution of compound 10 (5.05 g, 25.72 mmol) and triethylamine (Et$_3$N) (6.50 g, 64.31 mmol) in dichloromethane (50 ml) was added methanesulfonyl chloride (MsCl) (3.68 g, 32.15 mmol) at 0° C. and the mixture was stirred for 30 min. The mixture was diluted with dichloromethane, and the organic layer was washed with water and saturated brine, dried over magnesium sulfate, filtered and concentrated under reduced pressure. The residue was dissolved in acetone (250 ml), NaI (7.70 g, 51.37 mmol) was added, and the mixture was refluxed overnight (16 hr). The mixture was concentrated under reduced pressure and diluted with hexane. The organic layer was washed with saturated aqueous sodium hydrogen carbonate and saturated brine, dried over magnesium sulfate, filtered and concentrated under reduced pressure. The residue was purified by silica gel column chromatography and eluted with hexane-ethyl acetate (19:1) to give the title compound 11 (6.54 g, 83%) as an oil compound.

IR vmax(KBr) 2930, 2857 cm$^{-1}$. 400 MHz $^1$H NMR (CDCl$_3$) δ 0.89 (3H, t, J=6.8 Hz), 1.23-1.54 (12H, m), 1.81-1.87 (2H, m), 2.11-2.20 (4H, m), 3.19 (1H, t, J=7.0 Hz). EIMS: m/z 306 [M]$^+$. HREIMS: Calcd. for $C_{18}H_{32}I$: 306.0835. Observed: 306.0834.

Production Example 8

Synthesis of (2R,3R,4R)-1,3-O-[(S)-benzylidene]-4-hydroxy-2-(4-methoxybenzyloxy)-11-octadecyne (Compound 12)

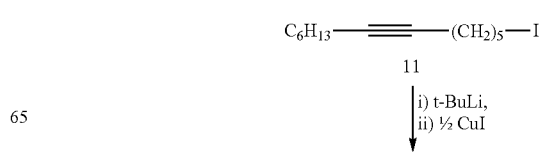

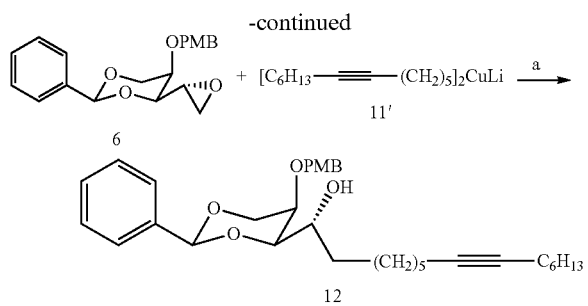

(Step a)

To a solution of compound 11 (4.55 g, 14.86 mmol) in diethyl ether-pentane (1:1, 35 ml) was added t-BuLi (1.5M pentane solution, 24 ml, 36.0 mmol) at −78° C. in an argon stream. After 5 min, the mixture was stirred for at room temperature for 1 hr and the solution was added to a suspension of CuI (1.42 g, 7.43 mmol) in THF (15 ml) at −40° C. in an argon stream. This solution was stirred at −30° C. for 30 min. A solution of compound 6 (2.54 g, 7.43 mmol) in THF (20 ml) was added dropwise to a solution of dialkyl cuprate (compound 11') obtained above at −20° C. After stirring overnight (16 hr) at room temperature, the reaction mixture was diluted with ethyl acetate, and the organic layer was washed with water and saturated brine, dried over magnesium sulfate, filtered and concentrated under reduced pressure. The residue was purified by silica gel column chromatography and eluted with hexane-ethyl acetate (4:1, further 2:1) to give the title compound 12 (3.63 g, 94%) as cotton-like crystals.

mp 80-81° C. (from hexane-EtOAc=3:1). IR νmax (KCl) 3451, 3000, 2932, 2854, 1610, 1585, 1511 cm$^{-1}$. 400 MHz $^1$H NMR (CDCl$_3$) δ 0.88 (3H, t, J=7.0 Hz), 1.15-1.72 (18H, m), 1.76 (1H, d, J=6.0 Hz, OH), 2.10-2.15 (4H, m), 3.56 (1H, s), 3.62 (1H, d, J=8.0 Hz), 3.81 (3H, s), 3.90 (1H, m), 3.92 (1H, d, J=12.6 Hz), 4.42 (1H, d, J=12.0 Hz), 4.52 (1H, d, J=12.6 Hz), 4.82 (1H, d, J=12.0 Hz), 5.56 (1H, s), 6.91 (2H, d, J=8.0 Hz), 7.30-7.38 (5H, m), 7.52 (2H, m). FABMS (positive-ion): m/z 522 [M]$^+$. HRFABMS (positive-ion): Calcd. for C$_{33}$H$_{46}$O$_5$: 522.3345. Observed: 522.3352. Anal. Calcd. for C$_{33}$H$_{46}$O$_5$: C, 75.83; H, 8.87. Found: C, 75.68; H, 8.92.

Production Example 9

Synthesis of (2R,3R,4R)-1,3,4-trihydroxy-2-(4-methoxybenzyloxy)-11-octadecyne (Compound 13)

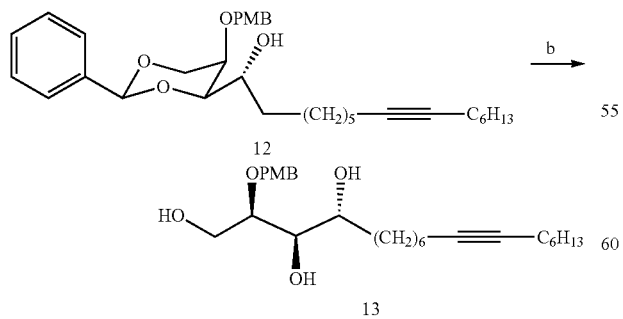

(Step b)

To a solution of compound 12 (3.05 g, 5.83 mmol) in methanol (180 ml) was added p-toluenesulfonic acid monohydrate (p-TsOH.H$_2$O) (300 mg, 1.58 mmol), and the mixture was stirred for 2 hr at room temperature, neutralized with saturated aqueous sodium hydrogen carbonate, concentrated under reduced pressure and extracted with ethyl acetate. The organic layer was washed with water and saturated brine, dried over magnesium sulfate, filtered and concentrated under reduced pressure. The residue was purified by silica gel column chromatography and eluted with hexane-ethyl acetate (2:1, 1:1 further 1:9) to give the title compound 13 (2.16 g, 85%) as an oil compound and recovered starting material (compound 12) (400 mg, 13%).

IR νmax(KBr) 3323 (broad), 2929, 2855, 1613, 1585 (w), 1513 cm$^{-1}$. 400 MHz $^1$H NMR (CDCl$_3$) δ 0.89 (3H, t, J=6.8 Hz), 1.25-1.55 (18H, m), 2.12-2.16 (4H, m), 2.26 (1H, d, J=7.6 Hz, OH), 2.53 (1H, m, OH), 2.84 (1H, d, J=7.6 Hz, OH), 3.57-3.60 (2H, m), 3.71 (3H, m), 3.80 (1H, m), 3.81 (3H, s), 3.95 (1H, m), 4.51, 4.70 (2H, AB$_q$, J=11.2 Hz), 6.90 (2H, d, J=8.6 Hz), 7.27 (2H, d, J=8.6 Hz). FABMS (positive-ion): m/z 433, 434, 435 [M+H]$^+$. HRFABMS (positive-ion): Calcd. for C$_{26}$H$_{43}$O$_5$: 435.3110. Observed: 435.3110.

Production Example 10

Synthesis of (2R,3R,4R)-1-(t-butyldimethylsilyloxy)-3,4-dihydroxy-2-(4-methoxybenzyloxy)-11-octadecyne (Compound 14)

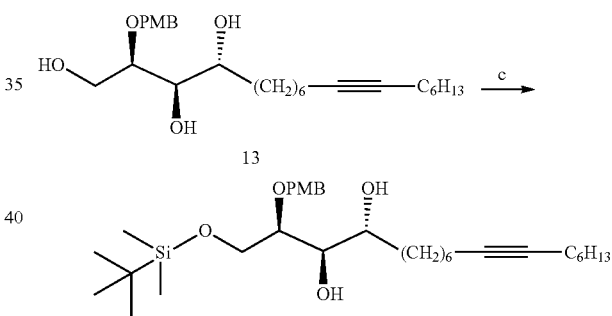

(Step c)

To a solution of compound 13 (2.10 g, 4.83 mmol) in dichloromethane (50 ml) was added t-butyldimethylsilyl chloride (901 mg, 5.85 mmol) and N,N-dimethyl-4-aminopyridine (DMAP) (716 mg, 5.80 mmol), and the mixture was stirred for 3 hr at room temperature, and diluted with dichloromethane. The solvent layer was washed with water and saturated brine, dried over magnesium sulfate, filtered and concentrated under reduced pressure. The residue was purified by silica gel column chromatography and eluted with hexane-ethyl acetate (2:1) to give the title compound 14 (2.47 g, 93%) as a gum-like compound.

IR νmax(KCl) 3504 (broad), 2934, 2859, 1614, 1515 cm$^{-1}$. 400 MHz $^1$H NMR (CDCl$_3$) δ 0.09 (6H, s), 0.89 (3H, t, J=6.8 Hz), 0.91 (9H, s), 1.25-1.60 (18H, m), 2.14 (4H, t, J=7.0 Hz), 2.30 (1H, d, J=7.2 Hz, OH), 3.50 (1H, m), 3.61 (1H, m), 3.72 (1H, m), 3.81 (3H, s), 3.84-3.89 (2H, m), 4.52, 4.71 (2H, AB$_q$, J=11.2 Hz), 6.89 (2H, d, J=8.8 Hz), 7.24 (2H, d, J=8.8 Hz). FABMS (positive-ion): m/z 571 [M+Na]$^+$ (on addition of NaI). HRFABMS (positive-ion): Calcd. for $C_{32}H_{56}O_5SiNa$: 571.3794. Observed: 579.3753.

Production Example 11

Synthesis of (2R,3R,4R)-1-(t-butyldimethylsilyloxy)-3,4-O-isopropylidene-2-(4-methoxybenzyloxy)-11-octadecyne (Compound 15)

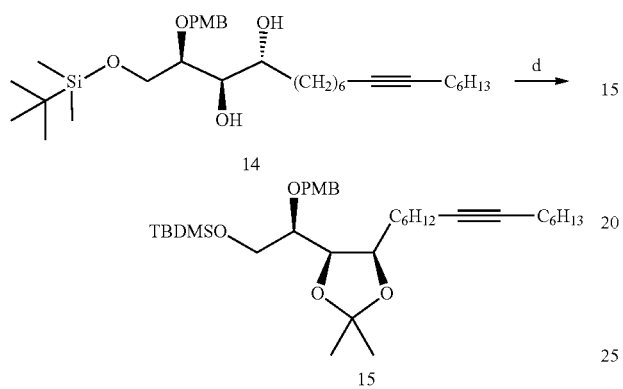

(Step d)

To a solution of compound 14 (2.25 g, 4.10 mmol) in 2,2-dimethoxypropane (30 ml) was added p-TsOH.H$_2$O (60 mg, 0.32 mmol), and the mixture was stirred for 1 hr at room temperature and diluted with ethyl acetate. The solvent layer was washed with saturated aqueous sodium hydrogen carbonate and saturated brine, dried over magnesium sulfate, filtered and concentrated under reduced pressure. The residue was purified by silica gel column chromatography and eluted with hexane-ethyl acetate (9:1) to give the title compound 15 (2.30 g, 95%) as an oil compound.

IR vmax(KCl) 2934, 2856, 1615, 1515, 1249 cm$^{-1}$. 400 MHz $^1$H NMR (CDCl$_3$) δ 0.06 (6H, s), 0.89 (3H, t, J=6.8 Hz, and 9H, s), 1.25-1.65 (24H, m, containing two 3H, singlets at 1.35 and 1.46 ppm), 2.12-2.14 (4H, m), 3.51 (1H, m), 3.68 (1H, m), 3.75 (1H, m), 3.80 (3H, s), 4.14 (1H, m), 4.15 (1H, m), 4.63, 4.68 (2H, AB$_q$, J=11.6 Hz), 6.86 (2H, d, J=8.8 Hz), 7.30 (2H, d, J=8.8 Hz). FABMS (positive-ion): m/z 611 [M+Na]$^+$ (on addition of NaI). HRFABMS (positive-ion): Calcd. for $C_{35}H_{60}O_5SiNa$: 611.4108. Observed: 611.4108.

Production Example 12

Synthesis of (2R,3S,4R)-1-(t-butyldimethylsilyloxy)-2-hydroxy-3,4-O-isopropylidene-11-octadecyne (Compound 16)

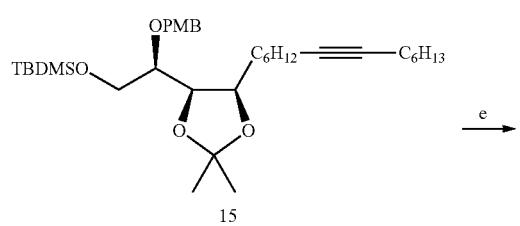

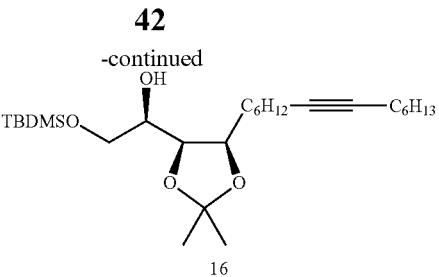

(Step e)

To a solution of compound 15 (2.02 g, 3.68 mmol) in dichloromethane (60 ml) was added H$_2$O (6 ml) and 2,3-dichloro-5,6-dicyano-p-benzoquinone (DDQ) (2.02 g, 8.90 mmol), and the mixture was stirred for 1 hr at room temperature, diluted with dichloromethane, washed with saturated aqueous sodium hydrogen carbonate and saturated brine, dried over magnesium sulfate, filtered and concentrated under reduced pressure. The residue was purified by silica gel column chromatography and eluted with hexane-ethyl acetate (9:1) to give the title compound 16 (1.60 g, 93%) as an oil compound.

IR vmax(KCl) 3570, 2932, 2858, 1463, 1370 cm$^{-1}$. 400 MHz $^1$H NMR (CDCl$_3$) δ 0.07 (6H, s), 0.88 (3H, t, J=7.0 Hz), 0.90 (9H, s), 1.23-1.58 (23H, m, containing two 3H, singlets at 1.34 and 1.49 ppm), 1.77 (1H, m), 2.23-2.15 (4H, m), 2.30 (1H, d, J=5.2 Hz, OH), 3.56-3.67 (3H, m), 4.12-4.19 (2H, m). EIMS (positive-ion): m/z 453 [M−CH$_3$]$^+$, 468 [M]$^+$. HREIMS (positive-ion): Calcd. for $C_{27}H_{52}O_4Si$: 468.3635. Observed: 468.3617.

Production Example 13

Synthesis of (2S,3R,4R)-2-benzoyloxy-1-(t-butyldimethylsilyloxy)-3,4-O-isopropylidene-11-octadecyne (Compound 17)

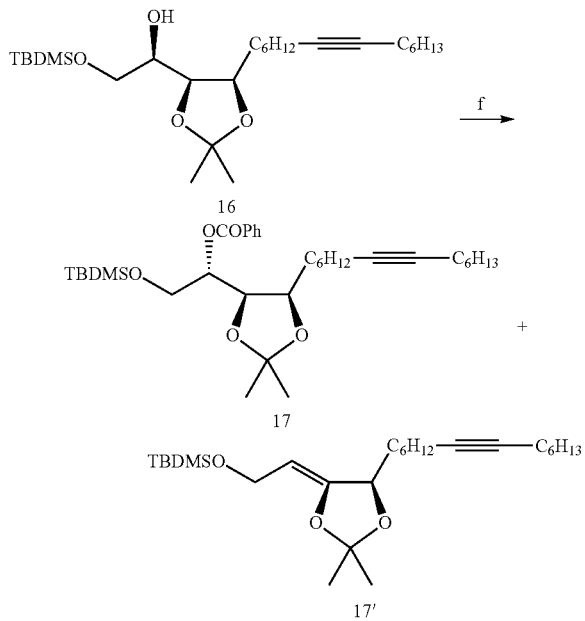

(Step f)

To a solution of compound 16 (1.48 g, 3.15 mmol), triphenylphosphine (PPh$_3$) (4.13 g, 15.75 mmol), benzoic acid (PhCOOH) (1.69 g, 13.86 mmol) in THF (40 ml) was added diethyl azodicarboxylate (DEAD) (2.2M toluene solution, 6.30 ml, 13.86 mmol) at −20° C., and after 30 min, the mixture was slowly warmed to room temperature, stirred overnight (16 hr) and concentrated under reduced pressure. The residue was purified by silica gel column chromatography and eluted with hexane-ethyl acetate (19:1) to give the title compound 17 (1.32 g, 72%) as an oil mixture containing a small amount of byproduct (compound 17') (0.26 g). This mixture was directly used for the next reaction. A part of the mixture was developed with hexane-ethyl acetate (9:1) and using a silica gel TLC plate for separation, whereby compounds 17 and 17' were isolated and purified.

IR vmax(KBr) 2932, 2844, 1724 cm$^{-1}$. 400 MHz $^1$H NMR (CDCl$_3$) δ −0.03 (3H, s), −0.01 (3H, s), 0.84 (9H, s), 0.88 (3H, t, J=7.0 Hz), 1.12-1.55 (24H, m, containing two 3H, singlets at 1.36 and 1.45 ppm), 2.01 (1H, t, J=7.0 Hz), 2.12 (2H, t, J=7.2 Hz), 3.93 (1H, dd, J=4.8, 11.6 Hz), 3.99 (1H, dd, J=2.4, 11.6 Hz), 4.18 (1H, m), 4.42 (1H, dd, J=5.2, 8.8 Hz), 5.15 (1H, m), 7.45 (2H, t, J=7.6 Hz), 7.57 (1H, t, J=7.6 Hz), 8.04 (2H, d, J=7.6 Hz). EIMS (positive-ion): m/z 557, 572 [M]$^+$. HREIMS (positive-ion): Calcd. for C$_{34}$H$_{56}$O$_5$Si: 572.3897. Observed: 572.3896.

Production Example 14

Synthesis of (2S,3S,4R)-1-(t-butyldimethylsilyloxy)-2-hydroxy-3,4-O-isopropylidene-1'-octadecyne (Compound 18)

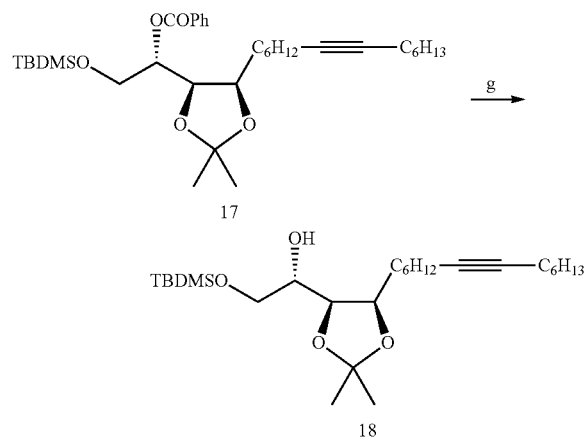

(Step g)

To a solution of compound 17 (1.34 g, 2.34 mmol) in methanol (72 ml) was added sodium methoxide (NaOMe) (1M methanol solution, 8.0 ml, 8.0 mmol), and the mixture was stirred at room temperature overnight (16 hr). The mixture was concentrated under reduced pressure to ⅓, diluted with ethyl acetate, washed with water and saturated brine, dried over magnesium sulfate, filtered and concentrated under reduced pressure. The residue was purified by silica gel column chromatography and eluted with hexane-ethyl acetate (39:1, further 9:1) to give the title compound 18 (840 mg, 77%) as an oil compound.

IR vmax(KCl) 3575 (w), 2932, 2858, 1461 cm$^{-1}$. 400 MHz $^1$H NMR (CDCl$_3$) δ 0.89 (3H, t, J=7.2 Hz), 0.91 (9H, s), 1.25-1.73 (24H, m, containing two 3H, singlets at 1.31 and 1.39 ppm), 2.12 (4H, t, J=7.2 Hz), 2.58 (1H, d, J=4.4 Hz, OH), 3.64-3.67 (2H, m), 3.83 (1H, m), 3.91 (1H, m), 4.17 (1H, m).

EIMS: m/z 453, 468 [M]$^+$. HREIMS: Calcd. for C$_{27}$H$_{52}$O$_4$Si: 468.3635. Observed: 468.3635.

Production Example 15

Synthesis of (2S,3S,4R)-1,2-dihydroxy-3,4-O-isopropylidene-11-octadecyne (Compound 19)

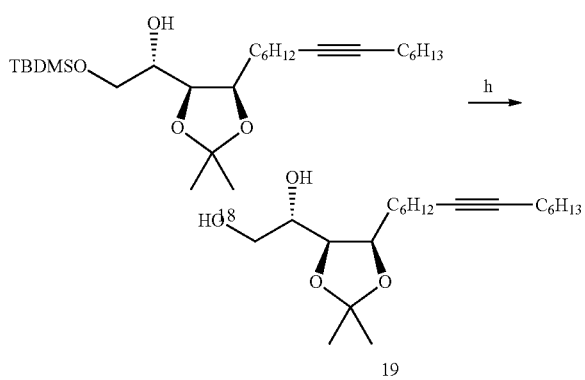

(Step h)

To a solution of compound 18 (4.34 g, 9.26 mmol) in THF (85 ml) was added tetrabutylammonium fluoride (n-Bu$_4$NF) (1M THF solution, 15.0 ml, 15.0 mmol), and the mixture was stirred at room temperature for 45 min. The mixture was concentrated under reduced pressure to ⅓, diluted with ethyl acetate, washed with water and saturated brine, dried over magnesium sulfate, filtered and concentrated under reduced pressure. The residue was purified by silica gel column chromatography and eluted with hexane-ethyl acetate (3:1, further 1:1) to give the title compound 19 (2.49 g, 76%) as an oil compound.

IR vmax(KBr) 3426 (broad), 2932, 2858 cm$^{-1}$. 400 MHz $^1$H NMR (CDCl$_3$) δ 0.89 (3H, t, J=6.8 Hz), 1.20-1.75 (24H, m, containing two 3H, singlets at 1.32 and 1.41 ppm), 1.96 (1H, t, J=5.4 Hz, OH), 2.13 (1H, d, J=5.6 Hz, OH), 2.14 (1H, t, J=6.6 Hz), 3.72-3.77 (2H, m), 3.83 (1H, m), 3.97 (1H, dd, J=5.8, 8.2 Hz). EIMS: m/z 339, 354 [M]$^+$. HREIMS: Calcd. for C$_{21}$H$_{38}$O$_4$: 354.2770. Observed: 354.2766.

Example 1

Synthesis of (2S,3S,4R)-2-hydroxy-3,4-O-isopropylidene-11-octadecyn-1-yl 4,6-O-benzylidene-2,3-di-O-(4-methoxybenzyl)-α-D-galactopyranoside (Compound 20) and (2S,3S,4R)-2-hydroxy-3,4-O-isopropylidene-11-octadecyn-1-yl 4,6-O-benzylidene-2,3-di-O-(4-methoxybenzyl)-β-D-galactopyranoside (Compound 20')

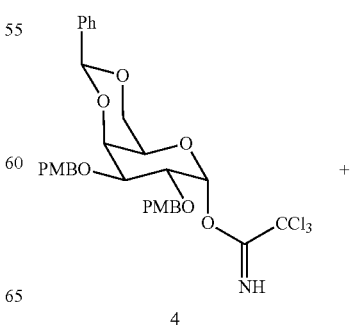

4

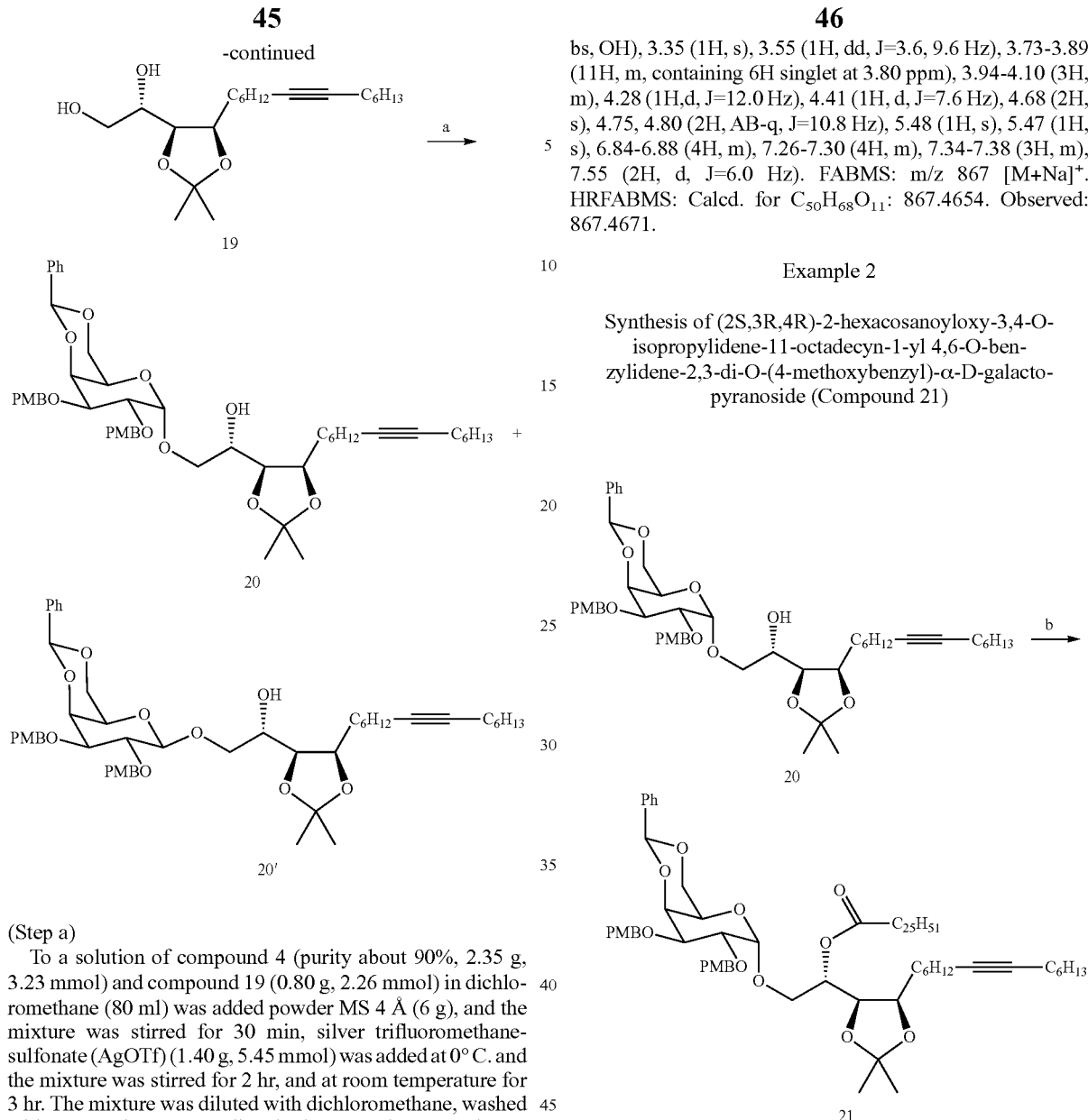

(Step a)

To a solution of compound 4 (purity about 90%, 2.35 g, 3.23 mmol) and compound 19 (0.80 g, 2.26 mmol) in dichloromethane (80 ml) was added powder MS 4 Å (6 g), and the mixture was stirred for 30 min, silver trifluoromethanesulfonate (AgOTf) (1.40 g, 5.45 mmol) was added at 0° C. and the mixture was stirred for 2 hr, and at room temperature for 3 hr. The mixture was diluted with dichloromethane, washed with saturated aqueous sodium hydrogen carbonate and saturated brine, dried over magnesium sulfate, filtered and concentrated under reduced pressure. The residue was purified by silica gel column chromatography and eluted with hexane-ethyl acetate (3:1, then 2:1) to give the title compound 20 (1.16 g, 61%) and compound 20' (0.60 g, 31%) as gum-like compounds each as purified products.

physical constants of compound 20: IR νmax(KBr) 3501 (broad), 2930, 2850, 1613, 1514 cm$^{-1}$. 400 MHz $^1$H NMR (CDCl$_3$) δ 0.86-0.91 (3H, m), 1.22-1.71 (24H, m, containing two 3H, singlets at 1.31 and 1.38 ppm), 2.12-2.16 (4H, m), 3.30 (1H, bs, OH), 3.44 (1H, m), 3.67 (1H, s), 3.77 (1H, m), 3.80 (3H, s), 3.81 (3H, s), 3.89 (1H, m), 3.95-4.07 (4H, m), 4.13-4.22 (3H, m), 4.68, 4.72 (2H, AB$_{-q}$, J=11.8 Hz), 4.96 (1H, d, J=3.6 Hz, anomeric H), 5.47 (1H, s), 6.83-6.88 (4H, m), 7.24-7.27 (2H, m), 7.31-7.37 (5H, m), 7.50-7.53 (2H, m). FABMS: m/z 867 [M+Na]$^+$. HRFABMS: Calcd. for C$_{50}$H$_{68}$O$_{11}$Na: 867.4654. Observed: 867.4657.

physical constants of compound 20': IR νmax(KBr) 3439, 2931, 2859, 1614, 1515 cm$^{-1}$. 400 MHz $^1$H NMR (CDCl$_3$) δ 0.86-0.91 (3H, m), 1.28-1.63 (24H, m, containing two 3H, singlets at 1.33 and 1.41 ppm), 2.11-2.15 (4H, m), 3.33 (1H, bs, OH), 3.35 (1H, s), 3.55 (1H, dd, J=3.6, 9.6 Hz), 3.73-3.89 (11H, m, containing 6H singlet at 3.80 ppm), 3.94-4.10 (3H, m), 4.28 (1H,d, J=12.0 Hz), 4.41 (1H, d, J=7.6 Hz), 4.68 (2H, s), 4.75, 4.80 (2H, AB-q, J=10.8 Hz), 5.48 (1H, s), 5.47 (1H, s), 6.84-6.88 (4H, m), 7.26-7.30 (4H, m), 7.34-7.38 (3H, m), 7.55 (2H, d, J=6.0 Hz). FABMS: m/z 867 [M+Na]$^+$. HRFABMS: Calcd. for C$_{50}$H$_{68}$O$_{11}$: 867.4654. Observed: 867.4671.

Example 2

Synthesis of (2S,3R,4R)-2-hexacosanoyloxy-3,4-O-isopropylidene-11-octadecyn-1-yl 4,6-O-benzylidene-2,3-di-O-(4-methoxybenzyl)-α-D-galactopyranoside (Compound 21)

(Step b)

A suspension of compound 20 (594 mg, 0.70 mmol), cerotic acid (1.29 g, 3.25 mmol), DMAP (1.80 g, 14.73 mmol) and 1-[3-(dimethylamino)propyl]-3-ethylcarbodiimide hydrochloride (WSC hydrochloride (2.87 g, 14.97 mmol)) in THF-dichloromethane (1:1, 50 ml) was stirred at room temperature for 5 days. The mixture was diluted with trichloromethane, washed with water and saturated brine, dried over magnesium sulfate, filtered and concentrated under reduced pressure. The residue was purified by silica gel column chromatography and eluted with hexane-ethyl acetate (5:1) to give the title compound 21 (270 mg, 31%) as a wax-like substance, and further eluted with hexane-ethyl acetate (1:2) to recover the starting compound 20 (121 mg, 20%) as a gum-like compound.

physical constants of compound 21: IR νmax(KBr) 2920, 2851, 1741, 1614, 1588 (w), 1515, 1469 cm$^{-1}$. 400 MHz $^1$H NMR (CDCl$_3$) δ 0.85-0.91 (6H, m), 1.20-1.60 (70H, m, containing two 3H, singlets at 1.33 and 1.41 ppm), 2.13 (4H, t, J=6.8 Hz), 2.24 (2H, dt, J=2.7, 8.0 Hz), 3.63 (1H, s), 3.71 (1H, dd, J=6.0, 12.0 Hz), 3.80 (6H, s), 3.87-4.04 (4H, m), 4.09-4.25 (4H, m), 4.60, 4.72 (2H, AB$_{-q}$, J=11.2 Hz), 4.64, 4.73 (2H, AB$_{-q}$, J=11.4 Hz), 4.95 (1H, d, J=3.2 Hz, anomeri H), 5.02 (1H, m), 5.46 (1H, s), 6.83-6.86 (4H, m), 7.26-7.35 (7H, m), 7.51 (2H, d, J=5.6 Hz). FABMS: m/z 1245 [M+Na]$^+$. HRFABMS: Calcd. for $C_{76}H_{118}O_{12}Na$: 1245.8515. Observed: 1245.8510.

Example 3

Synthesis of (2S,3R,4R)-2-hexacosanoyloxy-3,4-O-isopropylidene-11-octadecyn-1-yl 4,6-O-benzylidene-α-D-galactopyranoside (Compound 22)

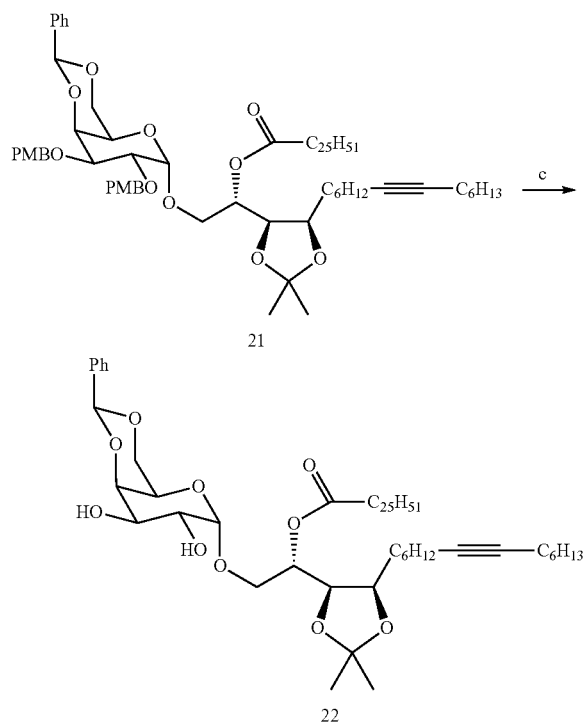

(Step c)

To a solution of compound 21 (265 mg, 0.22 mmol) in dichloromethane-water (10:1, 22 ml) was added DDQ (265 mg, 1.17 mmol), and the mixture was stirred for 3 hr at room temperature, diluted with dichloromethane, washed with saturated aqueous sodium hydrogen carbonate (twice) and saturated brine, dried over magnesium sulfate, filtered and concentrated under reduced pressure. The residue was purified by silica gel column chromatography and eluted with hexane-ethyl acetate (3:1, further 3:2) to give the title compound 22 (167 mg, 78%) as a wax-like substance.

IR vmax(KBr) 3395 (broad), 2921, 2851, 1725 cm$^{-1}$. 400 MHz $^1$H NMR (CDCl$_3$) δ 0.86-0.91 (6H, m), 1.20-1.63 (70H, m, containing two 3H, singlets at 1.34 and 1.43 ppm), 2.13 (4H, t, J=7.2 Hz), 2.30 (2H, dt, J=4.4, 7.2 Hz), 2.39 (2H, bs, OH), 3.73-3.77 (2H, m), 3.82 (2H, bs), 4.03-4.28 (6H, m), 5.01 (1H, s, anomeric H), 5.05 (1H, dt, J=1.5, 7.0 Hz), 5.55 (1H, s), 7.36-7.37 (3H, m), 7.48-7.49 (2H, m). FABMS: m/z 1005 [M+Na]$^+$. HRFABMS: Calcd. for $C_{60}H_{102}O_{10}Na$: 1005.7365. Observed: 1005.7387.

Reference Example 1

Synthesis of 2,3,4-tri-O-benzyl-6-O-methyl-α,β-D-galactopyranose (Compound 25)

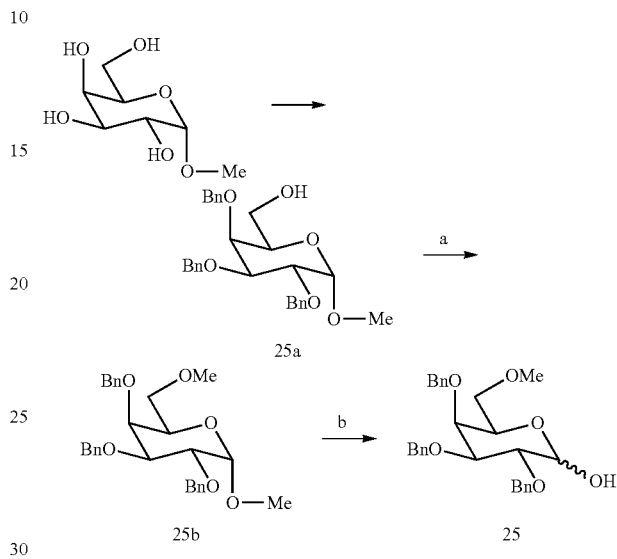

(Step a) Synthesis of Compound 25b

To a solution of compound 25a (1.04 g, 2.24 mmol) produced from methyl α-D-galactopyranoside as a starting material and according to T. J. Lucas et al., Carbohydr. Res., 1975, 39, 39-45 in N,N-dimethylformamide-tetrahydrofuran (1:1, 20 ml) was added sodium hydride (60% mineral oil suspension, 187 mg, 4.68 mmol) under ice-cooling. After stirring for 15 min under ice-cooling, methyl iodide (280 μL, 4.50 mmol) was added, and the mixture was stirred at room temperature for 16 hr. Water was added, and the mixture was extracted with ethyl acetate. The organic layer was washed successively with water and saturated brine, and dried over anhydrous magnesium sulfate. After filtration, the solvent was evaporated by concentration under reduced pressure, and the residue was purified by silica gel column chromatography (30 g, hexane-ethyl acetate=8:1) to give the title compound 25b (839 mg, 78%) as a colorless oil.

IR (film): $v_{max}$=1600, 1500 cm$^{-1}$.

$^1$H NMR (400 MHz, CDCl$_3$): δ=7.42-7.26 (15H, m), 4.96 (1H, d, J=12 Hz), 4.86 (1H, d, J =12 Hz), 4.84 (1H, d, J=12 Hz), 4.74 (1H, d, J=12 Hz), 4.692 (1H, d, J=12 Hz), 4.687 (1H, d, J=3.2 Hz), 4.62 (1H, d, J=12 Hz), 4.04 (1H, dd, J=9.6, 3.2 Hz), 3.94 (1H, dd, J=10, 3.2 Hz), 3.91-3.89 (1H, m), 3.84 (1H, br.t, J=6.4 Hz), 3.44 (1H, dd, J=10, 6.4 Hz), 3.37 (3H, s), 3.34 (1H, dd, J=10, 6.4 Hz), 3.27 (3H, s).

(Step b) Synthesis of Compound 25

To a solution of compound 25b (733 mg, 1.53 mmol) in acetic anhydride (20 mL) was added a solution of concentrated sulfuric acid (0.03 ml) in acetic anhydride (10 mL) under ice-cooling, and the mixture was stirred for 20 min. Saturated aqueous sodium hydrogen carbonate solution was added, and the mixture was neutralized and diluted with ethyl acetate. The organic layer was washed successively with saturated aqueous sodium hydrogen carbonate solution, water and saturated brine, and dried over anhydrous magnesium sulfate. After filtration, the solvent was evaporated by concentration under reduced pressure.

To a solution of the residue in methanol (10 mL) was added sodium methoxide (90 mg, 1.7 mmol) at room temperature, and the mixture was stirred for 30 min. The mixture was acidified with cation exchange resin (Dowex 50W-X8) and filtered, and the solvent was evaporated by concentration under reduced pressure. The residue was purified by silica gel column chromatography (20 g, hexane-ethyl acetate=3:1) to give the title compound 25(652 mg, 92%) as a white powder.
IR (KBr): $\nu_{max}=$3420 1605, 1495 cm$^{-1}$.

Production Example 16

Synthesis of trichloroacetoimidoyl 2,3,4-tri-O-benzyl-6-O-methyl-α,β-D-galactopyranoside (Compound 26)

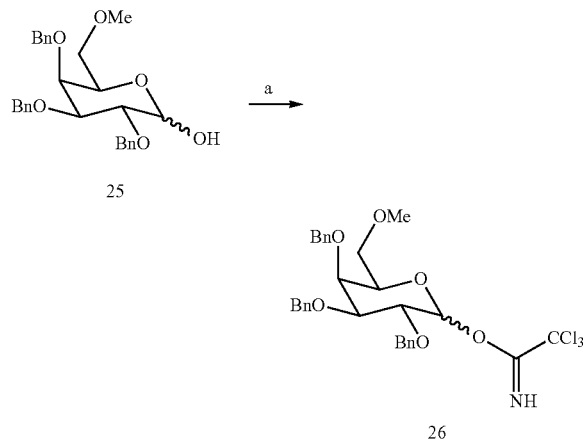

To a solution of compound 25 (465 mg, 1.00 mmol) in dichloromethane (10 ml) were added Cl$_3$CCN (1.44 g, 10 mmol) and cesium carbonate (480 mg, 1.47 mmol), and the mixture was stirred for 16 hr at room temperature, and diluted with dichloromethane. The organic layer was washed with water, saturated aqueous sodium hydrogen carbonate and saturated brine, dried over magnesium sulfate, filtered and concentrated under reduced pressure to give the title compound 26 (600 mg, 98%). This compound 26 was used for the next reaction without purification.

Production Example 17

Synthesis of (2S,3S,4R)-1-(t-butyldimethylsilyloxy)-2-hydroxy-3,4-O-isopropylidene-5(E,Z)-octadecene (Compound 28)

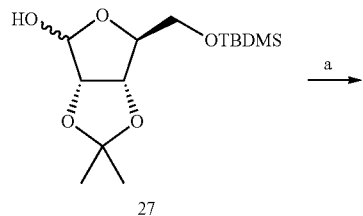

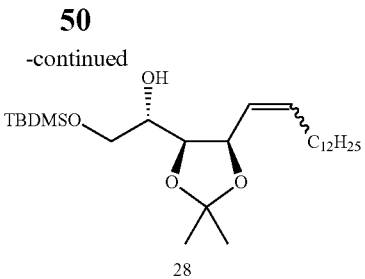

To a solution of tridecyltriphenylphosphonium bromide (12.29 g, 23.38 mmol) in THF (25 ml) was added n-BuLi (1.6M hexane, 14.7 ml, 23.53 mmol) at −10° C. and the mixture was stirred for 30 min. A solution of a compound known in a literature (J. C. Tadav, S. Pamu, D. C. Bhunia, S. Pabberaja, Synlett. 2007, 992-994.) (compound 27) (2.37 g, 7.79 mmol) obtained from L-ribose by 2 steps in THF (20 ml) was added dropwise, and the mixture was stirred at room temperature for 3 hr. The reaction was quenched with methanol, and the mixture was diluted with hexane-ethyl acetate (1:1), washed with water and saturated brine, dried over magnesium sulfate, filtered and concentrated under reduced pressure. The residue was purified by silica gel column chromatography and eluted with hexane-ethyl acetate (19:1) to give the title compound 28 (3.17 g, 86%) as a double bond E,Z isomer (1:1) oil mixture. The double bond E,Z isomers were separated using a preparative silica gel TLC plate for partial physical data.

E-isomer: IR vmax(KBr) 3420, 2925, 2854, 1465 cm$^{-1}$. 400 MHz $^1$H NMR (CDCl$_3$) δ 0.09 (6H, s), 0.89 (3H, t, J=7.2 Hz), 0.91 (9H, s), 1.25 (20H, bs), 1.34 (3H, s), 1.35-1.42 (2H, m), 1.45 (3H, s), 1.99 (2H, q, J=6.8 Hz), 2.37 (1H, d, J=4.4 Hz, OH), 3.65-3.71 (2H, m), 3.81 (1H, m), 4.01 (1H, dd, J=6.2, 8.6 Hz), 4.64 (1H, t, J=7.0 Hz), 5.61 (1H, dd, J=8.0, 15.6 Hz), 5.81 (1H, dd, J=6.6, 15.6 Hz). EIMS: m/z 453, 468 [M]$^+$. HREIMS: Calcd. for C$_{27}$H$_{54}$O$_4$Si: 470.3791. Observed: 470.3795.

Z-isomer: IR vmax(KBr) 3558, 2927, 2856, 1465 cm$^{-1}$. 400 MHz $^1$H NMR (CDCl$_3$) δ 0.09 (6H, s), 0.88 (3H, t, J=6.8 Hz), 0.90 (9H, s), 1.25 (20H, bs), 1.36 (3H, s), 1.36-1.41 (2H, m), 1.45 (3H, s), 2.07-2.20 (2H, m), 2.46 (1H, d, J=4.8 Hz, OH), 3.66-3.71 (2H, m), 3.81 (1H, dd, J=6.0, 12.8 Hz), 4.02 (1H, dd, J=6.4, 8.4 Hz), 5.01 (1H, m), 5.54 (1H, dd, J=9.6, 11.0 Hz), 5.71 (1H, td, J=7.4, 11.0 Hz).

Production Example 18

Synthesis of (2S,3S,4R)-1,2-dihydroxy-3,4-O-isopropylidene-5(E,Z)-octadecene (Compound 29)

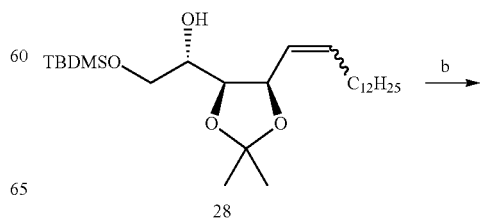

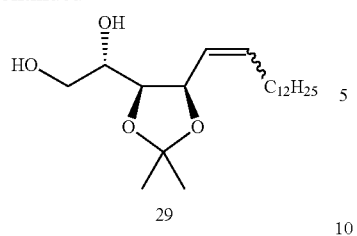

To a solution of compound 28 (3.17 g, 6.73 mmol) in THF (100 ml) was added n-Bu$_4$NF (1M THF solution, 12.0 ml, 12.0 mmol), and the mixture was stirred at room temperature for 45 min. The mixture was concentrated under reduced pressure, diluted with ethyl acetate, washed with water and saturated brine, dried over magnesium sulfate, filtered and concentrated under reduced pressure. The residue was purified by silica gel column chromatography and eluted with hexane-ethyl acetate (9:1, further 2:1) to give compound 29 (2.35 g, 98%) as a double bond E,Z isomer (1:1) oil mixture.

IR vmax(KBr) 3420 (broad), 2925, 2854, 1465 cm$^{-1}$. 400 MHz $^1$H NMR (CDCl$_3$) δ 0.86-0.92 (3H, m), 1.25-1.47 (26H, m, containing two 3H/2, singlets at 1.36 and 1.37 ppm and 3H singlet at 1.47 ppm), 2.02-2.12 (2H, m), 3.70-3.82 (2H, m), 4.05-4.10 (1H, m), 4.67 (0.5H, t, J=7.2 Hz, E-isomer), 5.05 (0.5H, m, Z-isomer), 5.56-5.63 (1H, m), 5.77 (0.5H, m, Z-isomer), 5.91 (0.5H, m, E-isomer).

Example 4

Synthesis of (2S,3S,4R)-2-hydroxy-3,4-O-isopropylidene-5(E,Z)-octadecen-1-yl 2,3,4-tri-O-benzyl-6-O-methyl-α-D-galactopyranoside (Compound 30) and (2S,3S,4R)-2-hydroxy-3,4-O-isopropylidene-5(E,Z)-octadecen-1-yl 2,3,4-tri-O-benzyl-6-O-methyl-β-D-galactopyranoside (Compound 30')

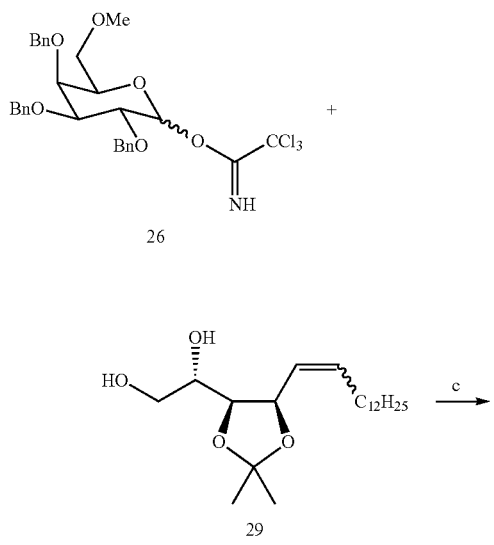

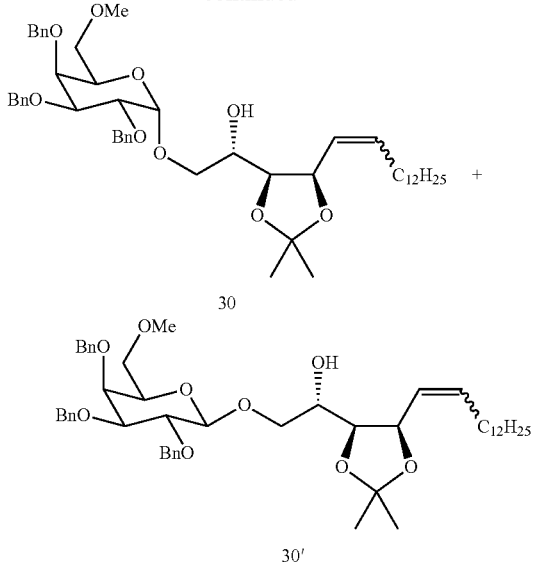

To a solution of imidate (compound 26) (304 mg, 0.50 mmol) and diol (compound 29) (171 mg, 0.48 mmol) in dichloromethane (10 ml) was added MS 4 Å (0.8 g), and the mixture was stirred at room temperature for 30 min. AgOTf (100 mg, 0.39 mmol) was added at −5° C. The mixture was stirred for 1.5 hr, further stirred at room temperature for 30 min, diluted with dichloromethane, washed with saturated aqueous sodium hydrogen carbonate and saturated brine, dried over magnesium sulfate, filtered and concentrated under reduced pressure. The residue was isolated and purified by silica gel column chromatography and eluted with hexane-ethyl acetate (3:1, then 2:1) to give the title compounds 30 (178 mg, 47%) and 30' (183 mg, 48%) as gum-like compounds each as a purified product.

Physical constants of compound 30 (E,Z isomer mixture): IR ν$_{max}$(KBr) 3470 (broad), 2925, 2854, 1455 cm$^{-1}$. 400 MHz $^1$H NMR (CDCl$_3$) δ 0.88 (3H, t, J=6.8 Hz), 1.21-1.60 (26H, m, containing two 3H, singlets at 1.31 and 1.44 ppm), 2.02-2.06 (2H, m), 3.15-3.45 (6H, m, containing 3H, s, at 3.27 ppm), 3.57 (1H, m), 3.85-4.08 (7H, m), 4.58-4.99 (7H, m, containing an anomeric H), 5.46-5.85 (2H, m), 7.26-7.40 (15H, m).

The double bond E,Z isomers were separated using a preparative silica gel TLC plate for partial physical data of compound 30'.

Z-isomer of compound 30': IR ν$_{max}$(KBr) 3481 (broad), 2925, 2854, 1455 cm$^{-1}$. 400 MHz $^1$H NMR (CDCl$_3$) δ 0.88 (3H, t, J=6.8 Hz), 1.20-1.60 (26H, m, containing two 3H, singlets at 1.34 and 1.44 ppm), 2.02 (1H, m), 2.12 (1H, m), 3.25 (3H, s), 3.35-3.38 (2H, m), 3.46-3.54 (3H, m), 3.72 (1H, dd, J=7.4, 11.4 Hz), 3.80-3.87 (3H, m), 3.97 (1H, dd, J=6.2, 8.2 Hz), 4.13 (1H, dd, J=2.0, 11.2 Hz), 4.36 (1H, d, J=8.0 Hz, anomeric H), 4.64, 4.94 (2H, AB-q, J=11.6 Hz), 4.72, 4.75 (2H, AB-q, J=11.6 Hz), 4.81, 4.88 (2H, AB-q, J=11.0 Hz), 4.94 (1H, m), 5.48 (1H, m), 5.63 (1H, m), 7.27-7.36 (15H, m).

E-isomer of compound 30': IR ν$_{max}$(KBr) 3449 (broad), 2924, 2854, 1455 cm$^{-1}$. 400 MHz $^1$H NMR (CDCl$_3$) δ 0.88 (3H, t, J=6.8 Hz), 1.21-1.60 (26H, m, containing two 3H, singlets at 1.32 and 1.44 ppm), 2.02-2.08 (2H, m), 3.26 (3H, s), 3.38 (1H, dd, J=5.2, 8.0 Hz), 3.43-3.55 (4H, m), 3.70 (1H, dd, J=7.4, 11.4 Hz), 3.78-3.87 (3H, m), 3.93 (1H, dd, J=6.0, 8.8 Hz), 4.15 (1H, dd, J=2.0, 8.0 Hz), 4.36 (1H, d, J=7.2 Hz, anomeric H), 4.59 (1H, t, J=6.8 Hz), 4.65, 4.94 (2H, AB-q, J=11.6 Hz), 4.72, 4.75 (2H, AB-q, J=12.0 Hz), 4.81, 4.88 (2H, AB-q, J=11.2 Hz), 5.55 (1H, dd, J=7.4, 15.0 Hz), 5.78 (1H, td, J=7.0, 15.0 Hz), 7.26-7.36 (15H, m).

Example 5

Synthesis of (2S,3R,4R)-2-hexacosanoyloxy-3,4-O-isopropylidene-5(E,Z)-octadecen-1-yl 2,3,4-tri-O-benzyl-6-O-methyl-α-D-galactopyranoside (Compound 31)

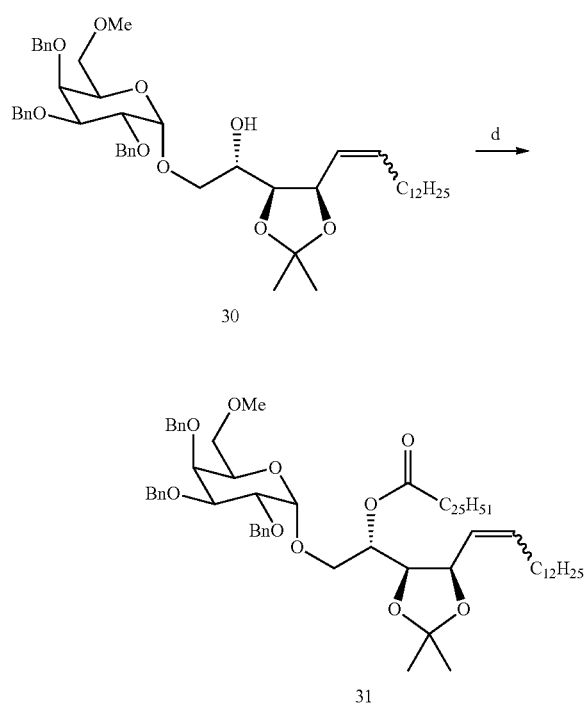

A suspension of compound 30 (127 mg, 0.16 mmol), cerotic acid (126 mg, 0.32 mmol), DMAP (194 mg, 1.59 mmol) and WSC hydrochloride (305 mg, 1.59 mmol) in THF-dichloromethane (1:1, 14 ml) was stirred at room temperature for 3 days. The suspension was diluted with trichloromethane, washed with water and saturated brine, dried over magnesium sulfate, filtered and concentrated under reduced pressure. The residue was purified by silica gel column chromatography and eluted with hexane-ethyl acetate (9:1, further 7:1) to give the title compound 31 (75 mg, 40%) as a wax-like substance.

IR $\nu_{max}$(KBr) 2919, 2850, 1738, 1468 cm$^{-1}$. 400 MHz $^1$H NMR (CDCl$_3$) δ 0.88 (6H, t, J=6.8 Hz), 1.20-1.60 (72H, m, containing isopropylidene two methyl protons), 1.98-2.22 (4H, m), 3.25 (3H, s), 3.36, 3.39 (2H, AB-q, J=10.0 Hz), 3.66 (1H, m), 3.83-3.95 (4H, m), 4.03 (1H, dd, J=3.6, 10.0 Hz), 4.36 (1H, dd, J=8.2, 14.6 Hz), 4.54-5.00 (8H, m, containing anomeric H, doublet J=3.6 Hz at 4.89 ppm), 4.64, 4.73 (2H, AB-q, J=11.4 Hz), 4.95 (1H, d, J=3.2 Hz, anomeric H), 5.02 (1H, m), 5.01 (1H, m), 5.34-5.80 (2H, m), 7.26-7.39 (15H, m).

Example 6

Synthesis of (2S,3R,4R)-3,4-dihydroxy-2-hexacosanoyloxy-11-octadecyn-1-yl α-D-galactopyranoside (Compound 23)

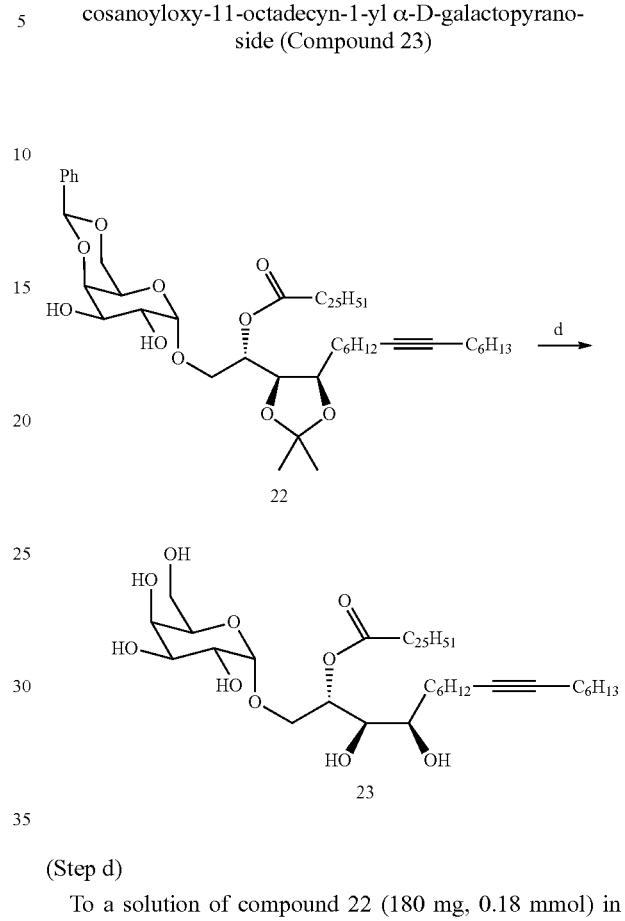

(Step d)

To a solution of compound 22 (180 mg, 0.18 mmol) in dichloromethane-acetonitrile (1:1, 70 ml) was added water (508 mg, 28.2 mmol) and 46% aqueous HF (196 mg, 4.56 mmol), and the mixture was stirred at room temperature for 0.5 hr, diluted with trichloromethane, washed with saturated aqueous sodium hydrogen carbonate and saturated brine, dried over magnesium sulfate, filtered and concentrated under reduced pressure. The residue was purified by silica gel column chromatography and eluted with trichloromethane-methanol (19:1, further 37:3) to give the title compound 23.

The physical constants of compound 23 obtained in this step were the same as those of the following compound 23.

Example 7

Synthesis of (2S,3R,4R)-3,4-dihydroxy-2-hexacosanoyloxyoctadecyl α-D-galactopyranoside (Compound 24)

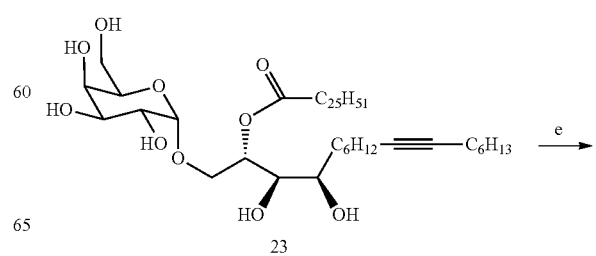

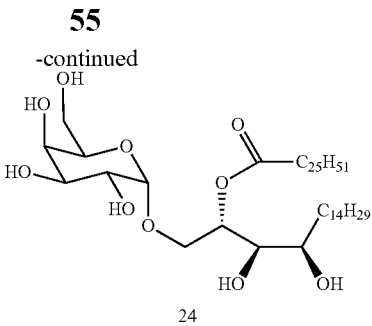

(Step e)

In a solution of compound 23 (34 mg, 0.04 mmol) in trichloromethane-methanol (1:1, 20 ml) was suspended 20% Pd(OH)$_2$ carbon (34 mg), and the mixture was stirred in a hydrogen stream at room temperature for 4 hr and filtered. The catalyst was washed well with trichloromethane-methanol (1:1), and the collected filtrate was concentrated. The crude residue was purified by a thin layer silica gel plate for separation [developed with trichloromethane-methanol (7:1)] to give the title compound 24 (26 mg, 76%) as a wax-like substance.

The physical constants of compound 24 obtained in this step were the same as those of the following compound 24.

Example 8

Synthesis of (2S,3R,4R)-2-hexacosanoyloxy-3,4-O-isopropylideneoctadecyl 6-O-methyl-α-D-galactopyranoside (Compound 32)

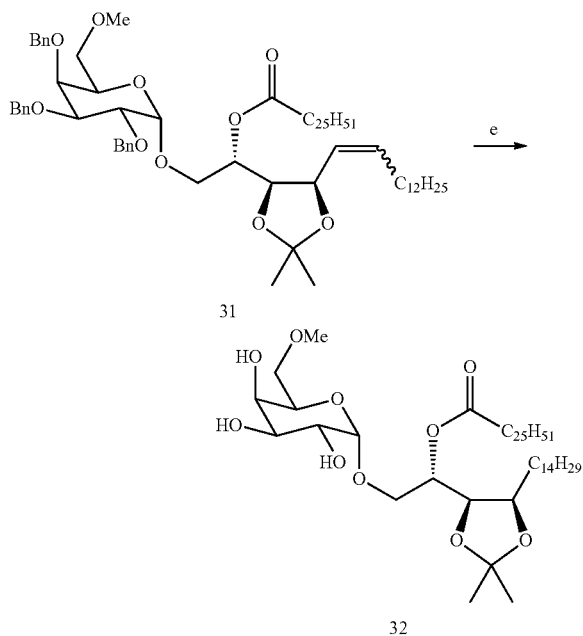

To a solution of compound 31 (62 mg, 0.05 mmol) in ethyl acetate (20 ml) was added 20% Pd(OH)$_2$ carbon (31 mg), and the mixture was stirred in a hydrogen stream at room temperature for 16 hr, and the catalyst was filtered off. The filtrate was distilled away under reduced pressure. The residue was purified by a preparative thin layer silica gel plate and developed with hexane-ethyl acetate (1:4) to give the title compound 32 (20 mg, 42%).

IR $v_{max}$(KBr) 3814 (broad), 2919, 2851, 1732, 1470 cm$^{-1}$. 400 MHz $^1$H NMR (CDCl$_3$) δ 0.86-0.90 (6H, m), 1.25-1.59 (78H, m, containing two 3H, singlets at 1.34 and 1.43 ppm), 2.26-2.33 (2H, m), 2.34 (1H, bs, OH), 2.56 (1H, broad s, OH), 3.00 (1H, bs, OH), 3.41 (3H, s), 3.67-3.75 (4H, m), 3.82 (1H, m), 3.93 (1H, t, J=4.8 Hz), 4.04 (1H, dd, J=1.8, 11.4 Hz), 4.07 (1H, bs), 4.13-4.20 (2H, m), 4.92 (1H, d, J=3.6 Hz, anomeri H), 5.04 (1H, m). [α]$_D^{26}$ +40.9° (c 0.9, CHCl$_3$).

Example 9

Synthesis of (2S,3R,4R)-3,4-dihydroxy-2-hexacosanoyloxyoctadecyl 6-O-methyl-α-D-galactopyranoside (Compound 33)

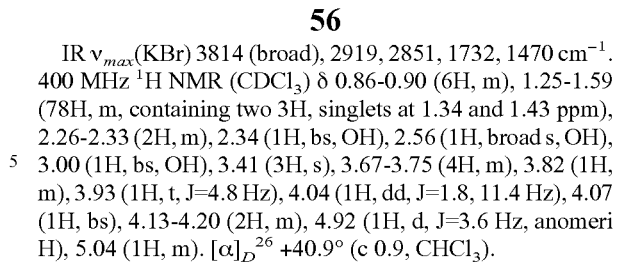

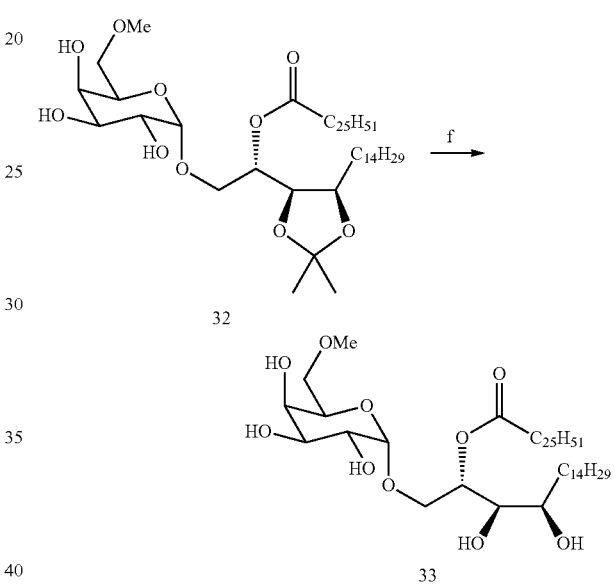

To a solution of compound 32 (50 mg, 0.06 mmol) in dichloromethane-MeCN (1:1, 20 ml) were added water (50 mg, 28.2 mmol) and 46% aqueous HF (25 mg, 0.58 mmol), and the mixture was stirred at room temperature for 10 min. The reaction product was diluted with trichloromethane, washed with saturated aqueous sodium hydrogen carbonate and saturated brine, dried over magnesium sulfate, filtered and concentrated under reduced pressure. The residue was purified by preparative thin layer chromatography and developed with CHCl$_3$-MeOH (7:1) to give the title compound 33 (29 mg, 61%) as a wax-like substance.

[α]$_D^{26}$+54.5° (c 0.78, CHCl$_3$-CH$_3$OH (12:1));

IR $v_{max}$(KBr) 3383 (broad), 2919, 2850, 1734, 1468 cm$^{-1}$. 400 MHz $^1$H NMR (CDCl$_3$-CD$_3$OD, 19:1) δ 0.88 (6H, t, J=6.8 Hz), 1.20-1.62 (72H, m), 2.32 (2H, t, J=7.6 Hz), 3.40 (3H, s), 3.62-3.67 (3H, m), 3.74-3.81 (2H, m), 3.81-3.88 (2H, m), 3.96 (1H, d, J=5.4 Hz), 4.00 (1H, d, J=3.0 Hz), 4.04 (1H, dd, J=4.0, 11.2 Hz), 4.93 (1H, d, J=3.6 Hz, anomeric H), 5.08 (1H, m). 125 MHz $^{13}$C NMR (CDCl$_3$-CD$_3$OD, 12:1) 14.07, 22.66, 24.90, 25.90, 29.19, 29.33, 29.35, 29.51, 29.63, 29.67, 29.70, 31.90, 34.34, 59.35, 67.29, 69.06, 70.02, 71.79, 71.88, 72.52, 72.87, 99.24, 173.25. FABMS; m/z 895.7 [M+Na]$^+$. HRFABMS; calcd. For C$_{51}$H$_{100}$O$_{10}$Na: 895.7214; observed: 895.7213.

The above-mentioned compound 23 can also be produced by the following method.

Production Example 19

Synthesis of 4-methylphenyl 4,6-O-(4-methoxyben-zylidene)-2,3-di-O-(4-methoxybenzyl)-1-thio-β-D-galactopyranoside (Compound 43)

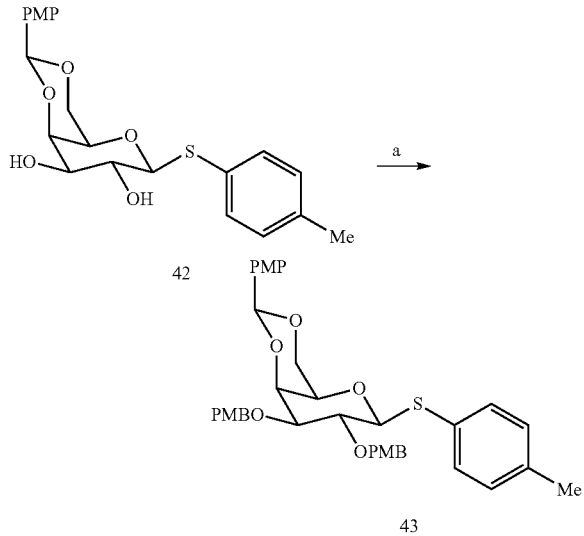

(Step a)

To a solution of a compound 42 known in a literature (S. Roy, A. Chakraborty and R. Ghosh, Carbohydr. Res., 2008, 343, 2523-2529.) (23.285 g, 57.487 mmol) and 4-methoxy-benzyl chloride (19 g, 121.32 mmol) in N,N-dimethylformamide (DMF) (150 ml) were added sodium hydride (60% oil dispersion, 5.1 g, 127.5 mmol) and tetrabutylammonium iodide (1 g). The mixture was heated to 70° C. over 60 min, and cooled to room temperature. Ice (100 g) was added and the mixture was extracted with ethyl acetate. The organic layer was washed with water and saturated brine, dried over magnesium sulfate, filtered and concentrated under reduced pressure and purified by silica gel column chromatography (eluted with hexane-ethyl acetate (1:1)) to give the title compound 43 (31.2 g, 84%) as crystals.

270 MHz $^1$H NMR (CDCl$_3$) δ. 2.31 (3H, s), 3.36 (1H, s), 3.54-4.67 (19H, m, containing three 3H singlets at 3.79, 3.81 and 3.82 ppm), 5.42 (1H, s), 6.81-7.62 (16H, m).

Production Example 20

Synthesis of 4,6-O-isopropylidene-2,3-di-O-4-methoxybenzyl-α-D-galactopyranose (Compound 44)

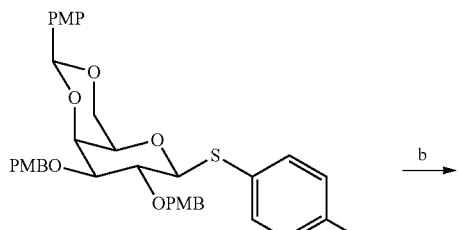

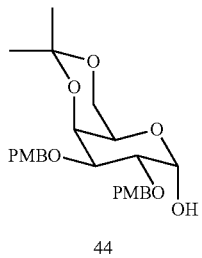

(Step b)

To a solution of compound 43 (31.16 g, 48.32 mmol) in acetone (1000 ml) was added N-bromosuccinimide (NBS) (10.32 g, 57.99 mmol) at −20° C., and the mixture was stirred for 45 min. Powdery ammonium chloride (10 g) and saturated aqueous sodium hydrogen carbonate (100 g) were added, and the mixture was concentrated to 1/5 and extracted with ethyl acetate. The ethyl acetate layer was washed with 10% aqueous Na$_2$S$_2$O$_3$ solution and then brine, dried over magnesium sulfate, filtered and concentrated under reduced pressure. The resulting mixture was purified by silica gel column chromatography and eluted with hexane-ethyl acetate (1:1, further 1:2) to give the title compound 44 (13.5 g, 61%) as an oil.

270 MHz $^1$H NMR (CDCl$_3$) δ 1.34 (3H, s), 1.42 (3H, s), 2.93 (1H, d, J=6.0 Hz, OH) 3.71-4.65 (16H, m, containing two 3H, s, at 3.80 and 3.81 ppm), 5.42 (1H, d, J=6.0 Hz, changed to a singlet on addition of D$_2$O, anomeric H), 6.85-6.91 (4H, m) 7.17-7.54 (4H, m).

Example 10

Synthesis of (2S,3S,4R)-2-hydroxy-3,4-O-isopropy-lidene-11-octadecyn-1-yl 4,6-O-isopropylidene-2,3-di-O-(4-methoxybenzyl)-α-D-galactopyranoside (Compound 45)

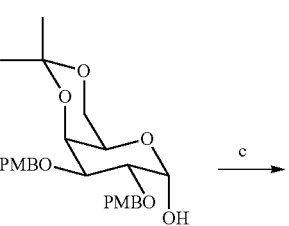

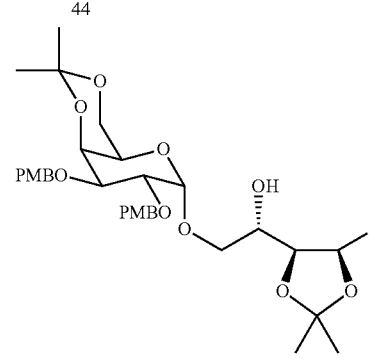

(Step c)

To a solution of compound 44 (460 mg, 1.0 mmol) in dichloromethane (10 ml) were added $Cl_3CCN$ (1.44 g, 10 mmol) and cesium carbonate (480 mg, 1.47 mmol), and the mixture was stirred for 16 hr at room temperature and diluted with dichloromethane. The organic layer was washed with water and saturated brine, dried over magnesium sulfate, filtered and concentrated under reduced pressure to give an imidate of compound 44. (This imidate compound was used for the next reaction without purification.) This imidate compound and compound 19 (170 mg, 0.477 mmol), which is acetylenediol, were dissolved in dichloromethane (25 ml). Thereto was added powder MS 4 Å (1.6 g), and the mixture was stirred for 30 min and further cooled to 0° C. Silver trifluoromethanesulfonate (AgOTf) (200 mg, 0.778 mmol) was added and the mixture was stirred for 1 hr, and further stirred at room temperature for 2 hr. After filtration, the filtrate was washed with dichloromethane, and the organic layer was washed with saturated aqueous sodium hydrogen carbonate and saturated brine, dried over magnesium sulfate, filtered and concentrated under reduced pressure. The residue was purified by silica gel column chromatography and eluted with hexane-ethyl acetate (3:1, 2:1, further 1:1) to give compound 45 (166 mg, 44%) as an oil compound.

IR $v_{max}$(KBr) 3483 (broad), 2980, 2933, 2861, 1612, 1515 $cm^{-1}$. 500 MHz $^1H$ NMR ($CDCl_3$) δ 0.88 (3H, t, J=7.1 Hz), 1.27-1.74 (30H, m, containing four 3H, singlet at 1.31, 1.33, 1.39 and 1.41 ppm), 2.11-2.15 (4H, m), 2.92 (1H, bs, OH), 3.58 (1H, dd, J=6.8, 10.7 Hz), 3.69 (1H, dd, J=7.0, 8.5 Hz), 3.78-4.00 (12H, m, containing two 3H, singlet at 3.81 and 3.821 ppm), 4.07 (1H, dd, J=4.4, 7.1 Hz), 4.11-4.18 (2H, m), 4.49, 4.67 (2H, $AB_{-q}$, J=11.4 Hz), 4.52, 4.57 (2H, $AB_{-q}$, J=11.3 Hz), 4.93 (1H, d, J=4.2 Hz, anomeric H), 6.86-6.91 (4H, m), 7.22 (2H, d, J=8.8 Hz), 7.29 ((2H, d, J=8.6 Hz). ESIMS: m/z 819 [M+Na]$^+$. HRESIMS: Calcd. for $C_{46}H_{68}O_{11}Na$: 819.4654. Observed: 819.4645.

Example 11

Synthesis of (2S,3R,4R)-2-hexacosanoyloxy-3,4-O-isopropylidene-11-octadecyn-1-yl 4,6-O-isopropylidene-2,3-di-O-(4-methoxybenzyl)-α-D-galactopyranoside (Compound 46)

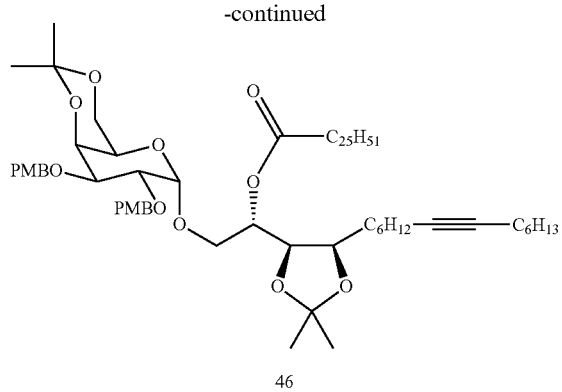

46

(Step d)

A suspension of compound 45 (166 mg, 0.208 mmol), cerotic acid (330 mg, 0.832 mmol), DMAP (509 mg, 4.165 mmol) and 1-[3-(dimethylamino)propyl]-3-ethylcarbodiimide hydrochloride (WSC hydrochloride (800 mg, 4.165 mmol)) in THF-methylene chloride (1:1, 32 ml) was stirred at room temperature for 4 days, diluted with trichloromethane, washed with water and saturated brine, dried over magnesium sulfate, filtered and concentrated under reduced pressure. The residue was purified by silica gel column chromatography and eluted with hexane-ethyl acetate (5:1) to give compound 46 (116 mg, 47%) as a wax-like substance.

IR $v_{max}$(KBr) 2922, 2852, 1737, 1616 (w), 1515 $cm^{-1}$. 500 MHz $^1H$ NMR ($CDCl_3$) δ 0.87-0.89 (6H, m), 1.25-1.68 (76H, m), 2.11-2.14 (4H, m), 2.24-2.31 (2H, m), 3.63 (1H, s), 3.66 (1H, dd, J=4.4, 11.5 Hz), 3.73 (1H, m), 3.77-4.70 (20H, m, containing two 3H, singlets at 3.80 and 3.81 ppm), 5.01 (1H, d, J=4.0 Hz, anomeric H), 5.06 (1H, m), 6.85-6.90 (4H, m), 7.20 (2H, m), 7.30 (2H, m). ESIMS: m/z 1197.85 [M+Na]$^+$. HRESIMS: Calcd. for $C_{72}H_{118}O_{12}Na$: 1197.8516. Observed: 1197.8517.

Example 12

Synthesis of (2S,3R,4R)-2-hexacosanoyloxy-3,4-O-isopropylidene-11-octadecyn-1-yl 4,6-O-isopropylidene-α-D-galactopyranoside (Compound 47)

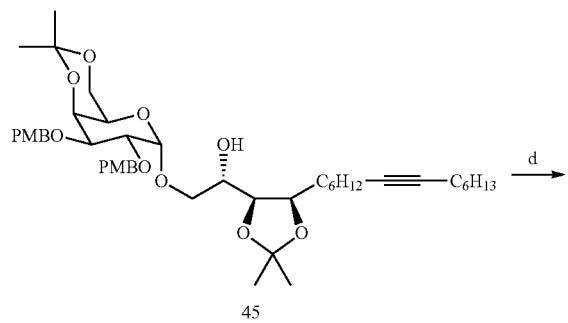

45

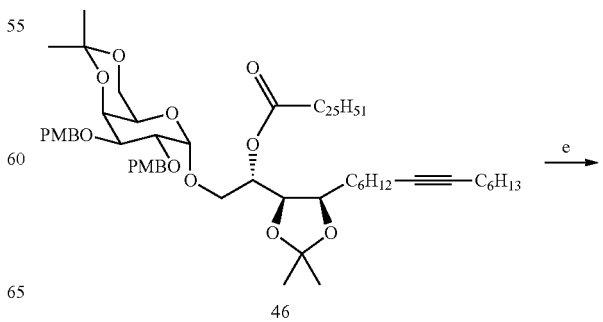

46

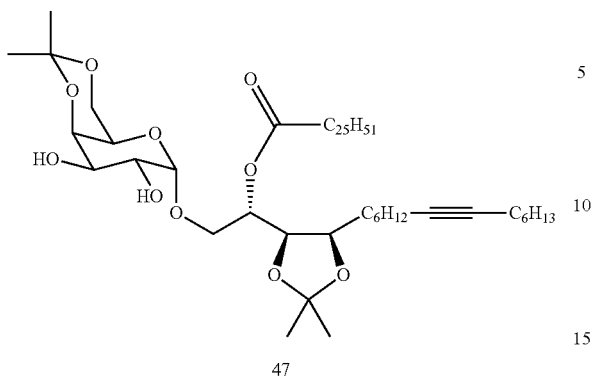

47

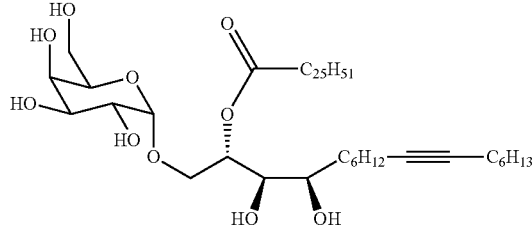

23

(Step e)

To a solution of compound 46 (113 mg, 0.096 mmol) in dichloromethane-water (10:1, 11 ml) was added DDQ (113 mg, 0.498 mmol), and the mixture was stirred for 3 hr at room temperature, diluted with dichloromethane, saturated aqueous sodium hydrogen carbonate (twice) and saturated brine, dried over magnesium sulfate, filtered and concentrated under reduced pressure. The residue was purified by silica gel column chromatography and eluted with hexane-ethyl acetate (2:1, further 3:2) to give the title compound 47 (57 mg, 63%) as a wax-like substance.

IR $\nu_{max}$(KBr) 3483, 3233, 2920, 2851, 1737 cm$^{-1}$. 500 MHz $^1$H NMR (CDCl$_3$) δ 0.87-0.90 (6H, m), 1.21-1.62 (64H, m, containing four 3H, s, at 1.33, 1.37, 1.42 and 1.45 ppm), 2.13 (4H, t, J=7.1 Hz), 2.27-2.32 (2H, m), 3.66 (1H, dd, J=5.7, 11.3 Hz), 3.83 (1H, t, J=7.0 Hz), 3.94 (1H, dd, J=6.7, 8.7 Hz), 3.98-4.04 (3H, m), 4.11 (1H, dd, J=2.1, 11.2 Hz), 4.15-4.18 (2H, m), 4.21 (1H, dd, J=6.6, 13.5 Hz), 4.91 (1H, d, J=4.4 Hz, anomeri H), 5.02 (1H, m). ESIMS: m/z 957.7 [M+Na]$^+$.

HRESIMS: Calcd. for C$_{56}$H$_{102}$O$_{10}$Na: 957.7365; Observed: 957.7357.

Example 13

Synthesis of (2S,3R,4R)-2-hexacosanoyloxy-11-octadecyn-1-yl α-D-galactopyranoside (Compound 23)

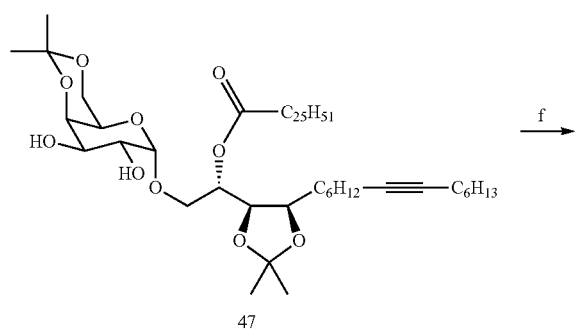

47

(Step f)

To a solution of compound 47 (35 mg, 0.037 mmol) in dichloromethane-acetonitrile (1:1, 14 ml) was added water (82 mg). Thereto was added 46% aqueous hydrofluoric acid solution (about 32 mg), and the mixture was stirred at room temperature for 15 min. Immediately, the mixture was neutralized with saturated aqueous sodium hydrogen carbonate, filtered, and diluted with dichloromethane. The mixture was washed with saturated aqueous sodium hydrogen carbonate, dried over magnesium sulfate, filtered and concentrated under reduced pressure. The residue was purified by silica gel column chromatography and eluted with CHCl$_3$-MeOH (19:1) to give a mixture (about 1:1, 18 mg, 56%) of compound 23 (6 mg, 19%) and a compound wherein the cerotic acid moiety of compound 23 is converted to the C4-position hydroxyl group was obtained as a wax-like substance. The Rf value of each compound by thin layer chromatography was compound 23 (Rf=0.495) and C4 converted product (Rf=0.433) in the ethyl acetate-methanol (19:1) system. The mixture was purified again by silica gel column chromatography to give the title compound 23.

$[\alpha]_D^{28}$+31.1 (c 0.33, CHCl$_3$-CH$_3$OH (11:1)). IR $\nu_{max}$ (KBr) 3382-3330, 2922, 2851, 1735, 1468 cm$^{-1}$. 500 MHz $^1$H NMR (CDCl$_3$-CD$_3$OD, 10:1) δ 0.88 (3H, t, J=6.9 Hz), 0.89 (3H, t, J=7.0 Hz), 1.22-1.69 (64H, m), 2.13 (4H, t, J=7.1 Hz), 2.34 (2H, m), 3.60-3.78 (6H, m), 3.83 (1H, dd, J=3.7, 7.2 Hz), 4.02-4.07 (2H, m), 4.16 (1H, t, J=7.7 Hz), 4.88 (1H, d, J=4.7 Hz, anomeric H), 5.10 (1H, dt, J=4.3, 9.9 Hz). 125 MHz $^{13}$C NMR (CDCl$_3$-CD$_3$OD, 10:1) 13.98, 14.05, 18.68, 18.70, 22.52, 22.64, 24.84, 25.69, 28.52, 28.83, 29.10, 29.12, 29.13, 29.17, 29.28, 29.32, 29.47, 29.61, 29.66, 29.68, 31.33, 31.88, 32.01, 34.29, 63.85, 67.53, 71.52, 71.88, 71.90, 72.13, 72.14, 73.66, 73.67, 74.71, 80.08, 80.28, 101.72, 173.56. ESIMS: m/z 877.67 [M+Na]$^+$. HRESIMS: calcd. for C$_{50}$H$_{94}$O$_{10}$Na, 877.6739; observed, 877.6742.

The above-mentioned compound 24 can also be produced by the following method.

Example 14

Synthesis of (2S,3R,4R)-2-hexacosanoyloxy-3,4-O-isopropylideneoctadecyl α-D-galactopyranoside (Compound 22')

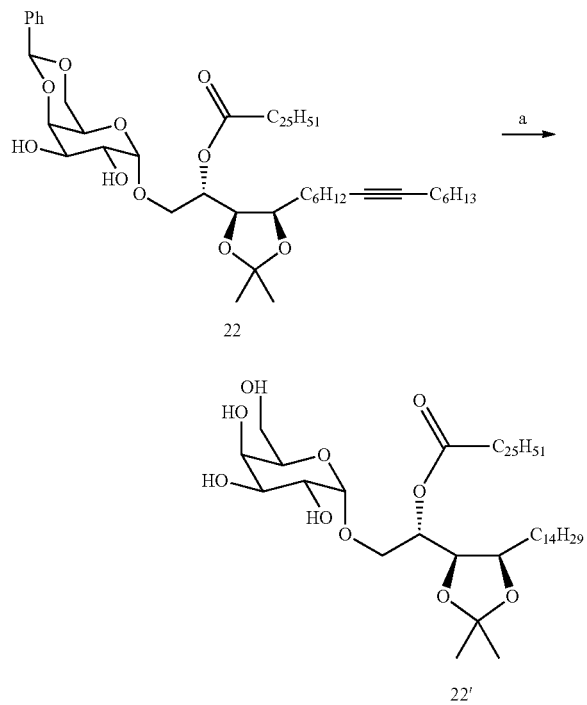

(Step a)

A solution of compound 22 (20 mg, 0.020 mmol) in tetrahydrofuran (20 ml) was subjected to hydrogenolysis using 20% Pd(OH)$_2$ carbon (20 mg) as a catalyst at room temperature for 16 hr. As a result of purification by preparative thin layer chromatography (eluent: trichloromethane-methanol (9:1)), the title compound 22' (12 mg, 66%) was obtained [Although the position where the compound is present cannot be detected by UV detector, since the concentration varies while the mixture is wet with the eluent after removal of the thin layer plate from the developed layer, the position can be specified. Thus, the position was scraped and eluted with CHCl$_3$-MeOH (7:1)]. Alternatively, it was purified by silica gel column chromatography and eluted with trichloromethane-methanol (19:1, further 9:1) to give the title compound 22' (15 mg, 82%).

IR $\nu_{max}$(KBr) 3367 (broad), 2919, 2850, 1732, 1471 cm$^{-1}$. 500 MHz $^1$H NMR (CDCl$_3$) δ 0.88 (6H, t, J=6.8 Hz), 1.25 (70H, bs), 1.34 (3H, s), 1.43 (3H, s), 1.53-1.67 (2H, m), 2.26-2.35 (4H, m, containing two OH), 2.59 (1H, d, J=3.1 Hz), 2.83 (1H, s, OH), 3.71 (1H, dd, J=5.7, 11.3 Hz), 3.75-3.88 (4H, m), 3.95 (1H, m), 4.04 (1H, dd, J=1.7, 11.5 Hz), 4.10 (1H, bs), 4.16-4.18 (2H, m), 4.93 (1H, d, J=3.2 Hz, anomeric H), 5.04 (1H, m). ESIMS: m/z 921.7 [M+Na]$^+$. HRESIMS: Calcd. for C$_{52}$H$_{102}$O$_{10}$Na: 921.7365. Observed: 921.7357.

Production Example 21

Synthesis of (2S,3S,4R)-1-t-butyldimethylsilyloxy-2-hydroxy-3,4-O-isopropylideneoctadecane (Compound 34)

(Step a)

To a solution of compound 28 (500 mg, 1.062 mmol) in ethyl acetate (20 ml) was added 20% Pd(OH)$_2$-carbon (200 mg) as a catalyst, and the mixture was subjected to hydrogenation under a hydrogen atmosphere. The mixture was left standing at room temperature for 1 hr, filtered, concentrated, purified by silica gel column chromatography and eluted with hexane-ethyl acetate (19:1) to give the title compound 34 (478 mg, 95%) as an oil.

IR: $\nu_{max}$(KBr) 3535 (broad), 2926, 2856, 1517, 1464 cm$^{-1}$. 500 MHz $^1$H NMR (CDCl$_3$) δ 0.09 (6H, s), 0.88 (3H, t, J=6.8 Hz), 0.91 (9H, s), 1.25 (23H, bs), 1.32 (3H, s), 1.40 (3H, s), 1.52-1.59 (2H, m), 1.72 (1H, m), 3.64-3.70 (2H, m), 3.82 (1H, m), 3.91 (1H, dd, J=5.6, 8.8 Hz), 4.17 (1H, m). EIMS: m/z 457 [M–CH$_3$]$^+$. HREIMS: calcd. for C$_{26}$H$_{53}$O$_4$Si: 457.3713; observed, 457.3717.

Production Example 22

Synthesis of (2S,3R,4R)-1,2-di-t-butyldimethylsilyloxy-3,4-O-isopropylideneoctadecane (Compound 35)

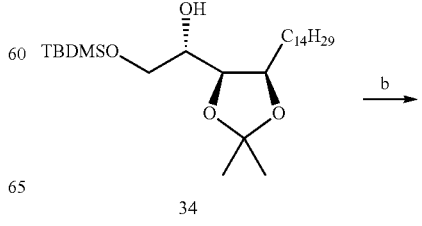

-continued

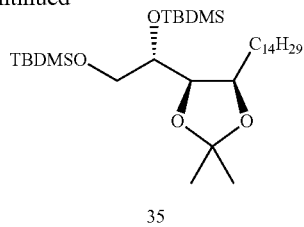

35

(Step b)

To a solution of compound 34 (180 mg, 0.381 mmol) in dichloromethane (10 ml) were added 2,6-lutidine (204 mg, 1.903 mmol) and t-butyldimethylsilyl trifluoromethanesulfonate (302 mg, 1.142 mmol) and the mixture was stirred at room temperature for 1 hr. The mixture was diluted with dichloromethane, washed with saturated aqueous sodium hydrogen carbonate and saturated brine, dried over magnesium sulfate, filtered and concentrated. The concentrate was purified by silica gel column chromatography and eluted with hexane-ethyl acetate (19:1) to give the title compound 35 (221 mg, 99%) as an oil.

Production Example 23

Synthesis of (2S,3S,4R)-2-t-butyldimethylsilyloxy-3,4-O-isopropylideneoctadecan-1-ol (Compound 36)

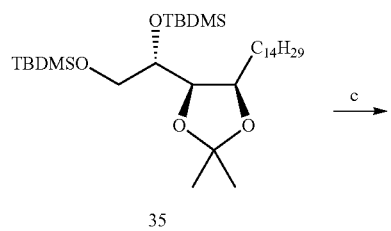

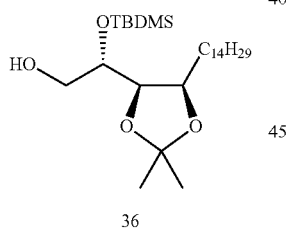

(Step c)

To a solution of compound 35 (6.41 g, 10.92 mmol) in pyridine (48 ml) and THF (80 ml) was added HF-pyridine (16 ml) at 0° C. and the mixture was stirred for 4 hr at room temperature. The mixture was diluted with ethyl acetate and neutralized with a solid sodium hydrogen carbonate powder. Saturated aqueous sodium hydrogen carbonate was added dropwise by small portions and the ethyl acetate layer was separated. The layer was washed with saturated brine, dried over magnesium sulfate, filtered and concentrated. The concentrate was purified by silica gel column chromatography and eluted with hexane-ethyl acetate (19:1, further 4:1) to give a starting compound 35 (2.12 g, 33% recovery) and the title compound 36 (2.34 g, 45%) as an oil.

IR: $\nu_{max}$(KBr) 3500 (broad) cm$^{-1}$. 500 MHz $^1$H NMR (CDCl$_3$) δ 0.11 (3H, s), 0.13 (3H, s), 0.88 (12H, bs), 1.26 (26H, bs), 1.35 (3H, s), 1.43 (3H, s), 2.26 (1H, t, J=4.5 Hz, OH), 3.72-3.75 (3H, m), 3.83 (1H, m), 4.08 (1H, m), 4.12 (1H, m). EIMS: m/z 457 [M−CH$_3$]$^+$. HREIMS: calcd. for C$_{26}$H$_{53}$O$_4$Si: 457.3713; observed, 457.3710.

Example 15

Synthesis of (2S,3R,4R)-2-t-butyldimethylsilyloxy-3,4-O-isopropylideneoctadecyl 2,3-di-O-benzyl-4,6-O-benzylidene-α-D-galactopyranoside (Compound 38) and (2S,3R,4R)-2-t-butyldimethylsilyloxy-3,4-O-isopropylideneoctadecyl 2,3-di-O-benzyl-4,6-O-benzylidene-β-D-galactopyranoside (Compound 38')

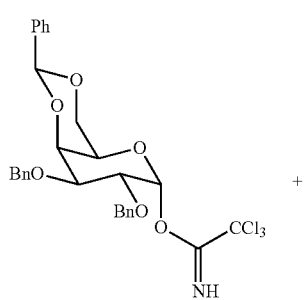

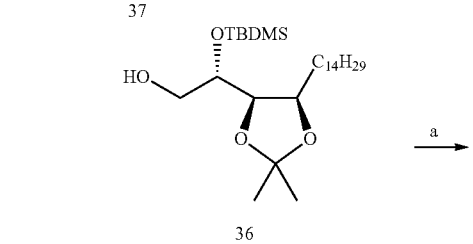

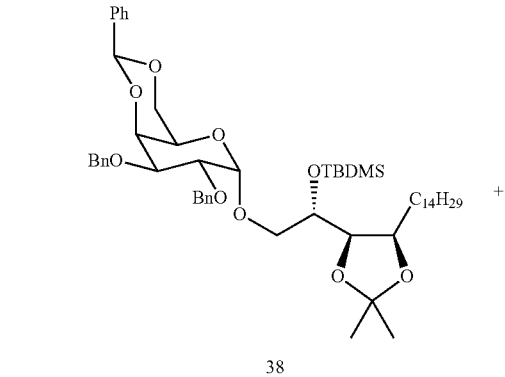

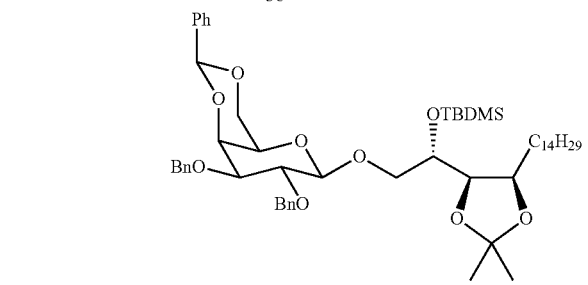

(Step a)

To a solution of a compound 37 known in a literature (C-H, Wong et al., J. Org. Chem., 2002, 67, 4559-4564) (purity about 90%, 540 mg, 0.82 mmol) and compound 36 (355 mg, 0.75 mmol) in dichloromethane (20 ml) was added powder molecular sieve (MS) 4 Å (1.6 g), and the mixture was stirred at room temperature for 30 min. The mixture was further cooled to 0° C., silver trifluoromethanesulfonate (AgOTf) (200 mg, 0.778 mmol) was added and the mixture was stirred for 30 min, and further at room temperature for 2 hr. After filtration, the filtrate was diluted with dichloromethane, washed with saturated aqueous sodium hydrogen carbonate and saturated brine, dried over magnesium sulfate, filtered and concentrated under reduced pressure. The residue was purified by silica gel column chromatography and eluted with hexane-ethyl acetate (9:1, then 4:1) to give the title compound 38 (315 mg, 46%) as a gum-like substance and the title compound 38' (246 mg, 39%) was isolated and purified.

Physical constants of compound 38: Rf=0.412 (hexane:EtOAc=4:1); IR $\nu_{max}$(KBr) 2925, 2854, 1457, 1367, 1249, 1218 cm$^{-1}$; 500 MHz $^1$H NMR (CDCl$_3$) δ 0.06 (3H, s), 0.08 (3H, s), 0.85 (9H, s), 0.90 (3H, m), 1.26 (26+3H, bs), 1.37 (3H, s), 1.52-1.58 (2H, m), 3.58 (1H, m), 3.62 (1H, bs), 3.84 (1H, m), 3.86 (1H, m), 3.99-4.19 (7H, m), 4.68-4.84 (4H, m), 5.01 (1H, d, J=3.5 Hz, anomeric H), 5.49 (1H, s), 7.25-7.40 (13H, m), 7.51-7.53 (2H, m). HRESIMS: calcd. for C$_{54}$H$_{82}$O$_9$SiNa, 925.5620; observed, 925.5612.

Physical constants of compound 38': Rf=0.163 (hexane:EtOAc=4:1); IR $\nu_{max}$(KBr) 2925, 2854, 1456, 1367 cm$^{-1}$. 500 MHz $^1$H NMR (CDCl$_3$) δ 0.13 (3H, s), 0.25 (3H, s), 0.87 (12H, bs), 1.25-1.62 (32H, m, containing two 3H singlets at 1.30 and 1.41 ppm), 3.29 (1H, s), 3.55 (1H, m), 3.77 (1H, d, J=8.8 Hz), 3.87 (1H, m), 3.97-4.10 (6H, m), 4.27 (1H, d, J=12.0 Hz), 4.46 (1H, d, J=7.5 Hz, anomeric H), 4.71-4.77 (2H, m), 4.82, 4.94 (2H, AB-q, J=11.2 Hz), 5.46 (1H, s), 7.26-7.40 (13H, m), 7.53-7.55 (2H, m). HRESIMS: calcd. for C$_{54}$H$_{82}$O$_9$SiNa, 925.5620; observed, 925.5610.

Example 16

Synthesis of (2S,3S,4R)-2-hydroxy-3,4-O-isopropylideneoctadecyl 2,3-di-O-benzyl-4,6-O-benzylidene-α-D-galactopyranoside (Compound 39)

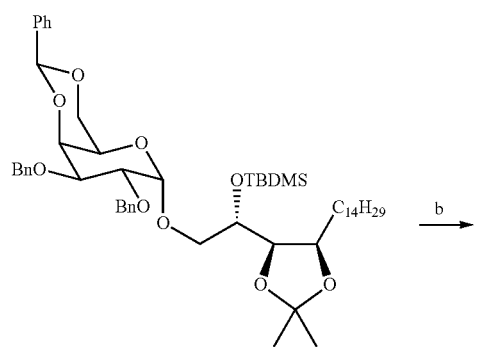

38

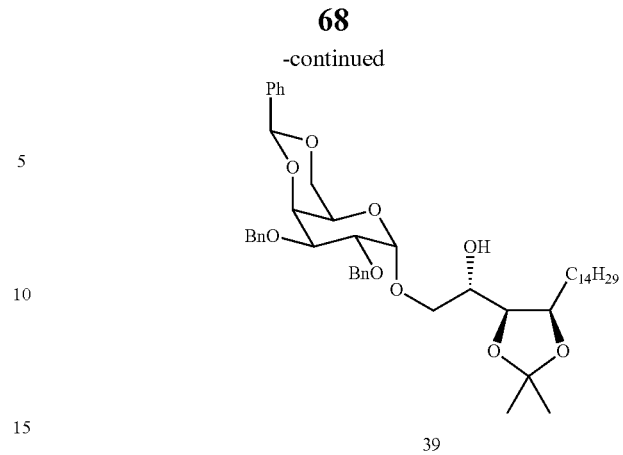

39

(Step b)

A solution of compound 38 (115 mg, 0.127 mmol) and tetrabutylammonium fluoride (1M THF solution, 0.6 ml) in THF (5 ml) was stirred at room temperature for 50 min. The mixture was directly concentrated, diluted with ethyl acetate, washed with saturated aqueous sodium hydrogen carbonate and saturated brine, dried over magnesium sulfate, filtered and concentrated under reduced pressure. The residue was purified by silica gel column chromatography and eluted with hexane-ethyl acetate (4:1) to give the title compound 39 (87 mg, 87%) as a gum-like substance.

IR $\nu_{max}$(KBr) 3511 (br), 2924, 2854, 1456, 1373 cm$^{-1}$. 500 MHz $^1$H NMR (CDCl$_3$) δ 0.88 (3H, t, J=6.8 Hz), 1.25-1.40 (28H, m, containing two 3H singlets at 1.31 and 1.38 ppm), 1.47-1.56 (3H, m), 1.69 (1H, m), 3.24 (1H, bs, OH), 3.47 (1H, dd, J=8.1, 10.8 Hz), 3.69 (1H, s), 3.80 (1H, m), 3.90 (1H, dd, J=5.7, 9.1 Hz), 3.99-4.03 (3H, m), 4.09 (1H, dd, J=3.7, 10.0 Hz), 4.14 (1H, m), 4.21-4.24 (2H, m), 4.68, 4.88 (2H, AB-q, J=11.5 Hz), 4.74, 4.78 (2H, AB-q, J=12.0 Hz), 5.48 (1H, s), 7.27-7.42 (13H, m), 7.51-7.53 (2H, m). ESIMS (positive-ion): m/z 811.5 [M+Na]$^+$. HRESIMS: calcd. for C$_{48}$H$_{68}$O$_9$Na: 811.4756; observed: 811.4750.

Example 17

Synthesis of (2S,3R,4R)-2-hexacosanoyloxy-3,4-O-isopropylideneoctadecyl 2,3-di-O-benzyl-4,6-O-benzylidene-α-D-galactopyranoside (Compound 40)

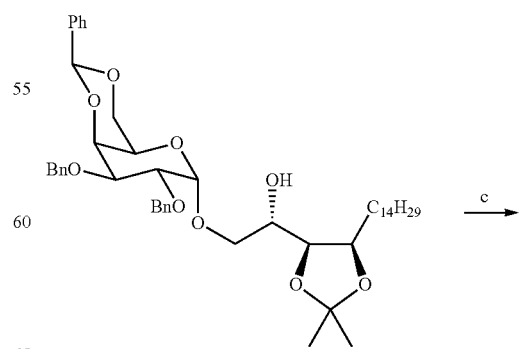

39

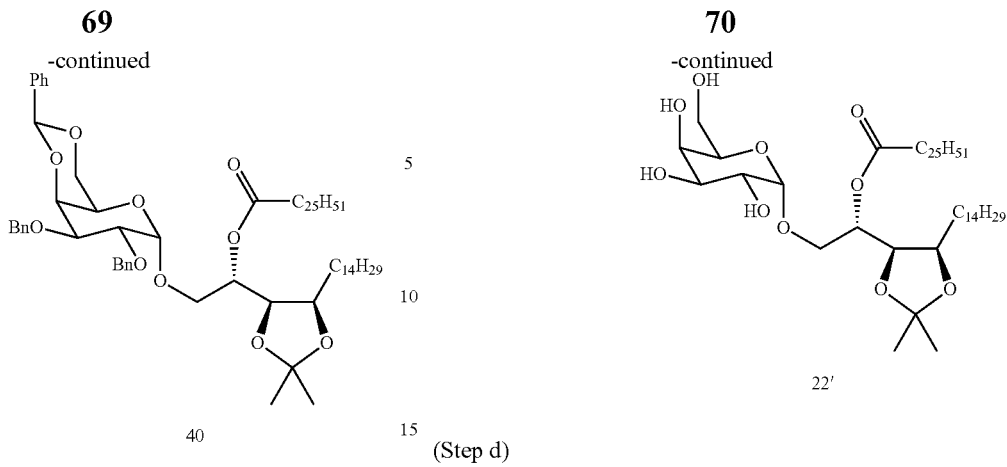

40

(Step c)

A suspension of compound 39 (165 mg, 0.209 mmol), cerotic acid (332 mg, 0.836 mmol), DMAP (511 mg, 4.182 mmol) and 1-[3-(dimethylamino)propyl]-3-ethylcarbodiimide hydrochloride (WSC hydrochloride (802 mg, 4.182 mmol)) in THF-dichloromethane (1:1, 30 ml) was stirred at room temperature for 5 days. The mixture was diluted with trichloromethane, washed with water and saturated brine, dried over magnesium sulfate, filtered and concentrated under reduced pressure. The residue was purified by silica gel column chromatography and eluted with hexane-ethyl acetate (9:1, further 4:1) to give the title compound 40 (228 mg, 93%) as a wax-like substance.

IR $v_{max}$(KBr) 2918, 2850, 1740, 1471, 1170 cm$^{-1}$. 500 MHz $^1$H NMR (CDCl$_3$) δ 0.88 (6H, t, J=6.8 Hz), 1.24-1.56 (78H, m, containing two 3H singlets at 1.32 and 1.41 ppm), 2.23 (2H, m), 3.65 (1H, s), 3.72 (1H, dd, J=5.9, 11.6 Hz), 3.91 (1H, dd, J=2.4, 11.4 Hz), 3.97 (1H, dd, J=3.4, 10.0 Hz), 4.00 (1H, dd, J=1.5, 13.0 Hz), 4.06 (1H, dd, J=3.4, 10.0 Hz), 4.10 (1H, m), 4.19 (1H, d, J=8.1 Hz), 4.20 (1H, s), 4.23 (1H, dd, J=5.7, 8.1 Hz), 4.68, 4.80 (2H, AB-q, J=11.7 Hz), 4.72, 4.80 (2H, AB-q, J=12.3 Hz), 5.00 (1H, d, J=3.5 Hz, anomeric H), 5.02 (1H, m), 5.47 (1H, s), 7.26-7.40 (13H, m), 7.31-7.37 (5H, m), 7.50-7.53 (2H, m). ESIMS: m/z 1189.9 [M+Na]$^+$. HRESIMS: calcd. for C$_{74}$H$_{118}$O$_{10}$Na, 1189.8617; observed, 1189.8611.

Example 18

Synthesis of (2S,3R,4R)-2-hexacosanoyloxy-3,4-O-isopropylideneoctadecyl α-D-galactopyranoside (Compound 22')

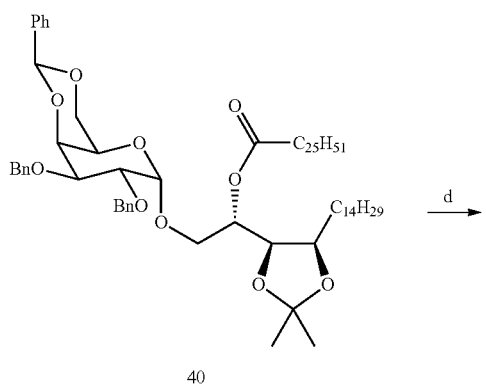

40

(Step d)

A solution of compound 40 (82 mg, 0.091 mmol) in tetrahydrofuran (66 ml) was subjected to hydrogenolysis using 20% Pd(OH)$_2$ carbon (74 mg) as a catalyst at room temperature for 24 hr. The mixture was filtered, and the catalyst was washed with trichloromethane-methanol (7:1), and the mixture was concentrated under reduced pressure. The residue was purified by silica gel column chromatography and eluted with trichloromethane-methanol (39:1, further 9:1) to give the title compound 22' (57 mg, 90%) as a gum-like substance.

The physical constants of compound 22' obtained in this step were the same as those of the following compound 22'.

Example 19

Synthesis of (2S,3R,4R)-2-hexacosanoyloxy-3,4-dihydroxyoctadecyl α-D-galactopyranoside (Compound 24)

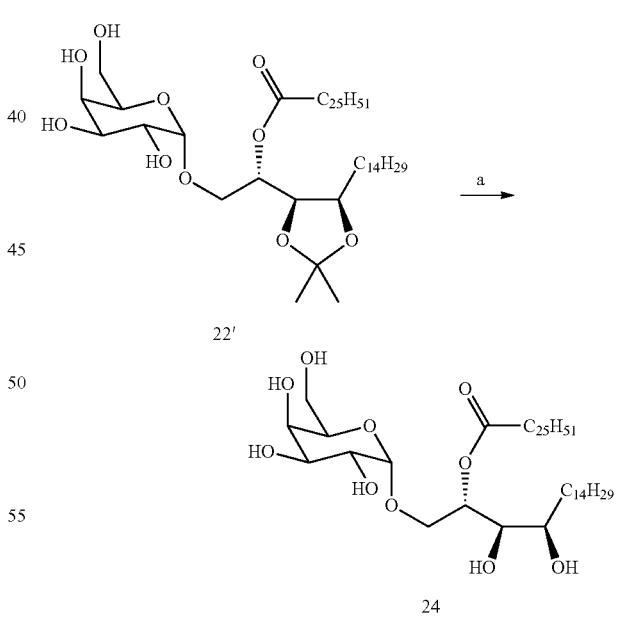

(Step a)

To a solution of compound 22' (50 mg, 0.056 mmol) obtained in Example 14 or Example 18 in dichloromethane-acetonitrile (1:1, 80 ml) was added water (460 mg). Thereto was added 46% aqueous hydrofluoric acid solution (275 mg), and the mixture was stirred at room temperature for 15 min. The mixture was immediately neutralized with saturated aqueous sodium hydrogen carbonate and diluted with trichloromethane. The mixture was washed with saturated aqueous sodium hydrogen carbonate and saturated brine, dried over magnesium sulfate, filtered, and concentrated under reduced pressure. The residue was purified by silica gel column chromatography and eluted with trichloromethane-methanol (19:1, further 9:1) to give the title compound 24 (22 mg, 46%). Alternatively, the mixture was purified by preparative thin layer chromatography (developed with trichloromethane-methanol (7:1)) to give the title compound 24 (18 mg, 38%).

$[\alpha]_D^{28}$ 52.7 (c 0.69, $CHCl_3$-MeOH (9:1)). IR $\nu_{max}$(KBr) 3399 (br), 2919, 2850, 1736, 1468 $cm^{-1}$. 500 MHz $^1$H NMR ($CDCl_3$-$CD_3OD$, 10:1) δ 0.88 (6H, t, J=6.8 Hz), 1.26 (68H, bs), 1.52-1.57 (2H, m), 1.57-1.64 (2H, m), 2.33 (2H, t, J=7.7 Hz), 3.61 (1H, m), 3.72-3.86 (7H, m), 3.99 (1H, d, J=2.7 Hz), 4.03 (1H, dd, J=4.2, 11.5 Hz), 4.91 (1H, d, J=3.7 Hz, anomeric H), 5.10 (1H, q, J=4.9 Hz). 150 MHz $^{13}$C NMR ($CDCl_3$-$CD_3OD$, 10:1) 14.14, 22.74, 24.98, 25.90, 29.24, 29.38, 29.41, 29.56, 29.72, 29.76, 31.98, 32.07, 62.44, 67.20, 69.08, 70.12, 70.33, 71.89, 72.27, 73.41, 99.38, 173.63. ESIMS: m/z 881.7 $[M+Na]^+$. HRESIMS: calcd. for $C_{50}H_{98}O_{10}Na$, 881.7052; observed, 881.7048.

Experimental Example 1

A 1 mg/mL dimethyl sulfoxide (DMSO) solution was prepared for each of α-GalCer, compound 23 and compound 24. The solutions were diluted with saline (manufactured by Otsuka Pharmaceutical Co., Ltd.) containing 0.5% Tween 20 (Bio-Rad) such that the dose would be 100 μg/kg body weight when 200 μL was intraperitoneally administered to one mouse.

Each of the prepared solutions (200 μL) of compounds 23 and 24 was intraperitoneally injected to C57BL/6 mice (2 per group). α-GalCer was used as a control substance, and 200 μL of α-GalCer solution prepared to a dose of 100 μg/kg body weight according to a similar method was injected intraperitoneally. A group administered with a medium (200 μL of saline containing 0.5% Tween 20) was taken as a negative control. The blood (80 μL) was taken from the orbital plexus venosus after the lapse of 6, 12 and 24 hr from the administration, and the serum was prepared.

The content of IFN-γ in the serum after lapse of 6, 12 and 24 hr from the administration was measured by sandwich ELISA (ENDOGEN). In addition, the content of IL-4 in the serum after lapse of 12 hr from the administration was measured by Cytometric bead array system (BD Biosciences), which is one kind of the ELISA method.

Figure 2:
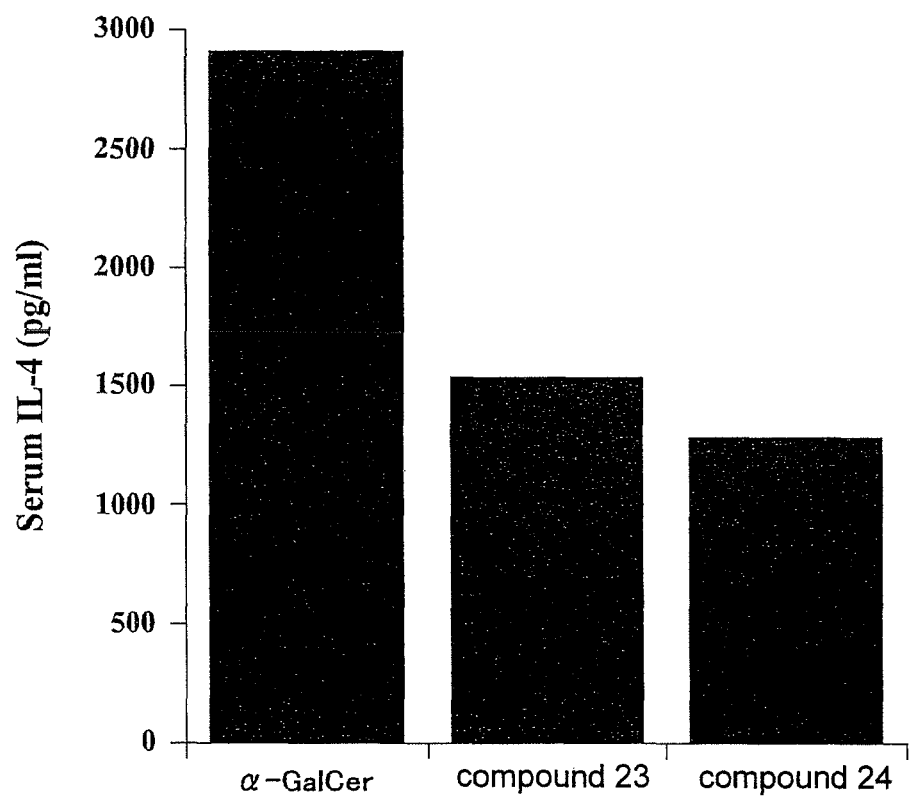
FIG. 2 shows the concentration of IL-4 in the serum after lapse of 12 hr from the administration of synthetic glycolipid (compounds 23 and 24) to mouse in vivo.

The measurement results (average value) of IFN-γ production amount are shown in FIG. 1. The measurement results (average value) of IL-4 production amount (average value) are shown in FIG. 2.

Experimental Example 2

Using α-GalCer and compound 33, and according to a method similar to the above-mentioned Experimental Example 1, the blood (80 μL) was taken from the orbital plexus venosus after the lapse of 3, 6, 12, 24, 36, 48 and 60 hr from the administration, and the serum was prepared.

The content of IFN-γ in the serum after lapse of 3, 6, 12, 24, 36, 48 and 60 hr from the administration was measured by a method similar to the above-mentioned Experimental Example 1. In addition, the content of IL-4 in the serum after lapse of 3, 6 and 12 hr from the administration was measured by a method similar to the above-mentioned Experimental Example 1.

Figure 3:
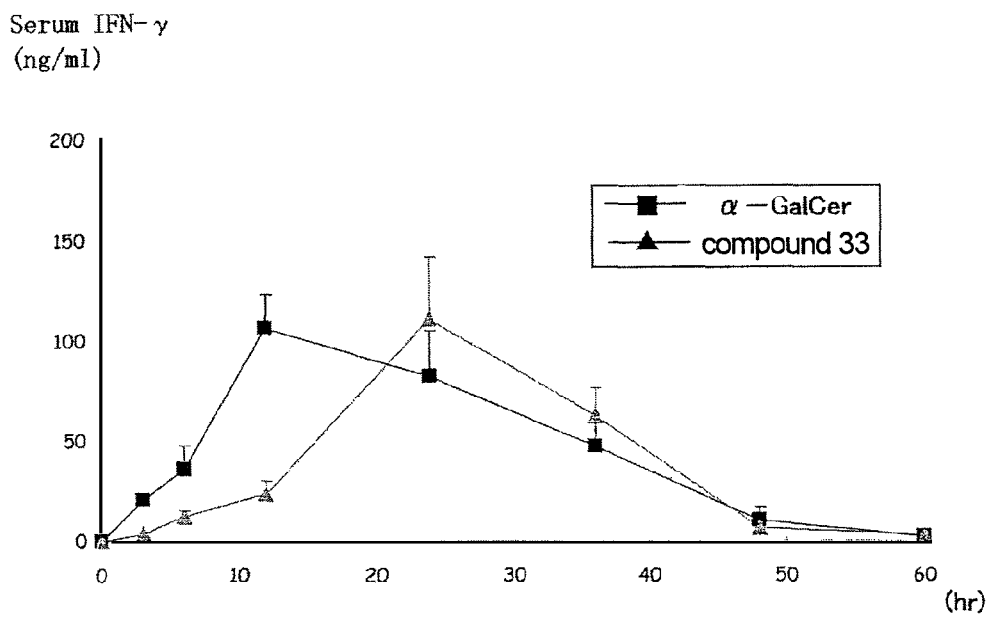
FIG. 3 shows the concentration of IFN-γ in the serum after lapse of indicated time from the administration of synthetic glycolipid (compound 33) to mouse in vivo.
Figure 4:
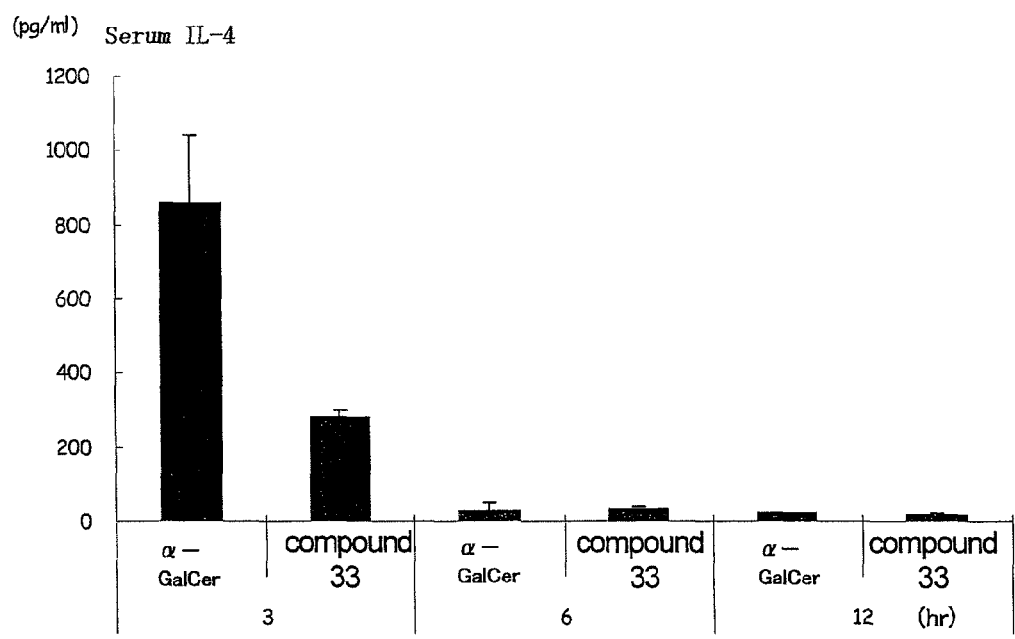
FIG. 4 shows the concentration of IL-4 in the serum after lapse of indicated time from the administration of synthetic glycolipid (compound 33) to mouse in vivo.

The measurement results (average value) of IFN-γ production amount are shown in FIG. 3. The measurement results (average value) of IL-4 production amount (average value) are shown in FIG. 4.

From these results, the administration of compounds 23, 24 and 33 resulted in a lower production of IL-4 and an equivalent or higher production of IFN-γ, as compared to α-GalCer. Thus, it has been clarified that the compound of the present invention produces IFN-γ preferentially or selectively.

Industrial Applicability

The compound (I) of the present invention or a salt thereof can selectively produce IFN-γ, which is one kind of cytokine that activates the function of immunocytes, in a large amount.

Therefore, compound (I) or a salt thereof of the present invention is extremely useful for cancer treatment and effective since it does not cause any particularly noticeable side effects. Consequently, it can reduce physical and mental burdens on patients caused by conventional removal surgery of cancer and the like. In addition, it can also be used as a reagent for biological test and study.

Compound (II) or a salt thereof of the present invention is useful as a synthetic intermediate for compound (I) or a salt thereof. Of compounds (I) of the present invention or a salt thereof, a compound wherein $R^4$ and $R^5$ in combination form a divalent hydrocarbon group having a carbon number of 1 to 5, and form a ring structure together with the adjacent ethylenedioxy (e.g., compounds 32 and 22' described in Examples etc.) is also useful as a synthetic intermediate for compound (I) wherein $R^4$ and $R^5$ are each a hydrogen atom or a salt thereof.

This application is based on patent application No. 2008-233713 filed in Japan, the contents of which are encompassed in full herein.

The invention claimed is:

1. A compound represented by the formula (I):

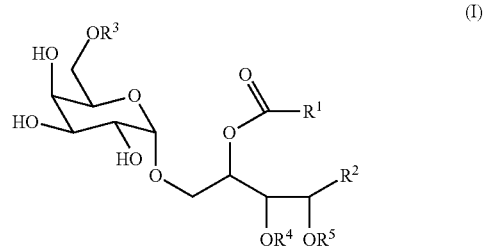

wherein $R^1$ is a hydrocarbon group having a carbon number of 1 to 30, $R^2$ is a hydrocarbon group having a carbon number of 1 to 20, $R^3$ is a hydrogen atom or hydrocarbon group having a carbon number of 1 to 5, $R^4$ and $R^5$ are the same or different and each is a hydrogen atom or a hydrocarbon group having a carbon number of 1 to 5, or $R^4$ and $R^5$ in combination form a divalent hydrocarbon group having a carbon number of 1 to 5, and optionally form a ring structure together with the adjacent ethylenedioxy, or a salt thereof.

2. The compound according to claim 1, wherein $R^1$ is an alkyl group having a carbon number of 1 to 30, an alkenyl group having a carbon number of 2 to 30, or an alkynyl group having a carbon number of 2 to 30, or a salt thereof.

3. The compound according to claim 1, wherein $R^2$ is an alkyl group having a carbon number of 1 to 20, an alkenyl group having a carbon number of 2 to 20, or an alkynyl group having a carbon number of 2 to 20, or a salt thereof.

4. A pharmaceutical composition comprising the compound according to claim 1, or a salt thereof, and a pharmacologically acceptable carrier.

5. A method of immunostimulation in a subject, comprising administering an effective amount of the compound according to claim 1 or a salt thereof to the subject.

6. A method of inducing a selective IFN-γ production in a subject, comprising administering an effective amount of the compound according to claim 1 or a salt thereof to the subject.

7. A method of treating cancer in a subject, comprising administering an effective amount of the compound according to claim 1 or a salt thereof to the subject.

8. A pharmaceutical composition comprising the compound according to claim 2, or a salt thereof, and a pharmacologically acceptable carrier.

9. A method of immunostimulation in a subject, comprising administering an effective amount of the compound according to claim 2 or a salt thereof to the subject.

10. A method of inducing a selective IFN-γ production in a subject, comprising administering an effective amount of the compound according to claim 2 or a salt thereof to the subject.

11. A method of treating cancer in a subject, comprising administering an effective amount of the compound according to claim 2 or a salt thereof to the subject.

12. A pharmaceutical composition comprising the compound according to claim 3, or a salt thereof, and a pharmacologically acceptable carrier.

13. A method of immunostimulation in a subject, comprising administering an effective amount of the compound according to claim 3 or a salt thereof to the subject.

14. A method of inducing a selective IFN-γ production in a subject, comprising administering an effective amount of the compound according to claim 3 or a salt thereof to the subject.

15. A method of treating cancer in a subject, comprising administering an effective amount of the compound according to claim 3 or a salt thereof to the subject.

* * * * *